US007425329B2

(12) United States Patent
Shelton et al.

(10) Patent No.: US 7,425,329 B2
(45) Date of Patent: Sep. 16, 2008

(54) METHODS FOR TREATING BONE CANCER PAIN BY ADMINISTERING A NERVE GROWTH FACTOR ANTAGONIST

(75) Inventors: David L. Shelton, Oakland, CA (US); Patrick William Mantyh, Edina, MN (US)

(73) Assignees: Rinat Neuroscience Corp., South San Francisco, CA (US); Regents of the University of Minnesota, S.E. Minneapolis, MN (US)

( * ) Notice: Subject to any disclaimer, the term of this patent is extended or adjusted under 35 U.S.C. 154(b) by 381 days.

(21) Appl. No.: 11/102,201

(22) Filed: Apr. 7, 2005

(65) Prior Publication Data

US 2005/0265994 A1    Dec. 1, 2005

Related U.S. Application Data

(60) Provisional application No. 60/620,654, filed on Oct. 19, 2004, provisional application No. 60/560,781, filed on Apr. 7, 2004.

(51) Int. Cl.
*A61K 39/395* (2006.01)
*C07K 16/22* (2006.01)
*C12P 21/08* (2006.01)

(52) U.S. Cl. .............. 424/145.1; 424/130.1; 424/133.1; 424/141.1; 530/387.1; 530/387.3; 530/388.24

(58) Field of Classification Search ........................ None
See application file for complete search history.

(56) References Cited

U.S. PATENT DOCUMENTS

| | | | |
|---|---|---|---|
| 3,773,919 A | 11/1973 | Boswell et al. |
| 4,389,404 A | 6/1983 | Zhorov et al. |
| 4,485,045 A | 11/1984 | Regen |
| 4,544,545 A | 10/1985 | Ryan et al. |
| 4,676,980 A | 6/1987 | Segal et al. |
| 4,683,195 A | 7/1987 | Mullis et al. |
| 4,683,202 A | 7/1987 | Mullis |
| 4,754,065 A | 6/1988 | Levenson et al. |
| 4,777,127 A | 10/1988 | Suni et al. |
| 4,800,159 A | 1/1989 | Mullis et al. |
| 4,816,567 A | 3/1989 | Cabilly et al. |
| 5,013,556 A | 5/1991 | Woodle et al. |
| 5,047,335 A | 9/1991 | Paulson et al. |
| 5,130,311 A | 7/1992 | Guillaumet et al. |
| 5,147,294 A | 9/1992 | Smith et al. |
| 5,219,740 A | 6/1993 | Miller et al. |
| 5,278,299 A | 1/1994 | Wong et al. |
| 5,342,942 A | 8/1994 | Jaen et al. |
| 5,409,944 A | 4/1995 | Black et al. |
| 5,422,120 A | 6/1995 | Kim |
| 5,436,265 A | 7/1995 | Black et al. |
| 5,475,995 A | 12/1995 | Livingston |
| 5,500,362 A | 3/1996 | Robinson et al. |
| 5,510,261 A | 4/1996 | Goochee et al. |
| 5,510,368 A | 4/1996 | Lau et al. |
| 5,521,213 A | 5/1996 | Prasit et al. |
| 5,530,101 A | 6/1996 | Queen et al. |
| 5,536,752 A | 7/1996 | Ducharme et al. |
| 5,545,806 A | 8/1996 | Lonberg et al. |
| 5,545,807 A | 8/1996 | Surani et al. |
| 5,550,142 A | 8/1996 | Ducharme et al. |
| 5,552,422 A | 9/1996 | Gauthier et al. |
| 5,565,332 A | 10/1996 | Hoogenboom et al. |
| 5,569,825 A | 10/1996 | Lonberg et al. |
| 5,580,717 A | 12/1996 | Dower et al. |
| 5,580,859 A | 12/1996 | Felgner et al. |
| 5,585,089 A | 12/1996 | Queen et al. |
| 5,593,994 A | 1/1997 | Batt et al. |
| 5,604,253 A | 2/1997 | Lau et al. |
| 5,604,260 A | 2/1997 | Guay et al. |
| 5,616,601 A | 4/1997 | Khanna et al. |
| 5,625,126 A | 4/1997 | Lonberg et al. |
| 5,633,425 A | 5/1997 | Lonberg et al. |
| 5,639,780 A | 6/1997 | Lau et al. |
| 5,656,435 A | 8/1997 | Nakahama et al. |
| 5,661,016 A | 8/1997 | Lonberg et al. |
| 5,693,761 A | 12/1997 | Queen et al. |
| 5,693,762 A | 12/1997 | Queen et al. |
| 5,712,100 A | 1/1998 | Nakahama et al. |
| 5,733,743 A | 3/1998 | Johnson et al. |

(Continued)

FOREIGN PATENT DOCUMENTS

EP    0 345 242 A2    12/1989

(Continued)

OTHER PUBLICATIONS

Clohisy et al. (2003). Bone cancer pain. Cancer. 97 (Suppl. 3):866-873.*

(Continued)

*Primary Examiner*—Christine J. Saoud
*Assistant Examiner*—Jon M. Lockard
(74) *Attorney, Agent, or Firm*—Morrison & Foerster LLP

(57) ABSTRACT

The invention features methods and compositions for preventing or treating bone cancer pain including cancer pain associated with bone metastasis by administering an antagonist of nerve growth factor (NGF). The NGF antagonist may be an anti-NGF (such as anti-hNGF) antibody that is capable of binding hNGF.

17 Claims, 15 Drawing Sheets

U.S. PATENT DOCUMENTS

| | | |
|---|---|---|
| 5,750,373 A | 5/1998 | Garrard et al. |
| 5,766,863 A | 6/1998 | Godowski et al. |
| 5,807,715 A | 9/1998 | Morrison et al. |
| 5,814,482 A | 9/1998 | Dubensky, Jr. et al. |
| 5,821,337 A | 10/1998 | Carter et al. |
| 5,843,942 A | 12/1998 | Breault et al. |
| 5,844,092 A | 12/1998 | Presta et al. |
| 5,866,692 A | 2/1999 | Shitara et al. |
| 5,877,016 A | 3/1999 | Presta et al. |
| 5,891,650 A | 4/1999 | Godowski et al. |
| 5,981,568 A | 11/1999 | Kunz et al. |
| 5,997,867 A | 12/1999 | Waldmann et al. |
| 6,017,878 A | 1/2000 | Saragovi et al. |
| 6,022,875 A | 2/2000 | Zimmer et al. |
| 6,027,927 A | 2/2000 | Presta et al. |
| 6,054,297 A | 4/2000 | Carter et al. |
| 6,127,401 A | 10/2000 | Singh et al. |
| 6,153,189 A | 11/2000 | Presta et al. |
| 6,180,370 B1 | 1/2001 | Queen et al. |
| 6,180,377 B1 | 1/2001 | Morgan et al. |
| 6,210,671 B1 | 4/2001 | Co |
| 6,265,150 B1 | 7/2001 | Terstappen et al. |
| 6,291,247 B1 | 9/2001 | Riopelle et al. |
| 6,306,849 B1 | 10/2001 | Hudkins et al. |
| 6,331,415 B1 | 12/2001 | Cabilly et al. |
| 6,350,861 B1 | 2/2002 | Co et al. |
| 6,359,130 B1 | 3/2002 | Singh et al. |
| 6,376,471 B1 | 4/2002 | Lawrence, III et al. |
| 6,399,780 B1 | 6/2002 | Hudkins |
| 6,413,942 B1 | 7/2002 | Felgner et al. |
| 6,436,908 B1 | 8/2002 | Koch et al. |
| 6,492,380 B1 | 12/2002 | Ross et al. |
| 6,506,559 B1 | 1/2003 | Fire et al. |
| RE38,103 E | 4/2003 | Guay et al. |
| 6,548,062 B2 | 4/2003 | Buchkovich et al. |
| 6,548,640 B1 | 4/2003 | Winter |
| 6,649,605 B2 | 11/2003 | Olesen et al. |
| 6,919,426 B2 | 7/2005 | Boone et al. |
| 2001/0046959 A1 | 11/2001 | Buchkovich et al. |
| 2002/0028779 A1 | 3/2002 | High et al. |
| 2002/0072543 A1 | 6/2002 | Olesen et al. |
| 2002/0146416 A1 | 10/2002 | Presta et al. |
| 2003/0008807 A1 | 1/2003 | Levine et al. |
| 2003/0072746 A1 | 4/2003 | Miller |
| 2003/0203923 A1 | 10/2003 | Ross et al. |
| 2004/0038874 A1 | 2/2004 | Omoigui |
| 2004/0071701 A1 | 4/2004 | Delafoy et al. |
| 2004/0097562 A1 | 5/2004 | Olesen et al. |
| 2004/0121959 A1 | 6/2004 | Boone et al. |
| 2004/0131615 A1 | 7/2004 | Shelton et al. |
| 2004/0228862 A1 | 11/2004 | Shelton et al. |
| 2004/0237124 A1 | 11/2004 | Pons et al. |
| 2004/0253244 A1 | 12/2004 | Shelton et al. |
| 2005/0074821 A1 | 4/2005 | Wild, Jr. et al. |
| 2005/0222035 A1 | 10/2005 | Boone et al. |

FOREIGN PATENT DOCUMENTS

| | | |
|---|---|---|
| EP | 0 345 242 A3 | 12/1989 |
| EP | 0 418 590 A1 | 3/1991 |
| EP | 0 418 590 B1 | 3/1991 |
| EP | 0 519 596 A1 | 12/1992 |
| EP | 0 519 596 B1 | 12/1992 |
| EP | 0 524 968 B1 | 2/1993 |
| FR | 2 807 660 A1 | 10/2001 |
| GB | 2200651 A | 8/1988 |
| JP | 63-295588 A | 12/1988 |
| JP | 03-163905 A | 7/1991 |
| JP | 05-076384 A | 3/1993 |
| JP | 06-317587 A | 11/1994 |
| WO | WO-87/04462 A1 | 7/1987 |
| WO | WO-89/09225 A1 | 10/1989 |
| WO | WO-90/07936 A1 | 7/1990 |
| WO | WO-90/10644 A1 | 9/1990 |
| WO | WO-90/11092 A1 | 10/1990 |
| WO | WO-91/00360 A1 | 1/1991 |
| WO | WO-91/02805 A2 | 3/1991 |
| WO | WO-91/02805 A3 | 3/1991 |
| WO | WO-91/14445 A1 | 10/1991 |
| WO | WO-92/20373 A1 | 11/1992 |
| WO | WO-93/03769 A1 | 3/1993 |
| WO | WO-93/06213 A1 | 4/1993 |
| WO | WO-93/10218 A1 | 5/1993 |
| WO | WO-93/11230 A1 | 6/1993 |
| WO | WO-93/19191 A1 | 9/1993 |
| WO | WO-93/25234 A1 | 12/1993 |
| WO | WO-93/25698 A1 | 12/1993 |
| WO | WO-94/03622 A1 | 2/1994 |
| WO | WO-94/04690 A1 | 3/1994 |
| WO | WO-94/12649 A2 | 6/1994 |
| WO | WO-94/23697 A1 | 10/1994 |
| WO | WO-94/28938 A1 | 12/1994 |
| WO | WO-95/00655 A1 | 1/1995 |
| WO | WO-95/07994 A2 | 3/1995 |
| WO | WO-95/07994 A3 | 3/1995 |
| WO | WO-95/11984 A2 | 5/1995 |
| WO | WO-95/11984 A3 | 5/1995 |
| WO | WO-95/13796 A1 | 5/1995 |
| WO | WO-95/25795 A1 | 9/1995 |
| WO | WO-95/30763 A2 | 11/1995 |
| WO | WO-95/30763 A3 | 11/1995 |
| WO | WO-96/17072 A2 | 6/1996 |
| WO | WO-96/17072 A3 | 6/1996 |
| WO | WO-97/15593 A1 | 5/1997 |
| WO | WO-97/21732 A1 | 6/1997 |
| WO | WO-97/42338 A1 | 11/1997 |
| WO | WO-98/06048 A2 | 2/1998 |
| WO | WO-98/17278 A1 | 4/1998 |
| WO | WO-98/19674 A2 | 5/1998 |
| WO | WO-98/19674 A3 | 5/1998 |
| WO | WO-99/53055 A2 | 10/1999 |
| WO | WO-99/53055 A3 | 10/1999 |
| WO | WO-99/58572 A1 | 11/1999 |
| WO | WO-00/53211 A2 | 9/2000 |
| WO | WO-00/53211 A3 | 9/2000 |
| WO | WO-00/69829 A1 | 11/2000 |
| WO | WO-00/73344 A2 | 12/2000 |
| WO | WO-00/73344 A3 | 12/2000 |
| WO | WO-01/27160 A1 | 4/2001 |
| WO | WO-01/29058 A1 | 4/2001 |
| WO | WO-01/52843 A1 | 7/2001 |
| WO | WO-01/64247 A2 | 9/2001 |
| WO | WO-01/64247 A3 | 9/2001 |
| WO | WO-01/78698 A2 | 10/2001 |
| WO | WO-01/78698 A3 | 10/2001 |
| WO | WO-01/92513 A1 | 12/2001 |
| WO | WO-02/15924 A1 | 2/2002 |
| WO | WO-02/17914 A2 | 3/2002 |
| WO | WO-02/17914 A3 | 3/2002 |
| WO | WO-02/20479 A1 | 3/2002 |
| WO | WO-02/20513 A1 | 3/2002 |
| WO | WO-02/44321 A2 | 6/2002 |
| WO | WO-02/44321 A3 | 6/2002 |
| WO | WO-02/096458 A1 | 12/2002 |
| WO | WO-02/102232 A2 | 12/2002 |
| WO | WO-02/102232 A3 | 12/2002 |
| WO | WO-03/022261 A1 | 3/2003 |
| WO | WO-2004/026329 | 4/2004 |
| WO | WO-2004/28448 | 4/2004 |
| WO | WO-2004/032852 A2 | 4/2004 |
| WO | WO-2004/032852 A3 | 4/2004 |
| WO | WO-2004/032870 A2 | 4/2004 |
| WO | WO-2004/032870 A3 | 4/2004 |
| WO | WO-2004/058184 A2 | 7/2004 |

| WO | WO-2004/065560 A2 | 8/2004 |
| WO | WO-2004/073653 A2 | 9/2004 |
| WO | WO-2004/096122 A2 | 11/2004 |
| WO | WO-2005/000194 A2 | 1/2005 |
| WO | WO-2005/000194 A3 | 1/2005 |
| WO | WO-2005/019266 A2 | 3/2005 |
| WO | WO-2005/019266 A3 | 3/2005 |
| WO | WO-2005/111077 A2 | 11/2005 |
| WO | WO-2005/111077 A3 | 11/2005 |
| WO | WO-2006/077441 A1 | 7/2006 |

OTHER PUBLICATIONS

Goblirsch et al. (2006). Biology of bone cancer pain. Clin. Cancer Res. 12(Suppl. 20 Pt. 2):6231s-6235s.*

Urch et al. (2003). Alterations in dorsal horn neurones in a rat model of cancer-induced bone pain. Pain. 106(3):347-356.*

Abbadie, C. et al. (Jun. 24, 2003). "Impaired Neuropathic Pain Responses in Mice Lacking the Chemokine Receptor CCR2," *Proc. Natl. Acad. Sci. USA* 100(13):7947-7952.

Aley, K.O. et al. (1996). "Delayed Sympathectomy After a Prolonged Hyperalgesia Results in a Subsequent Enhanced Acute Hyperalgesic Response," *Neuroscience* 71(4):1083-1090.

Al-Lazikani, B. et al. (1997). "Standard Conformations for the Canonical Structures of Immunoglobulins," *J. Molec. Biol.* 273:927-948.

Aloe, L. et al. (1992). "Nerve Growth Factor and Distribution of Mast Cells in the Synovium of Adult Rats," *Clin. Exp. Rheumatol.* 10:203-204.

Aloe, L. et al. (Mar. 1992). "Nerve Growth Factor in the Synovial Fluid of Patients with Chronic Arthritis," *Arth. Rheum.* 35(3):351-355.

Aloe, L. et al. (1993). "Level of Nerve Growth Factor and Distribution of Mast Cells in the Synovium of Tumour Necrosis Factor Transgenic Arthritic Mice," *Int. J. Tissue Reactions* 15(4):139-143.

Amann, R. et al. (1995). "Intraplantar Injection of Nerve Growth Factor into the Rat Hind Paw: Local Adema and Effects on Thermal Nociceptive Threshold," *Pain* 64:323-329.

American Chemical Society (1987-1991). *Chemical Abstracts, 12th Collective Index, Chemical Substances*, vols. 106-115, p. 34237CS, col. 3, lines 5-7.

American Chemical Society (1987-1991). *Chemical Abstracts, 12th Collective Index, Chemical Substances*, vols. 106-115, p. 34237CS, col. 3, lines 55-60.

American Chemical Society (1987-1991). *Chemical Abstracts, 12th Collective Index, Chemical Substances*, vols. 106-115, p. 34237CS, col. 3, lines 66-69.

American Chemical Society (1987-1991). *Chemical Abstracts, 12th Collective Index, Chemical Substances*, vols. 106-115, p. 34238CS, col. 1, lines 41-44.

American Chemical Society (1987-1991). *Chemical Abstracts, 12th Collective Index, Chemical Substances*, vols. 106-115, p. 34238CS, col. 2, lines 25-27.

American Chemical Society (1987-1991). *Chemical Abstracts, 12th Collective Index, Chemical Substances*, vols. 106-115, p. 34238CS, col. 2, lines 32-33.

American Chemical Society (1987-1991). *Chemical Abstracts, 12th Collective Index, Chemical Substances*, vols. 106-115, p. 34239CS, col. 3, lines 48-50.

American Chemical Society (1987-1991). *Chemical Abstracts, 12th Collective Index, Chemical Substances*, vols. 106-115, p. 34239CS, col. 3, lines 52-53.

Andreev, N.Y. et al. (1995). "Peripheral Administration of Nerve Growth Factor in the Adult Rat Produces a Thermal Hyperalgesia that Requires the Presence of Sympathetic Post-Ganglionic Neurones," *Pain* 63:109-115.

Apfel, S.C. et al. (1996). "Nerve Growth Factor Regulates the Expression of Brain-Derived Neurotrophic Factor mRNA in the Peripheral Nervous System," *Mol. Cell. Neurosci* 7:134-142.

Armour, K.L. et al. (1999). "Recombinant Human IgG Molecules Lacking Fcγ Receptor I Binding and Monocyte Triggering Activities," *Eur. J. Immunol.* 29:2613-2624.

Bischoff, S.C. et al. (May 15, 1992). "Effect of Nerve Growth Factor on the Release of Inflammatory Mediators by Mature Human Basophils," *Blood* 79(10):2662-2669.

Boettger, M.K. et al. (2002). "Calcium-Activated Potassium Channel SK1- and IK1-like Immunoreactivity in Injured Human Sensory Neurones and its Regulation by Neurotrophic Factors," *Brain* 125:252-263.

Borsani, G. et al. (1990). "cDNA Sequence of Human β-NGF," *Nuc. Acids Res.* 18(13):4020.

Bracci Laudiero, L. et al. (1992). "Multiple Sclerosis Patients Express Increased Levels of β-Nerve Growth Factor in Cerebrospinal Fluid," *Neurosci Lett.* 147:9-12.

Bracci-Laudiero, L. et al. (May 1993). "Increased Levels of NGF in Sera of Systemic Lupus Erythematosus Patients," *NeuroReport* 4(5):563-565.

Braun, A. et al. (1998). "Role of Nerve Growth Factor in a Mouse Model of Allergic Airway Inflammation and Asthma," *Eur. J. Immunol.* 28:3240-3251.

Brennan, T.J. et al. (1998). "Role of Nerve Growth Factor in a Rat Model for Postoperative Pain," *Society for Neoroscience Abstracts*, 28th Annual Meeting, Los Angeles, CA, Nov. 7-12, 1998, 24(1):880. Abstract No. 394.4.

Brown, B.A. et al. (Jul. 1, 1987). "Tumor-Specific Genetically Engineered Murine/Human Chimeric Monoclonal Antibody," *Cancer Res.* 47:3577-3583.

Buchman, V.L. et al. (1993). "Different Neurotrophins are Expressed and Act in a Developmental Sequence to Promote the Survival of Embryonic Sensory Neurons," *Development* 118:989-1001.

Buck, D.W. et al. (Apr. 1982). "Monoclonal Antibodies Specific For Cell Culture Mycoplasmas," *In Vitro* 18(4):377-381.

Caraceni, A. et al. (Mar. 2002). "Pain Measurement Tools and Methods in Clinical Research in Palliative Care: Recommendations of an Expert Working Group of the European Association of Palliative Care," *J. Pain Symptom Manage.* 23(3):239-255.

Chao, M.V. et al. (1986). "Gene Transfer and Molecular Cloning of the Human NGF Receptor," *Science* 232:518-521.

Chaplan, S.R. et al. (1994). "Quantitative Assessment of Tactile Allodynia in the Rat Paw," *J. Neuroscience Methods* 53:55-63.

Chiou, H.C. et al. (1994). "In Vivo Gene Therapy via Receptor-Mediated DNA Delivery," In *Gene Therapeutics: Methods and Applications of Direct Gene Transfer* J.A. Wolff, ed. Birkhäuser, pp. 143-156.

Choi, S-S. et al. (2003). "Antinociceptive Mechanisms of Orally Administered Decursinol in the Mouse," *Life Sciences* 73(4):471-485.

Chothia, C. et al. (Dec. 1989). "Conformations of Immunoglobulin Hypervariable Regions," *Nature* 342:877-883.

Chuang, H-H. et al. (Jun. 21, 2001). "Bradykinin and Nerve Growth Factor Release the Capsaicin Receptor From PtdIns(4,5)P$_2$-Mediated Inhibition," *Nature* 411:957-962.

Chun, L.L.Y. et al. (1977). "Role of Nerve Growth Factor in the Development of Rat Sympathetic Neurons in Vitro, II. Developmental Studies," *The Journal of Cell Biology.* 75:705-711.

Clackson, T. et al. (Aug. 15, 1991). "Making Antibody Fragments Using Phage Display Libraries," *Nature* 352:624-628.

Clohisy, D.R. et al. (2003). "Skeletal Complications of Malignancy: Bone Cancer Pain," *Clinical Orthopaedics and Related Research* 415S:S279-S288.

Colquhoun, A. et al. (2004). "Differential Activity of the Nerve Growth Factor (NGF) Antagonist PD90780 [7-(Benzolylamino)-4,9-dihydro-4-methyl-9-oxo-pyrazolo[5,1-*b*]quinazoline-2-carboxylic Acid] Suggests Altered NGF-p75$^{NTR}$ Interactions in the Presence of TrkA," *J. Pharmacol. Exp. Ther.* 310(2):505-511.

Connelly, S. et al. (Feb. 1995). "In Vivo Gene Delivery and Expression of Physiological Levels of Functional Human Factor VIII in Mice," *Human Gene Therapy* 6:185-193.

Corey, E. et al. (Jun. 1, 2002). "Establishment and Characterization of Osseous Prostate Cancer Models: Intra-Tibial Injection of Human Prostate Cancer Cells," *Prostate* 52(1):20-33.

Crowley, C. et al. (Mar. 25, 1994). "Mice Lacking Nerve Growth Factor Display Perinatal Loss of Sensory and Sympathetic Neurons yet Develop Basal Forebrain Cholinergic Neruons," *Cell* 76:1001-1011.

Curiel, D.T. et al. (1992). "High-Efficiency Gene Transfer Mediated by Adenovirus Coupled to DNA-Polylysine Complexes," *Hum. Gene Ther.* 3:147-154.

Daugherty, B.L. et al. (1991). "Polymerase Chain Reaction Facilitates the Cloning, CDR-Grafting, and Rapid Expression of a Murine Monoclonal Antibody Directed Against the CD18 Component of Leukocyte Integrins," *Nucl. Acids Res.* 19(9):2471-2476.

DiMarco, E. et al. (Oct. 25, 1993). "Nerve Growth Factor Binds to Normal Human Keratinocytes Through High and Low Affinity Receptors and Stimulates Their Growth by a Novel Autocrine Loop," *J. Biol. Chem.* 268(30):22838-22846.

Dyck, P.J. et al. (1997). "Intradermal Recombinant Human Nerve Growth Factor Induces Pressure Allodynia and Lowered Heat-Pain Threshold in Humans," *Neurology* 48:501-505.

Edoff, K. et al. (Feb. 2000). "Retrograde Tracing and Neuropeptide Immunohistochemistry of Sensory Neurones Projecting to the Cartilaginous Distal Femoral Epiphysis of Young Rats," *Cell & Tissue Research* 299(2):193-200.

Eide, F.F. et al. (May 15, 1996). "Naturally Occurring Truncated trkB Receptors Have Dominant Inhibitory Effects on Brain-Derived Neurotrophic Factor Signaling," *J. Neurosci.* 16(10):3123-3129.

Eppstein, D.A. et al. (Jun. 1985). "Biological Activity of Liposome-Encapsulated Murine Interferon γ is Mediated by a Cell Membrane Receptor," *Proc. Natl. Acad. Sci. USA* 82:3688-3692.

Falcini, F. et al. (1996). "Increased Circulating Nerve Growth Factor is Directly Correlated with Disease Activity in Juvenile Chronic Arthritis," *Ann. Rheum. Dis.* 55:745-748.

Fawcett, D.W. (1986). "Bone" Chapter 8 *In A Textbook of Histology*, Dreibelbis, D. ed., Eleventh Edition, W.B. Saunders Co.: Philadelphia, PA, pp. 211-216 and Table of Contents pp. v-xi.

Findeis, M.A. et al. (May 1993). "Targeted Delivery of DNA for Gene Therapy Via Receptors," *Trends Biotechnol.* 11:202-205.

Fjell, J. et al. (Feb. 1999). "In Vivo NGF Deprivation Reduces SNS Expression and TTX-R Sodium Currents in IB4-Negative DRG Neurons," *J. Neurophysiol.* 81(2):803-810.

Foster, P.A. et al. (2002). "Cellular Pathology Changes in Rat Skin Following Intradermal Injection of Nerve Growth Factor: Neutrophil-Dependent and -Independent Events," *J. Pathol.* 197:245-255.

GenBank Accession No. L17077, "The Use of the RACE Method to Clone Hybridoma cDNA When V Region Primers Fail," created on Feb. 7, 1995, located at <http://www.ncbi.nih.gov>, last visited on Mar. 18, 2004, two pages.

GenBank Accession No. L17078, "The Use of the RACE Method to Clone Hybridoma cDNA When V Region Primers Fail," created on Feb. 7, 1995, located at <http://www.ncbi.nih.gov>, last visited on Mar. 18, 2004, two pages.

GenBank Accession No. NM_002506, "Histamine Enhances the Production of Nerve Growth Factor in Human Keratinocytes," created on Dec. 23, 2003, located at <http://www.ncbi.nih.gov>, last visited on Jun. 11, 2004, four pages.

GenBank Accession No. U39608, "Two Distinct Monoclonal Antibodies Raised Against Mouse Beta Nerve Growth Factor: Generation of Bi-Specific Anti-Nerve Growth Factor Anti-Horseradish Peroxidase Antibodies for Use in a Homogenous Enzyme Immunoassay," created on Mar. 25, 1999, located at <http://www.ncbi.nih.gov>, last visited on Mar. 18, 2004, two pages.

GenBank Accession No. U39609, "Two Distinct Monoclonal Antibodies Raised Against Mouse Beta Nerve Growth Factor: Generation of Bi-Specific Anti-Nerve Growth Factor Anti-Horseradish Peroxidase Antibodies for Use in a Homogenous Enzyme Immunoassay," created Jan. 28, 1999, located at <http://www.ncbi.nih.gov>, last visited on Mar. 18, 2004, two pages.

Gould, H.J. III et al. (2000). "A Possible Role for Nerve Growth Factor in the Augmentation of Sodium Channels in Models of Chronic Pain," *Brain Res.* 854:19-29.

Greene, L.A. et al. (Jul. 1976). "Establishment of a Noradrenergic Clonal Line of Rat Adrenal Pheochromocytoma Cells Which Respond to Nerve Growth Factor," *Proc. Nat. Acad. Sci. USA* 73(7):2424-2428.

Griffiths, A.D. et al. (1993). "Human Anti-Self Antibodies with High Specificity From Phage Display Libraries," *EMBO J.* 12(2):725-734.

Hains, B.C. et al. (2002). "Differential Electrohysiological Effects of Brain-Derived Neurotrophic Factor on Dorsal Horn Neurons Following Chronic Spinal Cord Hemisection Injury in the Rat," *Neurosci. Lett.* 320:125-128.

Halliday, D.A. et al. (Jun. 1998). "Elevated Nerve Growth Factor Levels in the Synovial Fluid of Patients With Inflammatory Joint Disease," *Neurochem. Res.* 23(6):919-922.

Halvorson, K.G. et al. (Oct. 15, 2005). "A Blocking Antibody to Nerve Growth Factor Attenuates Skeletal Pain Induced by Prostate Tumor Cells Growing in Bone," *Cancer Res.* 65(20):9426-9435.

Hasselström, J. et al. (Jul. 1996). "Disposition and Analgesic Effects of Systemic Morphine, Morphine-6-glucuronide and Normorphine in Rat," *Pharmacology & Toxicology* 79(1):40-46.

Hongo, J. S. et al. (2000). "Antibody Binding Regions on Human Nerve Growth Factor Identified by Homolog- and Alanine-Scanning Mutagenesis," *Hybridoma* 19(3):215-227.

Honoré, P. et al. (2000). "Cellular and Neurochemical Remodeling of the Spinal Cord in Bone Cancer Pain," *Prog. Brain Res.* 129:389-397.

Honoré, P. et al. (May 2000). "Osteoprotegerin Blocks Bone Cancer-Induced Skeletal Destruction, Skeletal Pain and Pain-Related Neurochemical Reorganization of the Spinal Cord," *Nat. Med.* 6(5):521-528.

Honoré, P. et al. (Jun. 23, 2000). "Murine Models of Inflammatory, Neuropathic and Cancer Pain Each Generates a Unique Set of Neurochemical Changes in the Spinal Cord and Sensory Neurons," *Neuroscience* 98(3):585-598.

Horigome, K. et al. (Jul. 15, 1993). "Mediator Release from Mast Cells by Nerve Growth Factor," *J. Biol. Chem.* 268(20):14881-14887.

Hunt, S.P. et al. (Aug. 13, 1987). "Induction of *c-fos*-like Protein in Spinal Cord Neurons Following Sensory Stimulation," *Nature* 328:632-634.

Hwang, K.J. et al. (Jul. 1980). "Hepatic Uptake and Degradation of Unilamellar Sphingomyelin/Cholesterol Liposomes: A Kinetic Study," *Proc. Natl. Acad. Sci. USA* 77(7):4030-4034.

Iadarola, M.J. et al. (1988). "Differential Activation of Spinal Cord Dynorphin and Enkephalin Neurons During Hyperalgesia: Evidence Using cDNA Hybridization," *Brain Res.* 455(2):205-212.

Johnson, K.S. et al. (1993). "Human Antibody Engineering," *Current Opinion in Structural Biology* 3:564-571.

Jolly, D. (1994). "Viral Vector Systems for Gene Therapy," *Cancer Gene Therapy* 1(1):51-64.

Jones, P.T. et al. (May 29, 1986). "Replacing the Complementarity-Determining Regions in a Human Antibody with Those from a Mouse," *Nature* 321:522-525.

Kabat, E.A. et al. (1991). *Sequences of Proteins of Immunological Interest*, Fifth Edition, National Institutes of Health: Bethesda, MD pp. iii-xi (Table of Contents Only.).

Kaplitt, M.G. et al. (Oct. 1994). "Long-Term Gene Expression and Phenotypic Correction Using Adeno-Associated Virus Vectors in the Mammalian Brain," *Nature Genetics* 8:148-153.

Karlsson, R. et al. (1994). "Kinetic and Concentration Analysis Using BIA Technology," *Methods: A Companion to Methods in Enzymology*, Granzow, R. ed. Academic Press, Inc. 6:99-110.

Kassel, O. et al. (2001). "Local Increase in the Number of Mast Cells and Expression of Nerve Growth Factor in the Bronchus of Asthmatic Patients After Repeated Inhalation of Allergen at Low-Dose," *Clin. Exp. Allergy* 31:1432-1440.

Katz, J. et al. (Apr. 1999). "Measurement of Pain," *Surg. Clin. North Am.* 79(2):231-252.

Kawamoto, K. et al. (2002). "Nerve Growth Factor Activates Mast Cells Through the Collaborative Interaction with Lysophosphatidylserine Expressed on the Membrane Surface of Activated Platelets," *J. Immunol.* 168:6412-6419.

Kerr, B.J. et al. (Oct. 2001). "A Role For the TTX-Resistant Sodium Channel Nav 1.8 in NGF-Induced Hyperalgesia, But Not Neuropathic Pain," *NeuroReport* 12(14):3077-3078.

Kimura, O. et al. (1994). "Retroviral Delivery of DNA into the Livers of Transgenic Mice Bearing Premalignant and Malignant Hepatocellular Carcinomas," *Human Gene Therapy* 5:845-852.

Klein, R. et al. (May 18, 1990). "The *trkB* Tyrosine Protein Kinase Gene Codes for a Second Neurogenic Receptor That Lacks the Catalytic Kinase Domain," *Cell* 61:647-656.

Knüsel, B. et al. (1991). "K-252b Is a Selective and Nontoxic Inhibitor of Nerve Growth Factor Action on Cultured Brain Neurons," *J. Neurochemistry* 57:955-962.

Knüsel, B. et al. (1992). "K-252b Selectively Potentiates Cellular Actions and *trk* Tyrosine Phosphorylation Mediated by Neurotrophin-3," *J. Neurochemistry* 59:715-722.

Kohler, B. et al. (Aug. 7, 1975). "Continuous Cultures of Fused Cells Secreting Antibody of Predefined Specificity," *Nature* 256:495-497.

Koizumi, S. et al. (Feb. 1988). "K-252a: A Specific Inhibitor of the Action of Nerve Growth Factor of PC12 Cells," *J. Neuroscience* 8(2):715-721.

Lamballe, F. et al. (1993). "*trkC* Encodes Multiple Neurotrophin-3 Receptors with Distinct Biological Properties and Substrate Specificities," *EMBO J.* 12(8):3083-3094.

Leon, A. et al. (Apr. 1994). "Mast Cells Synthesize, Store, and Release Nerve Growth Factor," *Proc. Natl. Acad. Sci. USA* 91:3739-3743.

Levi-Montalcini, R. et al. (Jul. 1968). "Nerve Growth Factor," *Physiol. Rev.* 48(3):534-569.

Lewin, G.R. et al. (May 1993). "Nerve Growth Factor-Induced Hyperalgesia in the Neonatal and Adult Rat," *J. Neurosci.* 13(5):2136-2148.

Lewin, G.R. et al. (1994). "Peripheral and Central Mechanisms of NGF-Induced Hyperalgesia," *European Journal of Neuroscience* 6:1903-1912.

Li, Y-X. et al. (Sep. 1998). "Expression of a Dominant Negative TrkB Receptor, T1, Reveals a Requirement For Presynaptic Signaling in BDNF-Induced Synaptic Potentiation in Cultured Hippocampal Neurons," *Proc. Natl. Acad. Sci. USA* 95:10884-10889.

Lindholm, D. et al. (1990). "Glucocorticoid Hormones Negatively Regulate Nerve Growth Factor Expression In Vivo and In Cultured Rat Fibroblasts," *Eur. J. Neurosci.* 2:795-801.

Lindsay, R.M. (Jul. 1988)."Nerve Growth Factors (NGF, BDNF) Enhance Axonal Regeneration But Are Not Required For Survival of Adult Sensory Neurons," *J. Neurosci.* 8(7):2394-2405.

Lindsay, R.M. et al. (Jan. 26, 1989). "Nerve Growth Factor Regulates Expression of Neuropeptide Genes in Adult Sensory Neurons," *Nature* 337:362-364.

Liu, Z.Z. et al. (Nov. 15, 1997). "Critical Role of TrkB and Brain-Derived Neurotrophic Factor in the Differentiation and Survival of Retinal Pigment Epithelium," *J. Neurosci.* 17(22):8749-8755.

Lobuglio, A.F. et al. (Jun. 1989). "Mouse/Human Chimeric Monoclonal Antibody in Man: Kinetics and Immune Response," *Proc. Natl. Acad. Sci. USA* 86:4220-4224.

Lonberg, N. et al. (1995). "Human Antibodies From Transgenic Mice," *Int. Rev. Immunol.* 13:65-93.

Luger, N.M. et al. (May 15, 2001). "Osteoprotegerin Diminishes Advanced Bone Cancer Pain," *Cancer Res.* 61:4038-4047.

Luger, N.M. et al. (2002). "Efficacy of Systemic Morphine Suggests a Fundamental Difference in the Mechanisms that Generate Bone Cancer vs. Inflammatory Pain," *Pain* 99:397-406.

Mach, D.B. et al. (2002). "Origins of Skeletal Pain: Sensory and Sympathetic Innervation of the Mouse Femur," *Neuroscience* 113(1):155-166.

Mantyh, P.W. et al. (Mar. 2002). "Molecular Mechanisms of Cancer Pain," *Nature Reviews Cancer* 2(3):201-209.

Marks, J.D. et al. (1991). "By-Passing Immunization: Human Antibodies From V-Gene Libraries Displayed on Phage," *J. Mol. Biol.* 222:581-597.

Marks, J.D. et al. (Jul. 1992). "By-Passing Immunization: Building High Affinity Human Antibodies by Chain Shuffling," *Bio/Technol.* 10:779-783.

Matsuda, H. et al. (Sep. 1988). "Nerve Growth Factor Promotes Human Hemopoietic Colony Growth and Differentiation," *Proc. Natl. Acad. Sci. USA* 85:6508-6512.

McCafferty, J. et al. (Dec. 6, 1990). "Phage Antibodies: Filamentous Phage Displaying Antibody Variable Domains," *Nature* 348:552-554.

McCarthy, B.G. et al. (Oct. 1995). "Cutaneous Innervation in Sensory Neuropathies," *Neurology* 45:1848-1855.

Michael, G.J. et al. (Nov. 1, 1997). "Nerve Growth Factor Treatment Increases Brain-Derived Neurotrophic Factor Selectively in TrkA-Expressing Dorsal Root Ganglion Cells and in Their Central Terminations Within the Spinal Cord," *J. Neurosci* 17(21):8476-8490.

Miletic, G. et al. (2002). "Increases in the Concentration of Brain Derived Neurotrophic Factor in the Lumbar Spinal Dorsal Horn are Associated with Pain Behavior Following Chronic Constriction Injury in Rats," *Neurosci Lett*. 319:137-140.

Molander, C. et al. (1987). "Spinal Cord Projections From Hindlimb Muscle Nerves in the Rat Studied by Transganglionic Transport of Horseradish Peroxidase, Wheat Germ Agglutinin Conjugated Horseradish Peroxidase, or Horseradish Peroxidase With Dimethylsulfoxide," *J. Comp. Neurol.* 260:246-255.

Morrison, S.L. et al. (Nov. 1984). "Chimeric Human Antibody Molecules: Mouse Antigen-Binding Domains with Human Constant Region Domains," *Proc. Natl. Acad. Sci* 81:6851-6855.

Myers, R.R. et al. (Sep. 1996). "Reduced Hyperalgesia in Nerve-Injured WLD Mice: Relationship to Nerve Fiber Phagocytosis, Axonal Degeneration, and Regeneration in Normal Mice," *Exp. Neurol.* 141(1):94-101.

Noguchi, K. et al. (1991). "Dynorphin Expression and Fos-like Immunoreactivity Following Inflammation Induced Hyperalgesia are Colocalized in Spinal Cord Neurons," *Molecular Brain Research* 10(3):227-233.

Okragly, A.J. et al. (Feb. 1999). "Elevated Tryptase, Nerve Growth Factor, Neurotrophin-3 and Glial Cell Line-Derived Neurotrophic Factor Levels in the Urine of Interstitial Cystitis and Bladder Cancer Patients," *J. Urology* 161:438-442.

Otten, U. et al. (1985). "Nerve Growth Factor Induces Plasma Extravasation in Rat Skin," *Eur. J. Pharmacol*. 106:199-201.

Otten, U. et al. (Dec. 1989). "Nerve Growth Factor Induces Growth and Differentiation of Human B Lymphocytes," *Proc. Natl. Acad. Sci. USA* 86:10059-10063.

Pearce, F.L. et al. (1986). "Some Characteristics of Histamine Secretion From Rat Peritoneal Mast Cells Stimulated with Nerve Growth Factor," *J. Physiol*. 372:379-393.

Peeters, K. et al. (2001). "Production of Antibodies and Antibody Fragments in Plants," *Vaccine* 19:2756-2761.

Petersen, M. et al. (1998). "Nerve Growth Factor Regulates the Expression of Bradykinin Binding Sites on Adult Sensory Neurons Via the Neurotrophin Receptor p75," *Neuroscience* 83(1):161-168.

Petty, B.G. et al. (1994). "The Effect of Systemically Administered Recombinant Human Nerve Growth Factor in Healthy Human Subjects," *Annals Neurol*. 36(2):244-246.

Philip, R. et al. (Apr. 1994). "Efficient and Sustained Gene Expression in Primary T Lymphocytes and Primary and Cultured Tumor Cells Mediated by Adeno-Associated Virus Plasmid DNA Complexed to Cationic Liposomes," *Mol. Cell Biol*. 14(4):2411-2418.

Pollock, D.P. et al. (1999). "Transgenic Milk as a Method For the Production of Recombinant Antibodies," *J. Immunol. Methods* 231:147-157.

Puigdellivol-Sánchez, A. et al. (1998). "Sciatic and Femoral Nerve Sensory Neurones Occupy Different Regions of the L4 Dorsal Root Ganglion in the Adult Rat," *Neurosci. Lett*. 251(3):169-172.

Puigdellivol-Sánchez, A. et al. (Oct. 1, 2000). "Contribution of Femoral and Proximal Sciatic Nerve Branches to the Sensory Innervation of Hindlimb Digits in the Rat," *The Anatomical Record* 260(2):180-188.

Raychaudhuri, S.P. et al. (1998). "Psoriatic Keratinocytes Express High Levels of Nerve Growth Factor," *Acta Derm. Venereol.* 78:84-86.

Riechmann, L. et al. (Mar. 24, 1988). "Reshaping Human Antibodies for Therapy," *Nature* 332:323-327.

Ruberti, F. et al. (1993). "Cloning and Expression of an Anti-Nerve Growth Factor (NGF) Antibody for Studies Using the Neuroantibody Approach," *Cell. Mol. Biol.* 13(5):559-568.

Sabino, M.A.C. et al. (Dec. 15, 2002). "Simultaneous Reduction in Cancer Pain, Bone Destruction, and Tumor Growth by Selective Inhibition of Cyclooxygenase-2," *Cancer Res.* 62:7343-7349.

Sabino, M.A.C. et al. (May 1, 2003). "Different Tumors in Bone Each Give Rise to a Distinct Pattern of Skeletal Destruction, Bone Cancer-Related Pain Behaviors and Neurochemical Changes in the Central Nervous System," *International Journal of Cancer* 104(5):550-558.

Schwartz, F. et al. (2002). "Effect of Helium-Neon Laser Irradiation on Nerve Growth Factor Synthesis and Secretion in Skeletal Muscle Cultures," *J. Photochem Photobiol. B: Biology* 66:195-200.

Schwei, M.J. et al. (Dec. 15, 1999). "Neurochemical and Cellular Reorganization of the Spinal Cord in a Murine Model of Bone Cancer Pain," *J. Neuroscience* 19(24):10886-10897.

Sevarino, K.A. et al. (Jan. 15, 1988). "Biosynthesis of Thyrotropin-Releasing Hormone by a Rat Medullary Thyroid Carcinoma Cell Line," *J. Biol. Chem.* 263(2):620-623.

Sevcik, M.A. et al. (May 2005). "Anti-NGF Therapy Profoundly Reduces Bone Cancer Pain and the Accompanying Increase in Markers of Peripheral and Central Sensitization," *Pain* 115(1-2):128-141.

Sevcik, M.A. et al. (Sep. 2004). "Bone Cancer Pain: The Effects of the Bisphosphonate Alendronate on Pain, Skeletal Remodeling, Tumor Growth and Tumor Necrosis," *Pain* 111(1-2):169-180.

Shaw, D.R. et al. (Jun. 15, 1987). "Characterization of a Mouse-Human Chimeric Monoclonal Antibody (17-1A) To A Colon Cancer Tumor-Assocated Antigen," *J. Immunol.* 138(12):4534-4538.

Shelton, D.L. et al. (Dec. 1984). "Expression of the β-nerve Growth Factor Gene Correlates with the Density of Sympathetic Innervation in Effector Organs," *Proc. Natl. Acad. Sci. USA* 81:7951-7955.

Shu, X. et al. (1999). "Nerve Growth Factor Acutely Sensitizes the Response of Adult Rat Sensory Neurons to Capsaicin," *Neurosci. Lett.* 274(3):159-162.

Smyene, R.J. et al. (Mar. 17, 1994). "Severe Sensory and Sympathetic Neuropathies in Mice Carrying a Disrupted Trk/NGF Receptor Gene," *Nature* 368:246-249.

Steiner, P. et al. (1991). "Interleukin-1β and Tumor Necrosis Factor-α Synergistically Stimulate Nerve Growth Factor Synthesis in Rat Mesangial Cells," *Am. J. Physiol.* 261:F792-F798.

Taglialatela, G. et al. (1996). "Suppression of p140$^{trkA}$ Does Not Abolish Nerve Growth Factor-Mediated Rescue of Serum-Free PC12 Cells," *J. Neurochem.* 66(5):1826-1835.

Thompson, S.W.N. et al. (1995). "Nerve Growth Factor Induces Mechanical Allodynia Associated with Novel A Fibre-Evoked Spinal Reflex Activity and Enhanced Neurokinin-1 Receptor Activation in the Rat," *Pain* 62:219-231.

Thompson, S.W.N. et al. (Jul. 1999). "Brain-Derived Neurotrophic Factor is an Endogenous Modulator of Nociceptive Responses in the Spinal Cord," *Proc. Natl Acad. Sci USA* 96(14)7714-7718.

Tofaris, G.K. et al. (Aug. 1, 2002). "Denervated Schwann Cells Attract Macrophages by Secretion of Leukemia Inhibitory Factor (LIF) and Monocyte Chemoattractant Protein-1 in a Process Regulated by Interleukin-6 and LIF," *J. Neurosci.* 22(15):6696-6703.

Torcia, M. et al. (May 3, 1996). "Nerve Growth Factor Is an Autocrine Survival Factor for Memory B Lymphocytes," *Cell* 85:345-356.

Tsoulfas, P. et al. (May 1993). "The Rat *trkC* Locus Encodes Multiple Neurogenic Receptors That Exhibit Differential Response to Neurotrophin-3 in PC12 Cells," *Neuron* 10:975-990.

Tsujino, H. et al. (Feb. 2000). "Activating Transcription Factor 3 ATF3) Induction by Axotomy in Sensory and Motoneurons: A Novel Neuronal Marker of Nerve Injury," *Molecular & Cellular Neuroscience* 15(2):170-182.

Ueyama, T. et al. (1993). "Production of Nerve Growth Factor by Cultured Vascular Smooth Muscle Cells From Spontaneously Hypertensive and Wistar-Kyoto Rats," *J. Hypertens.* 11:1061-1065.

Ullrich, A. et al. (Jun. 30, 1983). "Human β-Nerve Growth Factor Gene Sequence Highly Homologous to That of Mouse," *Nature* 303:821-825.

Urfer, R. et al. (1997). "Specificity Determinants in Neurotrophin-3 and Design of Nerve Growth Factor-Based trkC Agonists by Changing Central β-Strand Bundle Residues to Their Neurotrophin-3 Analogs," *Biochem.* 36:4775-4781.

Valenzuela, D.M. et al. (May 1993). "Alternative Forms of Rat TrkC With Different Functional Capabilities," *Neuron* 10:963-974.

Vanderah, T.W. et al. (Apr. 2001). "Mechanisms of Opioid-Induced Pain and Antinociceptive Tolerance: Descending Facilitation and Spinal Dynorphin," *Pain* 92(3):5-9.

Verhoeyen, M. et al. (Mar. 25, 1988). "Reshaping Human Antibodies: Grafting an Antilysozyme Activity," *Science* 239:1534-1536.

Waterhouse, P. et al. (1993). "Combinatorial Infection and in vivo Recombination: A Strategy for Making Large Phage Antibody Repertoires," *Nucl. Acids Res.* 21(9):2265-2266.

Winter, G. et al. (Jan. 27, 1991). "Man-Made Antibodies," *Nature* 349:293-299.

Winter, G. et al. (1994). "Making Antibodies by Phage Display Technology," *Annu. Rev. Immunol.* 12:433-455.

Woffendin, C. et al. (Nov. 1994). "Nonviral and Viral Delivery of a Human Immunodeficiency Virus Protective Gene into Primary Human T Cells," *Proc. Natl. Acad. Sci. USA* 91:11581-11585.

Woolf, C.J. et al. (Apr. 15, 1996). "Peripheral Cell Types Contributing to the Hyperalgesic Action of Nerve Growth Factor in Inflammation," *J. Neurosci.* 16(8):2716-2723.

Woolf, N.J. et al. (Feb. 1, 2001). "Elevation of Nerve Growth Factor and Antisense Knockdown of TrkA Receptor During Contextual Memory Consolidation," *J. Neurosci.* 21(3):1047-1055.

Wu, C.H. et al. (Oct. 15, 1989). "Targeting Genes: Delivery and Persistent Expression of a Foreign Gene Driven by Mammalian Regulatory Elements in Vivo," *J. Biol. Chem.* 264(29):16985-16987.

Wu, G.Y. et al. (Aug. 5, 1991). "Receptor-Mediated Gene Delivery in Vivo: Partial Correction of Genetic Analbuminemia in Nagase Rats," *J. Biol. Chem.* 266(22):14338-14342.

Wu, G.Y. et al. (Apr. 15, 1994). "Incorporation of Adenovirus into a Ligand-Based DNA Carrier System Results in Retention of Original Receptor Specificity and Enhances Targeted Gene Expression," *J. Biol. Chem.* 269(15):11542-11546.

Yan, Q. et al. (1991). "Hypotension Induced by Intravascular Administration of Nerve Growth Factor in the Rat," *Clin. Sci.* 80:565-569.

Zenke, M. et al. (May 1990). "Receptor-Mediated Endocytosis of Transferrin-Polycation Conjugates: An Efficient Way to Introduce DNA Into Hematopoietic Cells," *Proc. Natl. Acad. Sci. USA* 87:3655-3659.

International Search Report mailed Feb. 20, 2006, for PCT Application No. PCT/US2005/011786, filed Jul. 4, 2005, five pages.

Jongen, J.L.M. et al. (2002). "Neurotrophic Factors and Cancer Pain: The Expression of NGF, GDNF and BDNF by the Murine Osteolytic Sarcoma Cell Line 2472 in vitro and in vivo and Their Potential Involvement in Bone Cancer Pain," *32nd Annual Meeting of the Society for Neuroscience*, Orlando, FL, (Nov. 2-7, 2002), Abstract 52.2, one page.

Shelton, D.L. et al. (1995). "Neurotrophins and Neurotrophin Antagonists as Potential Therapeutics," *Restorative Neurology and Neuroscience* 8(1-2):99-100.

Adey, N.B. et al. (1996). "Preparation of Second-Generation Phage Libraries" Chapter 16 *In Phage Display of Peptides and Proteins: A Laboratory Manual*, Kay, B.K. et al. eds. Adacemic Press, Inc.: San Diego, CA, pp. 277-291.

Agrawal, S. et al. (1998). "Mixed Backbone Oligonucleotides: Improvement in Oligonucleotide-Induced Toxicity In Vivo, " *Antisense & Nucleic Acid Drug Development* 8:135-139.

Aloe, L. et al. (Aug. 1993). "The Synovium of Transgenic Arthritic Mice Expressing Human Tumor Necrosis Factor Contains a High Level of Nerve Growth Factor," *Growth Factors* 9(2):149-155.

Aloe, L. et al. (1995). "Effect of NGF Antibodies on Mast Cell Distribution, Histamine and Substance P Levels in the Knee Joint of TNF-Arthritic Transgenic Mice," *Rheumatol. Int.* 14:249-252.

Aloe, L. et al. (Sep.-Oct. 1999). "Nerve Growth Factor in the Synovia of Patients with Rheumatoid Arthritis: Correlation with TNF-α and IL-1β and Possible Functional Significance," *Clin. Exp. Rheumatol.* 17(5):632-633.

Altschul, S.F. et al. (1997). "Gapped BLAST and PSI-BLAST: A New Generation of Protein Database Search Programs," *Nucleic Acids Res.* 25(17):3389-3402.

Balint, R. F. et al. (1993). "Antibody Engineering By Parsimonious Mutagenesis," *Gene* 137:109-118.

Banik, R.K. et al. (Nov. 12, 2003). "Anti-NGF Treatment Attenuates Spontaneous Pain and Thermal, but Not Mechanical Hyperalgesia, After Hind Paw Incision in the Rat," *Society for Neuroscience*, Program No. 909.12, one page, Abstract Only.

Barbas III, C.F. et al. (Apr. 1994). "In vitro Evolution of a Neutralizing Human Antibody to Human Immunodeficiency Virus Type 1 to Enhance Affinity and Broaden Strain Cross-Reactivity," *Proc. Natl. Acad. Sci. USA* 91:3809-3813.

Barbas III, C.F. et al. (2001). "Vector pComb3X, Figure 2.2" In "Phage-Display Vectors" Chapter 2 In Phage Display: A Laboratory Manual, Cold Spring Harbor Laboratory Press: Cold Spring Harbor, NY, pp. 2.9-2.13.

Bellamy, N. (May 1989). "Pain Assessment in Osteoarthritis: Experience With the WOMAC Osteoarthritis Index," Semin. Arthritis Rheum. 18(4)Suppl. 2:14-17.

Bellamy, N. et al. (Dec. 1988). "Validation Study of WOMAC: A Health Status Instrument for Measuring Clinically Important Patient Relevant Outcomes to Antirheumatic Drug Therapy in Patients with Osteoarthritis of the Hip or Knee," J. Rheumatol. 15(12):1833-1840.

Bibel, M. et al. (Dec. 1, 2000). "Neurotrophins: Key Regulators of Cell Fate and Cell Shape in the Vertebrate Nervous System," Genes Dev. 14(23):2919-2937.

Bird, R.E. et al. (Oct. 21, 1988). "Single-Chain Antigen-Binding Proteins," Science 242:423-426.

Boerner, P. et al. (Jul. 1, 1991). "Production of Antigen-Specific Human Monoclonal Antibodies From In Vitro-Primed Human Splenocytes," J. Immunol. 147(1):86-95.

Boyd, P.N. et al. (1996). "The Effect of the Removal of Sialic Acid, Galactose and Total Carbohydrate on the Functional Activity of Campath-1H," Mol. Immunol. 32(17/18):1311-1318.

Brennan, T.J. et al. (1996). "Characterization of a Rat Model of Incisional Pain," Pain 64:493-501.

Brennan, T.J. (1999). "Postoperative Models of Nociception," ILAR Journal 40(3):129-136.

Brennan, T.J. et al. (2005). "Mechanisms of Incisional Pain," Anesthesiology Clin. N. Am. 23:1-20.

Brosseau, L. et al. (2003). "Thermotherapy for Treatment of Osteoarthritis," The Cochrane Database of Systematic Reviews Issue 4, Art No. CD004522, pp. 1-20.

Capel, P.J.A. et al. (1994). "Heterogeneity of Human IgG Fc Receptors," Immunomethods 4:25-34.

Chen, Y. et al. (Nov. 5, 1999). "Selection and Analysis of an Optimized Anti-VEGF Antibody: Crystal Structure of an Affinity-Matured Fab in Complex with Antigen," J. Mol. Biol. 293(4):865-881.

Clynes, R. et al. (Jan. 1998). "Fc Receptors Are Required in Passive and Active Immunity to Melanoma," Proc. Natl. Acad. Sci. USA 95:652-656.

Cole, S.P.C. et al. (1985)., "The EBV-Hybridoma Technique and Its Application to Human Lung Cancer" In Monoclonal Antibodies and Cancer Therapy, Reisfeld, R. et al. eds., Alan R. Liss, Inc.: New York, NY, pp. 77-96.

Cromartie, W.J. et al. (1977). "Arthritis in Rats After Systemic Injection of Streptococcal Cells or Cell Walls," The Journal of Experimental Medicine 146:1585-1602.

Dayhoff, M.O. et al. (1978). "A Model of Evolutionary Change in Proteins" Chapter 22 In Atlas of Protein Sequence and Structure, National Biomedical Research Foundation, Washington D.C., 5(Supp.3):345-352.

de Haas, M. et al. (Oct. 1995). "Fcγ Receptors of Phagocytes," J. Lab. Clin. Med. 126(4):330-341.

De Kock, M. et al. (2001). "'Balanced Analgesia' in the Perioperative Period: Is There a Place for Ketamine?"Pain 92:373-380.

Dicou, E. et al. (Sep. 1993). "Natural Autoantibodies Against the Nerve Growth Factor in Autoimmune Diseases," J. Neuroimmunol. 47(2):159-167.

Dicou, E. et al. (Dec. 13, 1993). "Increased Frequency of NGF in sera of Rheumatoid Arthritis and Systemic Lupus Erythematosus Patients," NeuroReport 5(3):321-324.

Dicou, E. et al. (Jan. 1994). "Natural Autoantibodies Against the Nerve Growth Factor in Autoimmune Diseases," J. Neuroimmunol. 49(1):224 (Erratum).

Dicou, E. et al. (1996). "Nerve Growth Factor (NGF) Autoantibodies and NGF in the Synovial Fluid: Implications in Spondylarthropathies," Autoimmunity 24(1):1-9.

Dicou, E. et al. (May 1997). "Evidence That Natural Autoantibodies Against the Nerve Growth Factor (NGF) May Be Potential Carriers of NGF," J. Neuroimmunol. 75:200-203.

Felson, D.T. et al. (Jun. 1993). "The American College of Rheumatology Preliminary Core Set of Disease Activity Measures For Rheumatoid Arthritis Clinical Trials," Arthritis and Rheumatism 36(6):729-740.

Fernihough, J. et al. (Nov. 2004). "Pain Related Behaviour in Two Models of Osteoarthritis in the Rat Knee," Pain 112(1/2):83-93.

Fischer, H.P. et al. (Jun. 1998). "A Possible Role for Saliva as a Diagnostic Fluid in Patients with Chronic Pain," Semin. Arthritis Rheum. 27(6):348-359.

Fries, J.F. et al. (1982). "The Dimensions of Health Outcomes: The Health Assessment Questionnaire, Disability and Pain Scales," J. Rheumatol. 9(5):789-793.

Garcia-Castellano, J.M. et al. (2000). "Is Bone a Target-Tissue for the Nervous System? New Advances on the Understanding of Their Interactions," Iowa Orthop. J. 20:49-58.

Garrett, N.E. et al. (Jul. 11, 1997). "Effect of Capsaicin on Substance P and Nerve Growth Factor in Adjuvant Arthritic Rats," Neurosci. Lett. 230:5-8.

Gavilondo, J.V. et al. (Jul. 2000). "Antibody Engineering at the Millennium," Bio Techniques 29(1):128-145.

Gazzano-Santoro, H. et al. (1996). "A Non-Radioactive Complement-Dependent Cytotoxicity Assay For Anti-CD20 Monoclonal Antibody," J. Immunol. Methods 202:163-171.

GenBank Accession No. CAA09181, created Dec. 2, 1998, located at <http://www.ncbi.nim.nih.gov> lasted visited Oct. 19, 2005, two pages.

GenBank Accession No. P01859, created Jul. 21, 1986, located at <http://www.ncbi.nlm.nih.gov> last visited Oct. 19, 2005, four pages.

Gerstenfeld, L.C. et al. (2003). "Differential Inhibition of Fracture Healing by Non-Selective and Cyclooxygenase-2 Selective Non-Steroidal Anti-Inflammatory Drugs," J. Orthop. Res. 21:670-675.

Guyer, R.L. et al. (Aug. 1976). "Immunoglobulin Binding by Mouse Intestinal Epithelial Cell Receptors," J. Immunol. 117(2):587-593.

Gwak, Y.S. et al. (Jan. 16, 2003). "Attenuation of Mechanical Hyperalgesia Following Spinal Cord Injury by Administration of Antibodies to Nerve Growth Factor in the Rat," Neuroscience Letters 336(2):117-120.

Haws, M.J. et al. (Aug. 1996). "The Effects of Chronic Ketorolac Tromethamine (Toradol) On Wound Healing," Ann. Plas. Surg. 37(2):147-151.

Haynes, M.K. et al. (Dec. 2002). "Phenotypic Characterization of Inflammatory Cells From Osteoarthritic Synovium and Synovial Fluids," Clin. Immunol. 105(3):315-325.

Hein, J. (1990). "Unified Approach to Alignment and Phylogenes" Chapter 39 In Methods in Enzymology, Academic Press, Inc.: San Diego, CA, 183:626-645.

Higgins, D.G. et al. (1989). "Fast and Sensitive Multiple Sequence Alignments on a Microcomputer," CABIOS Communications 5(2):151-153.

Higuchi, R. (1990). "Recombinant PCR" Chapter 22 In PCR Protocols: A Guide to Methods and Applications, Innis, M.A. et al. eds., Academic Press, Inc., pp. 177-183.

Hill, R. (Jul. 2000). "$NK_1$ (Substance P) Receptor Antagonists—Why Are They Not Analgesic in Humans?" Trends Pharmacol. Sci. 21(7):244-246.

Holliger, P. et al. (Jul. 1993). "'Diabodies': Small Bivalent and Bispecific Antibody Fragments," Proc. Natl. Acad. Sci. USA 90:6444-6448.

Honore, P. et al. (2006). "Interleukin-1αβ Gene-Deficient Mice Show Reduced Nociceptive Sensitivity in Models of Inflammatory and Neuropathic Pain but not Post-Operative Pain," Behavioural Brain Research 167:355-364.

Hoogenboom, H. R. et al. (1992). "By-Passing Immunisation: Human Antibodies From Synthetic Repertoires of Germline $V_H$ Gene Segments Rearranged In Vitro," J. Mol. Biol. 227:381-388.

Hsu, T-A. et al. (Apr. 4, 1997). "Differential N-Glycan Patterns of Secreted and Intracellular IgG Produced in Trichoplusia ni Cells," J. Biol. Chem. 272(14):9062-9070.

Huang, E.J. et al. (2001). "Neurotrophins: Roles in Neuronal Development and Function," Annu. Rev. Neurosci. 24:677-736.

Huse, W.D. et al. (Jun. 1993). "Increased Antibody Affinity and Specificity by Codon-Based Mutagenesis," Intern. Rev. Immunol. 10(2-3):129-137.

Iannone, F. et al. (2002). "Increased Expression of Nerve Growth Factor (NGF) and High Affinity NGF Receptor (p140 TrkA) in Human Osteoarthritic Chondrocytes," Rheumatology 41:1413-1418.

International Search Report for PCT Application No. PCT/US03/32083 filed Oct. 8, 2003, mailed Mar. 4, 2005, three pages.
International Search Report for PCT Application No. PCT/US03/32089 filed Oct. 8, 2003, mailed May 17, 2004, three pages.
International Search Report for PCT Application No. PCT/US03/32113, filed Oct. 8, 2003, mailed Apr. 10, 2006, four pages.
International Search Report for PCT Application No. PCT/US04/05162 filed Feb. 19, 2004, mailed Mar. 28, 2006, four pages.
Jefferis, R. et al. (1997). "Glucosylation of Antibody Molecules: Structural and Functional Significance," Chem. Immunol. 65:111-128.
Kasai, M. et al. (1999). "Endogenous Nerve Growth Factor Increases the Sensitivity to Bradykinin in Small Dorsal Root Ganglion Neurons of Adjuvant Inflamed Rats," Neuroscience Letters 272(1):41-44.
Kazemier, B. et al. (1996). "Determination of Active Single Chain Antibody Concentrations in Crude Periplasmic Fractions," J. Immunol. Methods 194(2):201-209.
Kim, J-K. et al. (Oct. 1994). "Localization of the Site of the Murine IgG1 Molecule that is Involved in Binding to the Murine Intestinal Fc Receptor," Eur. J. Immunol. 24(10):2429-2434.
Kuzuna, S. et al. (1975). "Evaluation of Analgesic Agents in Rats with Adjuvant Arthritis," Chem Pharm. Bull. 23(6):1184-1191.
Lambiase, A. et al. (2003). "Clinical Application of Nerve Growth Factor on Human Corneal Ulcer," Arch. Ital. Biol. 141:141-148.
Mahato, R.I. et al. (1997). "Cationic Lipid-Based Gene Delivery Systems: Pharmaceutical Perspectives," Pharm Res. 14(7):853-859.
Manni, L. et al. (1998). "Role of IL-1β and TNF-α in the Regulation of NGF in Experimentally Induced Arthritis in Mice," Rheumatol. Int. 18:97-102.
Matsuda, H. et al. (Feb. 2, 1998). "Role of Nerve Growth Factor in Cutaneous Wound Healing: Accelerating Effects in Normal and Healing-Impaired Diabetic Mice," J. Exp. Med. 187(3):297-330.
McDonald, N.Q. et al. (Dec. 5, 1991). "New Protein Fold Revealed by a 2.3-Å Resolution Crystal Structure of Nerve Growth Factor," Nature 354(6352):411-414.
McMahon, S.B. (Aug. 1995). "The Biological Effects of Endogenous Nerve Growth Factor on Adult Sensory Neurons Revealed by a trkA-IgG Fusion Molecule," Nature Medicine 1(8):774-780.
McMahon, S.B. (Mar. 29, 1996). "NGF as a Mediator of Inflammatory Pain," Phil. Trans. R. Soc. Land. B 351(1338):431-440.
Meenan, R.F. et al. (Sep. 1982). "The Arthritis Impact Measurement Scales," Arthritis and Rheumatism 25(9):1048-1053.
Milstein, C. et al. (Oct. 6, 1983). "Hybrid Hydridomas and Their Use in Immunohistochemistry," Nature 305:537-539.
Møiniche, S. et al. (1997). "Time Course of Subjective Pain Ratings, and Wound and Leg Tenderness After Hysterectomy," Acta Anaesthesiol. Scand. 41:785-789.
Møiniche, S. et al. (Mar. 2002). "A Qualitative and Quantitative Systematic Review of Preemptive Analgesia for Postoperative Pain Relief," Anesthesiology 96(3):725-741.
Muller, Y.A. et al. (Sep. 15, 1998). "VEGF and the Fab Fragment of a Humanized Neutralizing Antibody: Crystal Structure of the Complex at 2.4 Å Resolution and Mutational Analysis of the Interface," Structure 6(9):1153-1167.
Muyldermans, S. (2001). "Single Domain Camel Antibodies: Current Status," Reviews in Molecular Biotechnology 74:277-302.
Myers, E.W. et al. (1988). "Optimal Alignments in Linear Space," CABIOS 4(1):11-17.
Niissalo, S. et al. (Jun. 2002). "Neuropeptides in Experimental and Degenerative Arthritis," Ann. N. Y. Acad. Sci. 966:384-399.
Paulus, H.E. et al. (Apr. 1990). "Analysis of Improvement in Individual Rheumatoid Arthritis Patients Treated with Disease-Modifying Antirheumatic Drugs, Based on the Findings in Patients Treated with Placebo," Arthritis and Rheumatism 33(4):477-484.
Pearson, C.M. et al. (1959). "Studies of Polyarthritis and Other Lesions Induced in Rats by Injection of Mycobacterial Adjuvant, I. General Clinical and Pathologic Characteristics and Some Modifying Factors," Arthritis Rheum. 2:440-459.
Peter, E.A. et al. (Oct. 30, 2001). "Ibuprofen Versus Acetaminophen with Codeine for the Relief of Perineal Pain after Childbirth: A Randomized Controlled Trial," CMAJ 165(9):1203-1209.

Pezet, S. et al. (Feb. 1, 2001). "Differential Regulation of NGF Receptors in Primary Sensory Neurons by Adjuvant-Induced Arthritis in the Rat," Pain 90(1-2):113-125.
Pogatzki, E.M. et al. (2002). "Characterization of Aσ- and C-Fibers Innervating the Plantar Rat Hindpaw One Day After an Incision," J. Neurophysiol. 87:721-731.
Pogatzki, E.M. et al. (2002). "Role of Rostral Medial Medulla in the Development of Primary and Secondary Hyperalgesia After Incision in the Rat," Anesthesiology 96:1153-1160.
Poljak, R. J. (Dec. 15, 1994). "Production and Structure of Diabodies," Structure 2:1121-1123.
Pons, J. et al. (1999). "Energetic Analysis of an Antigen/Antibody Interface: Alanine Scanning Mutagenesis and Double Mutant Cycles on the HyHEL-10/Lysozyme Interaction," Prot. Sci. 8:958-968.
Pozza, M. et al. (May 2000). "A Histochemical Study of the Rheumatoid Synovium: Focus on Nitric Oxide, Nerve Growth Factor High Affinity Receptor, and Innervation," J. Rheumatol. 27(5):1121-1127.
Prodromou, C. et al. (1992). "Recursive PCR: A Novel Technique for Total Gene Synthesis," Protein Eng. 5(8):827-829.
Rader, C. et al. (2001) "Antibody Engineering" Chapter 13 In Phage Display, A Laboratory Manual, Barbas, C.F. et al. eds., Cold Spring Harbor Laboratory Press: Cold Spring Harbor, NY, pp. 13.1-13.15.
Ravetch, J.V. et al. (1991). "Fc Receptors," Ann. Rev. Immunol. 9:457-492.
Rinat Neurosciences. (Date Unknown). "RN624 A New Approach to Pain Therapy," located at <http://64.233.161.104/search?q=cache:nYXEK1HDbdIJ:www.rinatneuro.com/products/RN6...>, last visited Jul. 5, 2006, five pages.
Ro, L-S. et al. (1999). "Effect of NGF and Anti-NGF on Neuropathic Pain in Rats Following Chronic Constriction Injury of the Sciatic Nerve," Pain 79:265-274.
Robinson, D.F. (1971). "Comparison of Labeled Trees with Valency Three," J. Comb. Theor. 11:105-119.
Rosok, M.J. et al. (Sep. 13, 1996). "A Combinatorial Library Strategy for the Rapid Humanization of Anticarcinoma BR96 Fab," The Journal of Biological Chemistry 271(37):22611-22618.
Rossi, J.J. et al. eds. (1999). Intracellular Ribozyme Applications: Principles and Protocols, Horizon Scientific Press: Norfolk, England, pp. iii-iv (Table of Contents Only.).
Roubenoff, R. et al. (1994). "Rheumatoid Cachexia: Cytokine-Driven Hypermetabolism Accompanying Reduced Body Cell Mass in Chronic Inflammation," J. Clin. Invest. 93(6):2379-2386.
Roubenoff, R. et al. (Mar. 1997). "Adjuvant Arthritis as a Model of Inflammatory Cachexia," Arthritis Rheum. 40(3):534-539.
Rudikoff, S. et al. (Mar. 1982). "Single Amino Acid Substitution Altering Antigen-Binding Specificity," Proc. Natl. Acad. Sci. USA 79:1979-1983.
Safieh-Garabedian, B. et al. (Aug. 1995). "Contribution of Interleukin-1β to the Inflammation-Induced Increase in Nerve Growth Factor Levels and Inflammatory Hyperalgesia," Br. J. Pharmacol. 115(7):1265-1275.
Saitou, N. et al. (1987). "The Neighbor-Joining Method: A New Method for Reconstructing Phylogenetic Trees," Mol. Biol. Evol. 4(4):406-425.
Sheets, M.D. et al. (May 1998). "Efficient Construction of a Large Nonimmune Phage Antibody Library: The Production of High-Affinity Human Single-Chain Antibodies to Protein Antigens," Proc. Natl. Acad. Sci. USA 95:6157-6162.
Sneath, P.H.A. et al. (1973). Numerical Taxonomy: The Principles and Practice of Numerical Taxonomy, W. H. Freeman and Company: San Francisco, CA. pp. vii-ix (Table of Contents Only.).
Stedman, T.L. (1982). Illustrated Stedman's Medical Dictionary, Williams & Wilkins: Baltimore, MD, 24th Edition, p. 670.
Szekanecz, Z. et al. (Jun. 2000). "Temporal Expression of Inflammatory Cytokines and Chemokines in Rat Adjuvant-Induced Arthritis," Arthritis & Rheumatism 43(6):1266-1277.
Tang, Y. et al. (Sep. 24, 1999). "Use of a Peptide Mimotope to Guide the Humanization of MRK-16, an Anti-P-Glycoprotein Monoclonal Antibody," The Journal of Biological Chemistry 274(39):27371-27378.
Thompson, J.E. et al. (1999). "A Fully Human Antibody Neutralising Biologically Active Human TGFβ2 for use in Therapy," J. Immunol. Methods 227:17-29.

Umaña, P. et al. (Feb. 1999). "Engineered Glycoforms of an Antineuroblastoma IgG1 with Optimized Antibody-Dependent Cellular Cytotoxic Activity," *Mature Biotech.* 17:176-180.

Vajdos, F.F. et al. (Jul. 5, 2002), "Comprehensive Functional Maps of the Antigen-Binding Site of an Anti-ErbB2 Antibody Obtained with Shotgun Scanning Mutagenesis," *J. Mol. Biol.* 320(2):415-428.

Vaughan, T.J. et al. (Mar. 1996). "Human Antibodies with Sub-Nanomolar Affinities Isolated from a Large Non-Immunized Phage Display Library," *Nature Biotechnology* 14:309-314.

Vigneti, E. et al. (1993). "Production and Characterization of a Monoclonal Antibody Against Nerve Growth Factor (NGF) Which Recognizes Rodent and Human NGF," *Year Immunol.* 7:146-149.

Villanueva, L. (Dec. 2000). "Is There a Gap Between Preclinical and Clinical Studies of Analgesia?" *Trends Pharmacol. Sci.* 21(12):461-465.

Wiesmann, C. et al. (Sep. 9, 1999). "Crystal Structure of Nerve Growth Factor in Complex with the Ligand-Binding Domain of the TrkA Receptor," *Nature* 401(6749):184-188.

Wilbur, W.J. et al. (Feb. 1983). "Rapid Similarity Searches of Nucleic Acid and Protein Data Banks," *Proc. Natl. Acad. Sci. USA* 80:726-730.

Winter, C.A. et al. (Jun. 1966). "Treatment of Adjuvant Arthritis in Rats with Anti-inflammatory Drugs," *Arthritis Rheum.* 9(3):394-404.

Wittwer, A.J. et al. (1990). "Glycosylation at Asn-184 Inhibits the Conversion of Single-Chain to Two-Chain Tissue-Type Plasminogen Activator by Plasmin," *Biochem.* 29:4175-4180.

Woolf, C.J. et al. (1994). "Nerve Growth Factor Contributes to the Generation of Inflammatory Sensory Hypersensitivity," *Neuroscience* 62(2):327-331.

Wright, A. et al. (Jan. 1997). "Effect of Glycosylation on Antibody Function: Implications for Genetic Engineering," *TibTECH* 15:26-32.

Wu, H. et al. (Nov. 19, 1999). "Humanization of a Murine Monoclonal Antibody by Simultaneous Optimization of Framework and CDR Residues," *J. Mol. Biol.* 294(1):151-162.

Wu, S.M. et al. (1998). "Oxidized $\alpha_2$-Macroglobulin ($\alpha_2$M) Differentially Regulates Receptor Binding by Cytokines/Growth Factors: Implications for Tissue Injury and Repair Mechanisms in Inflammation," *The Journal of Immunology* 161:4356-4365.

Wu, Z. et al. (Dec. 2000). "Immunohistochemical Study of NGF and its Receptors in the Synovial Membrane of the Ankle Joint of Adjuvant-Induced Arthritic Rats," *Histochem. Cell Biol.* 114(6):453-459.

Wyss, D.F. et al. (1996). "The Structural Role of Sugars in Glycoproteins," *Current Opin. Biotech* 7:409-416.

Yamamoto, T. et al. (2001). "Spinal N-acetyl-α-linked Acidic Dipeptidase (NAALADase) Inhibition Attenuates Mechanical Allodynia Induced by Paw Carrageenan Injection in the Rat," *Brain Res.* 909:138-144.

Yelton, D.E. et al. (1995). "Affinity Maturation of the BR96 Anti-Carcinoma Antibody by Codon-Based Mutagenesis," *The Journal of Immunology* 155:1994-2004.

Zahn, P.K. et al. (Sep.-Oct. 2002). "Mechanisms for Pain Caused by Incisions," *Regional Anesthesia and Pain Medicine* 27(5):514-516.

Yu, Y.C. et al. (2002). "Two Variables That can be Used as Pain Indices in Experimental Animal Models of Arthritis," *Journal of Neuroscience Methods* 115:107-113.

Zahn, P.K. et al. (Apr. 2004). "Effect of Blockade of Nerve Growth Factor and Tumor Necrosis Factor on Pain Behaviors After Plantar Incision," *The Journal of Pain* 5(3):157-163.

Zola, H. (1987). "Using Monoclonal Antibodies: Soluble Antigens" Chapter 6 *In Monocolonal Antibodies: A Manual of Techniques*, CRC Press, Inc., pp. 147-158.

ATCC Search Results for "911 Mab" located at <http://www.atcc.org/common/catalog/wordSearch/results.cfm>, last visited Aug. 30, 2006, one page.

Berzofsky, J.A. et al. (1993). "Immunogenicity and Antigen Structure" Chapter 8 *In Fundamental Immunology*, Paul, W.E. ed., Raven Press: New York, NY, p. 242.

Kehlet, H. (Apr. 1995). "Synergism Between Analgesics," *Ann. Med.* 27(2):259-262.

Leem, J.W. et al. (2000). "Anti-NGF Treatment Suppresses Abnormal Pain Behaviors Induced After Spinal Cord Injury in the Rat," *30th Annual Meeting of the Society of Neuroscience*, New Orleans, LA, Nov. 4-9, 2000, *Society for Neuroscience Abstracts* 26(2):1690, Abstract No. 633.1.

Owolabi, J.B. et al. (1999). "Characterization of Antiallodynic Actions of ALE-0540, a Novel Nerve Growth Factor Receptor Antagonist in the Rat," *J. Pharmacol. Exp. Ther.* 289(3):1271-1276.

Sequence Alignments for Sequence Searches of Seq ID Nos. 1-8, pp. 1-8.

Sunshine, A. et al. (Jul. 1987). "Analgesic Efficacy of Two Ibuprofen-Codeine Combinations for the Treatment of Postepisiotomy and Postoperative Pain," *Clin. Pharmacol. Ther.* 42(1)374-380.

Supplementary European Search Report mailed Sep. 12, 2006, for EP Application No. 03779091.2 filed Oct. 3, 2003, four pages.

International Search Report for PCT Application No. PCT/US2006/013921 filed Apr. 11, 2006, mailed Jan. 2, 2007, seven pages.

Lane, N. et al. (Sep. 2005). "RN624 (Anti-NGF) Improves Pain and Function in Subjects with Moderate Knee Osteoarthritis: A Phase I Study," *Arthritis & Rheumantism* 52(9-Suppl. S):S461, Abstract No. 1205.

Shelton, D.L. et al. (Jul. 2005). "Nerve Growth Factor Mediates Hyperalgesia and Cachexia in Auto-Immune Arthritis," *Pain* 116(1-2):8-16.

Vastag, B. (Jun. 2006). "Monoclonals Expand into Neural Disorders," *Nature Biotechnology* 24(6):595-596.

Fieischmann, R.M. et al. (2004). "Considerations With the Use of Biological Therapy in the Treatment of Rheumatoid Arthritis," *Expert. Opin. Drug Safety* 3(5):391-403.

Orbach, H. et al. (Dec. 2005). "Intravenous Immunoglobulin: Adverse Effects and Safe Administration," *Clinical Rev. Allergy Immunol.* 29(3):173-184 (Abstract Only), 1 page.

Seaver, S.S. (Aug. 1994). "Monoclonal Antibodies in Industry: More Difficult Than Originally Thought," *Genetic Engineering* 14(14):10, 21.

Stedman, T.L. (2000). "Definition of Osteoarthritis" In *Illustrated Stedman's Medical Dictionary*, Lippincott Williams & Wilkins: Baltimore, MD, 27th Edition, one page.

Suntharalingam, G. et al. (Sep. 7, 2006). "Cytokine Storm in a Phse 1 Trial of the Anti-CD28 Monoclonal Antobody TGN1412," *New England Journal of Medicine* 355(10):1018-1029.

\* cited by examiner

Figure 10 (A-F)
A Spontaneous Guarding
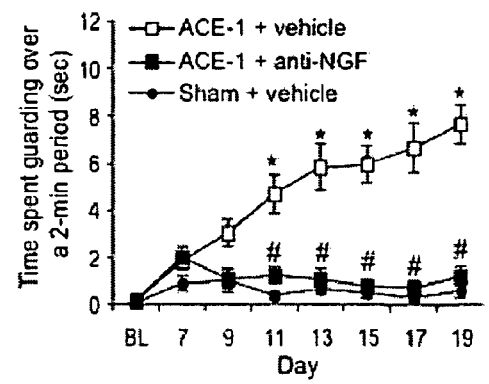
B Spontaneous Flinching
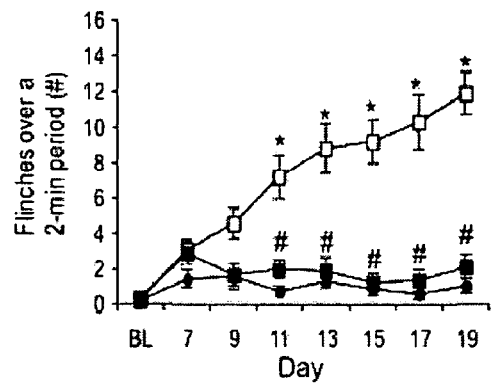
C Thermal Sensitivity
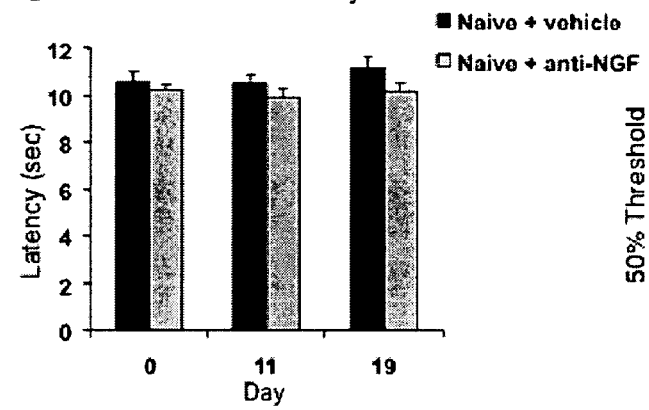
D Mechanical Sensitivity
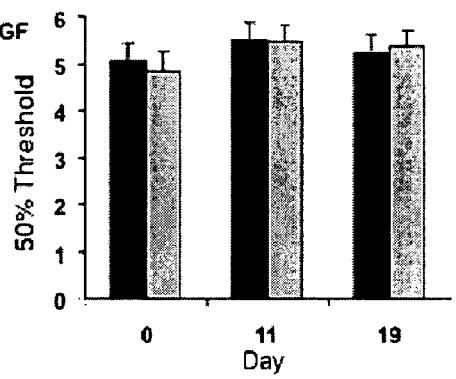
E Spontaneous Guarding
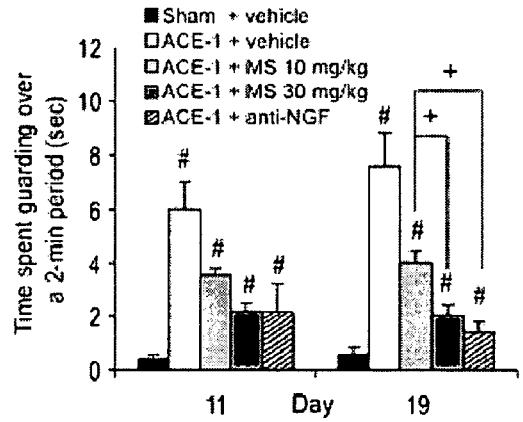
F Spontaneous Flinching
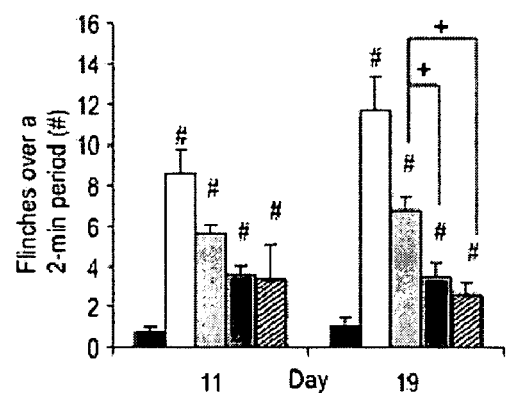

Figure 10 (G, H)
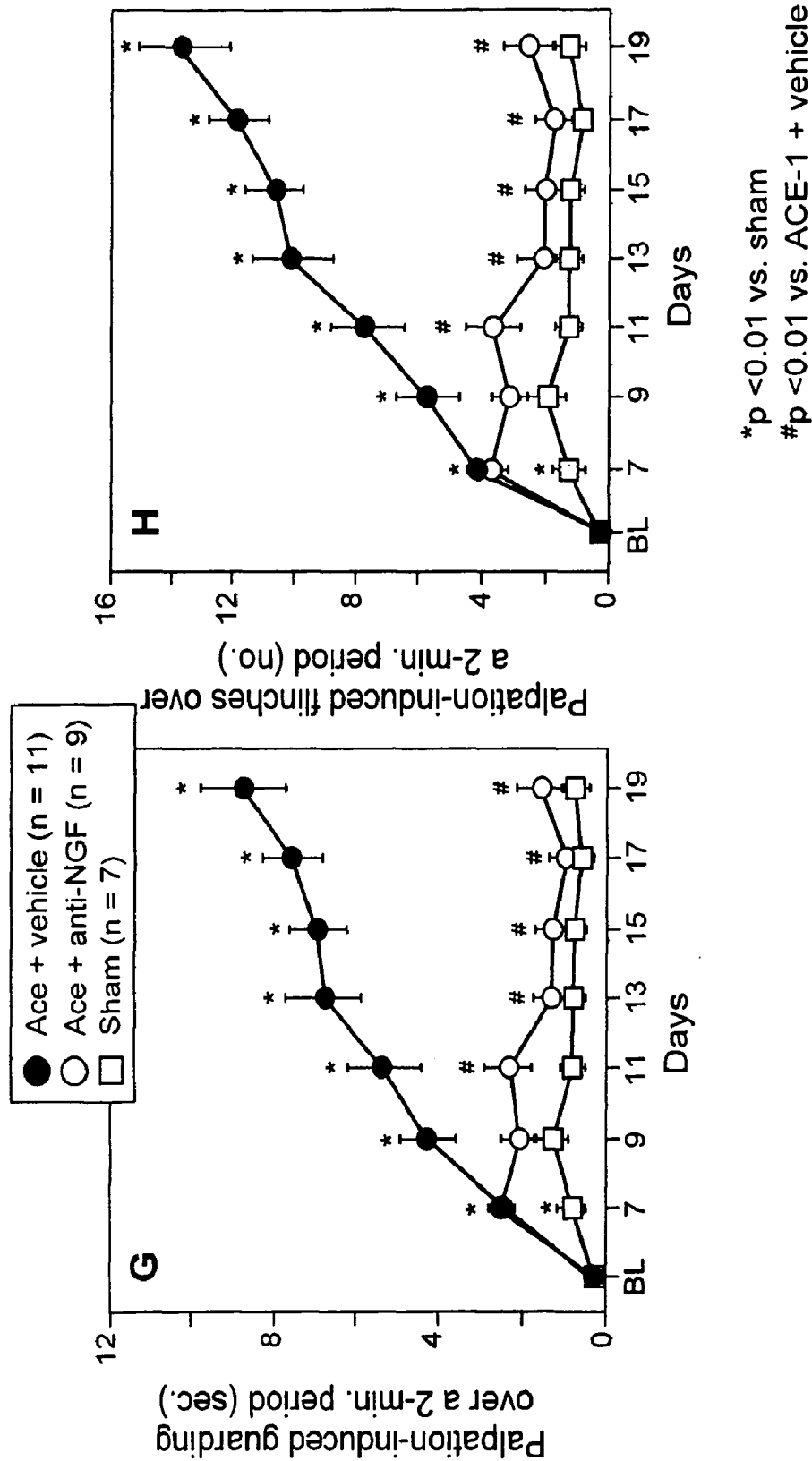

METHODS FOR TREATING BONE CANCER PAIN BY ADMINISTERING A NERVE GROWTH FACTOR ANTAGONIST

CROSS-REFERENCE TO RELATED APPLICATIONS

This application claims the priority benefit of provisional patent applications U.S. Ser. Nos. 60/620,654, filed Oct. 19, 2004, and 60/560,781, filed Apr. 7, 2004, all of which are incorporated herein in their entirety by reference.

STATEMENT REGARDING FEDERALLY SPONSORED RESEARCH OR DEVELOPMENT

This invention was made with U.S. Government support under National Institutes of Health grants 5R37-NS23970-16, 5R01-DA11986-05 and 1R01-NS048021-01A1. The U.S. Government may have certain rights in this invention.

FIELD OF THE INVENTION

The present invention relates to the use of a Nerve Growth Factor (NGF) antagonist for the prevention, amelioration, or treatment of bone cancer pain.

BACKGROUND OF THE INVENTION

Nerve growth factor (NGF) was the first neurotrophin to be identified, and its role in the development and survival of both peripheral and central neurons has been well characterized. NGF has been shown to be a critical survival and maintenance factor in the development of peripheral sympathetic and embryonic sensory neurons and of basal forebrain cholinergic neurons (Smeyne, et al., *Nature* 368:246–249 (1994); Crowley, et al., *Cell* 76:1001–1011 (1994)). NGF upregulates expression of neuropeptides in sensory neurons (Lindsay, et al., *Nature* 337:362–364 (1989)), and its activity is mediated through two different membrane-bound receptors, the TrkA tyrosine kinase receptor and the p75 receptor which is structurally related to other members of the tumor necrosis factor receptor family (Chao, et al., *Science* 232:518–521 (1986)).

In addition to its effects in the nervous system, NGF has been increasingly implicated in processes outside of the nervous system. For example, NGF has been shown to enhance vascular permeability in the rat (Otten, et al., *Eur J Pharmacol.* 106:199–201 (1984)), enhance T- and B-cell immune responses (Otten, et al., *Proc. Natl. Acad. Sci. USA* 86:10059–10063 (1989)), induce lymphocyte differentiation and mast cell proliferation and cause the release of soluble biological signals from mast cells (Matsuda, et al., *Proc. Natl. Acad. Sci. USA* 85:6508–6512 (1988); Pearce, et al., *J. Physiol.* 372:379–393 (1986); Bischoff, et al., *Blood* 79:2662–2669 (1992); Horigome, et al., *J. Biol. Chem.* 268:14881–14887(1993)). Although exogenously added NGF has been shown to be capable of having all of these effects, it is important to note that it has only rarely been shown that endogenous NGF is important in any of these processes in vivo (Torcia, et al., *Cell.* 85(3):345–56 (1996)). Therefore, it is not clear what the effect might be, if any, of inhibiting the bioactivity of endogenous NGF.

NGF is produced by a number of cell types including mast cells (Leon, et al., *Proc. Natl. Acad. Sci. USA* 91:3739–3743 (1994)), B-lymphocytes (Torcia, et al., *Cell* 85:345–356 (1996), keratinocytes (Di Marco, et al., *J. Biol. Chem.* 268:22838–22846)), smooth muscle cells (Ueyama, et al., *J. Hypertens.* 11:1061–1065 (1993)), fibroblasts (Lindholm, et al., *Eur. J. Neurosci.* 2:795–801 (1990)), bronchial epithelial cells (Kassel, et al., *Clin, Exp. Allergy* 31:1432–40 (2001)), renal mesangial cells (Steiner, et al., *Am. J. Physiol.* 261:F792–798 (1991)) and skeletal muscle myotubes (Schwartz, et al., *J Photochem, Photobiol.* B 66:195–200 (2002)). NGF receptors have been found on a variety of cell types outside of the nervous system. For example, TrkA has been found on human monocytes, T- and B-lymphocytes and mast cells.

An association between increased NGF levels and a variety of inflammatory conditions has been observed in human patients as well as in several animal models. These include systemic lupus erythematosus (Bracci-Laudiero, et al., *Neuroreport* 4:563–565 (1993)), multiple sclerosis (Bracci-Laudiero, et al., *Neurosci. Lett.* 147:9–12 (1992)), psoriasis (Raychaudhuri, et al., *Acta Derm. l'enereol.* 78:84–86 (1998)), arthritis (Falcimi, et al., *Ann. Rheum. Dis.* 55:745–748 (1996)), interstitial cystitis (Okragly, et al., *J. Urology* 161:438–441 (1991)), asthma (Braun, et al., *Eur. J Immunol.* 28:3240–3251 (1998)), pancreatits, and prostatitis.

Consistently, an elevated level of NGF in peripheral tissues is associated with inflammation and has been observed in a number of forms of arthritis. The synovium of patients affected by rheumatoid arthritis expresses high levels of NGF while in non-inflamed synovium NGF has been reported to be undetectable (Aloe, et al., *Arch. Rheum.* 35:351–355 (1992)). Similar results were seen in rats with experimentally induced rheumatoid arthritis (Aloe, et al., *Clin. Exp. Rheumatol.* 10:203–204 (1992); Halliday et al., *Neurochem. Res.* 23:919–22 (1998)). Elevated levels of NGF have been reported in transgenic arthritic mice along with an increase in the number of mast cells. (Aloe, et al., *Int. J. Tissue Reactions-Exp. Clin. Aspects* 15:139–143 (1993)).

Treatment with exogenous NGF leads to an increase in pain and pain sensitivity. This is illustrated by the fact that injection of NGF leads to a significant increase in pain and pain sensitivity in both animal models (Lewin et al., *J. Neurosci.* 13:2136–2148 (1993); Amann, et al., *Pain* 64, 323–329 (1996); Andreev, et al., *Pain* 63, 109–115 (1995)) and human (Dyck, et al., *Neurology* 48, 501–505 (1997); Petty, et al., *Annals Neurol.* 36, 244–246 (1994)). NGF appears to act by multiple mechanisms including inducing the neurotrophin BDNF (Apfel, et al., *Mol. Cell. Neurosci.* 7(2), 134–142 (1996); Michael, et al., *J. Neurosci* 17, 8476–8490 (1997)) which in turn changes pain signal processing in the spinal cord (Hains, et al., *Neurosci Lett.* 320(3), 125–8 (2002); Miletic, et al., *Neurosci Lett.* 319(3), 137–40 (2002); Thompson, et al., *Proc Natl Acad Sci USA* 96(14), 7714–8 (1999)), inducing changes in the peripheral and central connections of the sensory neurons and other pain-transmitting neurons in the spinal cord (Lewin, et al., *European Journal of Neuroscience* 6, 1903–1912 (1994); Thompson, et al., *Pain* 62, 219–231 (1995)), inducing changes in axonal growth (Lindsay, R M, *J Neurosci.* 8(7), 2394–405 (1988)) inducing bradykinin receptor expression (Peterson et al., *Neuroscience* 83:161–168 (1998)), inducing changes in expression of genes responsible for nerve activation and conduction such as ion channels (Boettger, et al., *Brain* 125(Pt 2), 252–63 (2002); Kerr, et al., *Neuroreport* 12(14), 3077–8 (2001); Gould, et al., *Brain Res* 854(1–2), 19–29 (2000); Fjell et al., *J. Neurophysiol.* 81:803–810 (1999)), potentiating the pain related receptor TRPV1 (Chuang, et al., *Nature* 411 (6840), 957–62 (2001); Shu and Mendell, *Neurosci. Lett.* 274:159–162 (1999)) and causing pathological changes in muscles (Foster, et al., *J Pathol* 197(2), 245–55 (2002)). Many of these changes take place directly on the pain transmitting sensory neurons and apparently are not dependent on concomitant inflammation. In addition, there are at least two other cell types known to respond to NGF and that may be involved in changes of pain sensation or sensitivity. The first of these, the mast cell, has been reported to respond to NGF with degranulation (Yan, et al., *Clin. Sci.* (Lond) 80:565–569 (1991)) or, in other studies, to cause or increase mediator production or release in collaboration with other agents (Pearce and Thompson, *J. Physiol.* 372:379–393 (1986), Kawamoto, et al., *J. Immunol.* 168:6412–6419 (2002)). It has clearly been shown in the rat that NGF mediated pain responses are at least somewhat mediated by mast cells (Lewin, et al., *Eur. J. Neurosci.* 6:1903–1912 (1994), Woolf, et al., *J. Neurosci.* 16:2716–2723 (1996) although the potential relevance of this remains to be shown in humans. Primary sympathetic neurons are also known to respond to NGF and to also be involved in pain signaling (Aley, et al., *Neuroscience* 71:1083–1090 (1996)). It is clear that removing sympathetic innervation modifies the hyperalgesia normally seen in response to treatment with NGF (Woolf, et al., *J. Neurosci.* 16:2716–2723 (1996)).

The use of NGF antagonists, such as anti-NGF antibody, to treat various types of pain, has been described. See, e.g., U.S. Ser. Nos. 10/682,331, 10/682,638, 10/682,332 (Pub. No. 2004/0131615), Ser. No. 10/783,730 (Pub. No. 2004/0253244), Ser. No. 10/745,775 (Pub. No. 2004/0237124), Ser. No. 10/791,162; PCT/US03/32089 (WO 04/032870); PCT/US03/32083 (WO 2005/000194); PCT/US03/32113; PCT/US2004/05162 (WO 04/073653); PCT/US03/41252 (WO 04/058184).

Bone cancer pain may arise in humans from either primary bone tumors or more commonly from bone metastases (such as from breast, prostate, and lung carcinomas). See Luger et al., *Pain* 99:397–406 (2002). A mouse model of bone cancer pain has been developed, and this model of bone cancer pain mirrors the pain observed in humans with moderate to advanced bone cancer pain. See Luger et al., *Pain* 99:397–406 (2002); Clohisy et al., *Clinical Orthopaedics and Related Research* 415S:S279–S288 (2003); Schwei et al., *J. Neruosci.* 19:10886–10897 (1999); Honore et al., *Nat. Med.* 6: 521–529 (2000). Papers by Honore et al. and Schwei et al. state that the neurochemical signature of observed changes in the spinal cord and DRG of bone cancer bearing animals is unique and distinguishable from either typical inflammatory pain or typical neuropathic pain although there seem to be components of this biochemical signature similar to classic inflammatory and neuropathic pain states in this model. Honore et al. *Neuroscience* 98:585–598 (2000); Schwei et al. *J. Neruosci.* 19:10886–10897 (1999); Luger et al., *Pain* 99:397–406 (2002).

All references cited herein, including patent applications and publications, are incorporated by reference in their entirety.

BRIEF SUMMARY OF THE INVENTION

The present invention is based upon the discovery that antagonists of NGF, such as an anti-NGF antibody, are effective in treating bone cancer pain including cancer pain associated with bone metastasis. The treatment addresses one or more aspects of bone cancer pain including cancer pain associated with bone metastasis as described herein.

In one aspect, the invention features a method for preventing or treating bone cancer pain including cancer pain associated with bone metastasis (also termed "bone metastasis pain") by administering an antagonist of nerve growth factor (NGF). In some embodiments, the NGF antagonist is co-administered with an opioid analgesic. In some embodiments, the NGF antagonist is co-administered with an NSAID. In some embodiments, the NGF antagonist is co-administered with an opioid analgesic and an NSAID. In some embodiments, the NGF antagonist is not co-administered with an opioid analgesic. In some embodiments, the NGF antagonist is not co-administered with an NSAID.

In another aspect, the invention provides methods for reducing incidence of bone cancer pain including cancer pain associated with bone metastasis, ameliorating bone cancer pain including cancer pain associated with bone metastasis, palliating bone cancer pain including cancer pain associated with bone metastasis; and/or delaying the development or progression of bone cancer pain including cancer pain associated with bone metastasis in an individual, said methods comprising administering an effective amount of an NGF antagonist. In some embodiments, the NGF antagonist is co-administered with an opioid analgesic. In some embodiments, the NGF antagonist is co-administered with an NSAID. In some embodiments, the NGF antagonist is co-administered with an opioid analgesic and an NSAID. In some embodiments, the NGF antagonist is not co-administered with an opioid analgesic. In some embodiments, the NGF antagonist is not co-administered with an NSAID.

In some embodiments, the bone cancer pain is from cancer originated in bone. In some embodiments, the bone cancer pain is from osteosarcoma. In some embodiments, the bone cancer pain is from cancer metastasized to bone. In some embodiments, the bone metastasis is prostate cancer metastasized to bone. In some embodiments, the bone metastasis is breast cancer metastasized to bone. In some embodiments, the bone metastasis is lung cancer metastasized to bone. In some embodiments, the bone metastasis is sarcoma metastasized to bone. In some embodiments, the bone metastasis is kidney cancer metastasized to bone. In some embodiments, the bone metastasis is multiple myeloma metastasized to bone. In some embodiments, the cancer pain treated is mild to moderate. In some embodiments, the cancer pain treated is moderate to severe. In some embodiments, the cancer pain treated is severe.

An NGF antagonist suitable for use in the methods of the invention is any agent that can directly or indirectly result in decreased NGF biological activity. In some embodiments, an NGF antagonist (e.g., an antibody) binds (physically interacts with) NGF, binds to an NGF receptor (such as trkA receptor and/or p75), and/or reduces (impedes and/or blocks) downstream NGF receptor signaling (e.g., inhibitors of kinase signaling). Accordingly, in some embodiments, an NGF antagonist binds (physically interacts with) NGF. In other embodiment, an NGF antagonist binds to an NGF receptor (such as TrkA receptor and/or p75). In other embodiments, an NGF antagonist reduces (impedes and/or blocks) downstream NGF receptor signaling (e.g., inhibitors of kinase signaling). In other embodiments, an NGF antagonist inhibits (reduces) NGF synthesis and/or release. In another embodiment, the NGF antagonist is a TrkA immunoadhesin. In some embodiments, the NGF antagonist binds NGF (such as hNGF) and does not significantly bind to related neurotrophins, such as NT-3, NT4/5, and/or BDNF. In some embodiments, the NGF antagonist is selected from any one or more of the following: an anti-NGF antibody, an anti-sense molecule directed to an NGF (including an anti-sense molecule directed to a nucleic acid encoding NGF), an anti-sense molecule directed toward an NGF receptor (such as trkA and/or p75) (including an anti-sense molecule directed to a nucleic acid encoding an NGF receptor), an NGF inhibitory compound, an NGF structural analog, a dominant-negative mutation of a TrkA and/or p75 receptor that binds an NGF, an anti-TrkA antibody, an anti-p75 antibody, and a kinase inhibitor. In another embodiment, the NGF antagonist is an anti-NGF antibody. In still other embodiments, the anti-NGF antibody is humanized (such as antibody E3 described herein). In some embodiments, the anti-NGF antibody is antibody E3 (as described herein). In other embodiments, the anti-NGF antibody comprises one or more CDR(s) of antibody E3 (such as one, two, three, four, five, or, in some embodiments, all six CDRs from E3). In other embodiments, the antibody is human. In some embodiments, the antibody comprises three CDRs from the heavy chain of E3. In some embodiments, the antibody comprises three CDRs from the light chain of E3. In still other embodiments, the anti-NGF antibody comprises the amino acid sequence of the heavy chain variable region shown in Table 1 (SEQ ID NO:1). In still other embodiments, the anti-NGF antibody comprises the amino acid sequence of the light chain variable region shown in Table 2 (SEQ ID NO:2) In still other embodiments, the anti-NGF antibody comprises the amino acid sequence of the heavy chain variable region shown in Table 1 (SEQ ID NO:1) and the amino acid sequence of the light chain variable region shown in Table 2 (SEQ ID NO:2). In still other embodiments, the antibody comprises a modified constant region, such as a constant region that is immunologically inert, e.g., does not trigger complement mediated lysis, or does not stimulate antibody-dependent cell mediated cytotoxicity (ADCC). In other embodiments, the constant region is modified as described in Eur. J. Immunol. (1999) 29:2613–2624; PCT Application No. PCT/GB99/01441; and/or UK Patent Application No. 9809951.8.

In some embodiments, the NGF antagonist binds to NGF. In still other embodiments, the NGF antagonist is an antibody that binds specifically to NGF (such as human NGF). In still other embodiments, the antibody binds essentially the same NGF epitope 6 as an antibody selected from any one or more of the following mouse monoclonal antibodies: Mab 911, MAb 912 and MAb 938 (See Hongo, et al., Hybridoma 19:215–227 (2000)). In some embodiments, the NGF antagonist binds to the trkA receptor. The NGF antagonist may be an anti-human NGF (anti-hNGF) monoclonal antibody that is capable of binding hNGF and effectively inhibiting the binding of hNGF to human TrkA (hTrkA) and/or effectively inhibiting activation of human TrkA receptor.

The binding affinity of an anti-NGF antibody to NGF (such as hNGF) can be about 0.10 to about 1.0 nM, about 0.10 nM to about 0.80 nM, about 0.15 to about 0.75 nM and about 0.18 to about 0.72 nM. In one embodiment, the binding affinity is between about 2 pM and 22 pM. In some embodiment, the binding affinity is about 10 nM. In other embodiments, the binding affinity is less than about 10 nM. In other embodiments, the binding affinity is about 0.1 nM or about 0.07 nM. In other embodiments, the binding affinity is less than about 0.1 nM, or less than about 0.07 nM. In other embodiments, the binding affinity is any of about 100 nM, about 50 nM, about 10 nM, about 1 nM, about 500 pM, about 100 pM, or about 50 pM to any of about 2 pM, about 5 pM, about 10 pM, about 15 pM, about 20 pM, or about 40 pM. In some embodiments, the binding affinity is any of about 100 nM, about 50 nM, about 10 nM, about 1 nM, about 500 pM, about 100 pM, or about 50 pM, or less than about 50 pM. In some embodiments, the binding affinity is less than any of about 100 nM, about 50 nM, about 10 nM, about 1 nM, about 500 pM, about 100 pM, or about 50 pM. In still other embodiments, the binding affinity is about 2 pM, about 5 pM, about 10 pM, about 15 pM, about 20 pM, about 40 pM, or greater than about 40 pM. As is well known in the art, binding affinity can be expressed as $K_D$, or dissociation constant, and an increased binding affinity corresponds to a decreased $K_D$. The binding affinity of anti-NGF mouse monoclonal antibody 911 (Hongo et al., Hybridoma 19:215–227 (2000)) to human NGF is about 10 nM, and the binding affinity of humanized anti-NGF antibody E3 (described herein) to human NGF is about 0.07 nM. Binding affinities for antibody 911 and E3 were measured using their Fab fragments.

The NGF antagonist may be administered prior to, during, and/or after an individual has been diagnosed with bone cancer or cancer has metastasized to bone. Administration of an NGF antagonist can be by any means known in the art, including: orally, intravenously, subcutaneously, intraarterially, intramuscularly, intracardially, intraspinally, intrathoracically, intraperitoneally, intraventricularly, sublingually, and/or transdermally. In some embodiments, the NGF antagonist is an anti-NGF antibody, and administration is by one or more of the following means: intravenously, subcutaneously, via inhalation, intraarterially, intramuscularly, intracardially, intraventricularly, and intraperitoneally. Administration may be systemic, e.g. intravenously, or localized.

In some embodiments, the NGF antagonist is administered in a dose of about 0.1 to 10 mg/kg of body weight, and in other embodiments, the NGF antagonist is administered in a dose of about 0.3 to 2.0 mg/kg of body weight.

In another aspect, the invention features a composition for treating and/or preventing bone cancer pain including cancer pain associated with bone metastasis comprising an effective amount of a nerve growth factor (NGF) antagonist, in combination with one or more pharmaceutically acceptable excipients. In some embodiments, the NGF antagonist is co-administered with an opioid analgesic. In some embodiments, the NGF antagonist is co-administered with an NSAID. In some embodiments, the NGF antagonist is not co-administered with an opioid analgesic or an NSAID. In some embodiments, the NGF antagonist is an antibody that specifically binds to the NGF molecule. In other embodiments, the NGF antagonist is any antagonist described herein.

In another aspect, the invention features a kit for use in any of the methods described herein. In some embodiments, the kit comprises any of the NGF antagonists described herein, in combination with a pharmaceutically acceptable carrier. In other embodiments, the kit further comprises instructions for use of the NGF antagonist in any of the methods described herein.

BRIEF DESCRIPTION OF THE DRAWINGS

FIGS. 4a, 4b, and 4c are radiographs showing presence or absence of bone destruction. FIGS. 4d, 4e, and 4f are photographs showing immunostaining with anti-GFP antibody. Scale bars: 1 mm.

FIGS. 7a and 7b show thermal sensitivity (a, n=8 for naïve+vehicle, n=8 for naïve+anti-NGF) measured by latency of paw withdrawal to a thermal stimulus and mechanical sensitivity (b, n=8 for naïve+vehicle, n=8 for naïve+anti-NGF) measured by 50% threshold of mechanical stimulation of anti-NGF treatment (10 mg/kg, i.p., every 5 days) in naïve mice. FIGS. 7c and 7d show ongoing pain behaviors evaluated by measuring spontaneous guarding (c) over a 2-minute observation period, and movement-evoked pain assessed by measuring the time spent guarding (d) over a 2-minute observation period following normally non-noxious palpation of the distal femur. Values of spontaneous guarding (c) and palpation-induced guarding (d) for naïve, sham and vehicle treated, sarcoma injected and vehicle treated, sarcoma injected and morphine (n=8, 10 mg/kg i.p. administered 15 min prior to testing) treated, sarcoma injected and morphine (n=8, 30 mg/kg i.p. administered 15 min prior to testing) treated, and sarcoma injected and anti-NGF antibody (n=8, 10 mg/kg, every 5 days, i.p. administered from 6 days to 14 days post-tumor injection) treated mice are shown. Error bars represent S.E.M. "#" indicates P<0.05 vs. sham+vehicle (n=8); "*" indicates P<0.05 vs. sarcoma+vehicle; and "+" indicates P<0.05 vs. sarcoma+morphine.

FIGS. 8a and 8b show immunofluorescent staining of activating transcription factor-3 (ATF-3) in the ipsilateral L2 DRG of tumor-bearing animals vehicle treated (a, n=8) and anti-NGF antibody treated (b, n=8) fourteen days post tumor implantation. Bottom panel shows immunofluorescent staining of CD-68 indicating the density of activated and infiltrating macrophages around injured sensory neurons within the ipsilateral DRG of tumor-bearing animals vehicle treated (c, n=7) and anti-NGF antibody treated (d, n=7). Scale bars a–d=5 μm.

FIGS. 9A and 9B show immunostaining of dynorphin in the dorsal horn of the spinal cord of sarcoma injected and vehicle treated mice (A, n=9) and sarcoma injected and anti-NGF antibody treated mice (B, n=4). FIGS. 9C and 9D show representative confocal images of c-Fos expressing neurons of the spinal cord in sarcoma injected and vehicle treated mice (C, n=4) and sarcoma injected and anti-NGF antibody treated mice (D, n=4) following a normally non-noxious palpation of tumor-bearing limbs. Scale bar: 150 μm for A and B; 200 μm for C and D.

FIG. 10 shows graphs demonstrating that anti-NGF therapy attenuated prostate tumor-induced bone cancer pain. Anti-NGF treatment (10 mg/kg, i.p, given on days 7, 12, and 17 post tumor-injection) attenuated ongoing bone cancer pain behaviors beginning on day 7 post-tumor injection throughout disease progression. The time spent guarding and number of spontaneous flinches in ACE-1 injected femurs over a 2-minute observation period were used as measures of ongoing pain (A, B). Anti-NGF (filled square) significantly reduced ongoing pain behaviors in tumor-injected animals as compared to ACE-1+vehicle (open square), and was reduced to close to sham levels at day 9 for all parameters (circle). Both guarding and flinching in the sham+vehicle animals were significantly different from ACE-1+vehicle animals across disease progression. Anti-NGF treatment had no effect on basal thermal or mechanical responses as measured by latency of paw withdrawal to a thermal stimulus or increase in threshold of mechanical stimulation (C, D). Anti-NGF treatment produced a greater reduction in ongoing pain behaviors at day 19 than 10 mg/kg or 30 mg/kg morphine (i.p., 15 min prior to testing) (E, F). Movement-evoked pain was measured by quantification of time spent guarding and the number of flinches over a 2-minute observation period following a normally non-noxious palpation of the ACE-1-injected femur (G, H). Error bars represent S.E.M. For FIG. 10A–F, "#" indicates P<0.05 vs. sham+vehicle; "*" indicates P<0.05 vs. ACE-1+vehicle; and "+" indicates P<0.05 vs. ACE-1+morphine. For FIGS. 10G and 10H, "*" indicates P<0.01 vs. sham; and "#" indicates P<0.01 vs. ACE-1+vehicle.

DETAILED DESCRIPTION OF THE INVENTION

Figure 1:
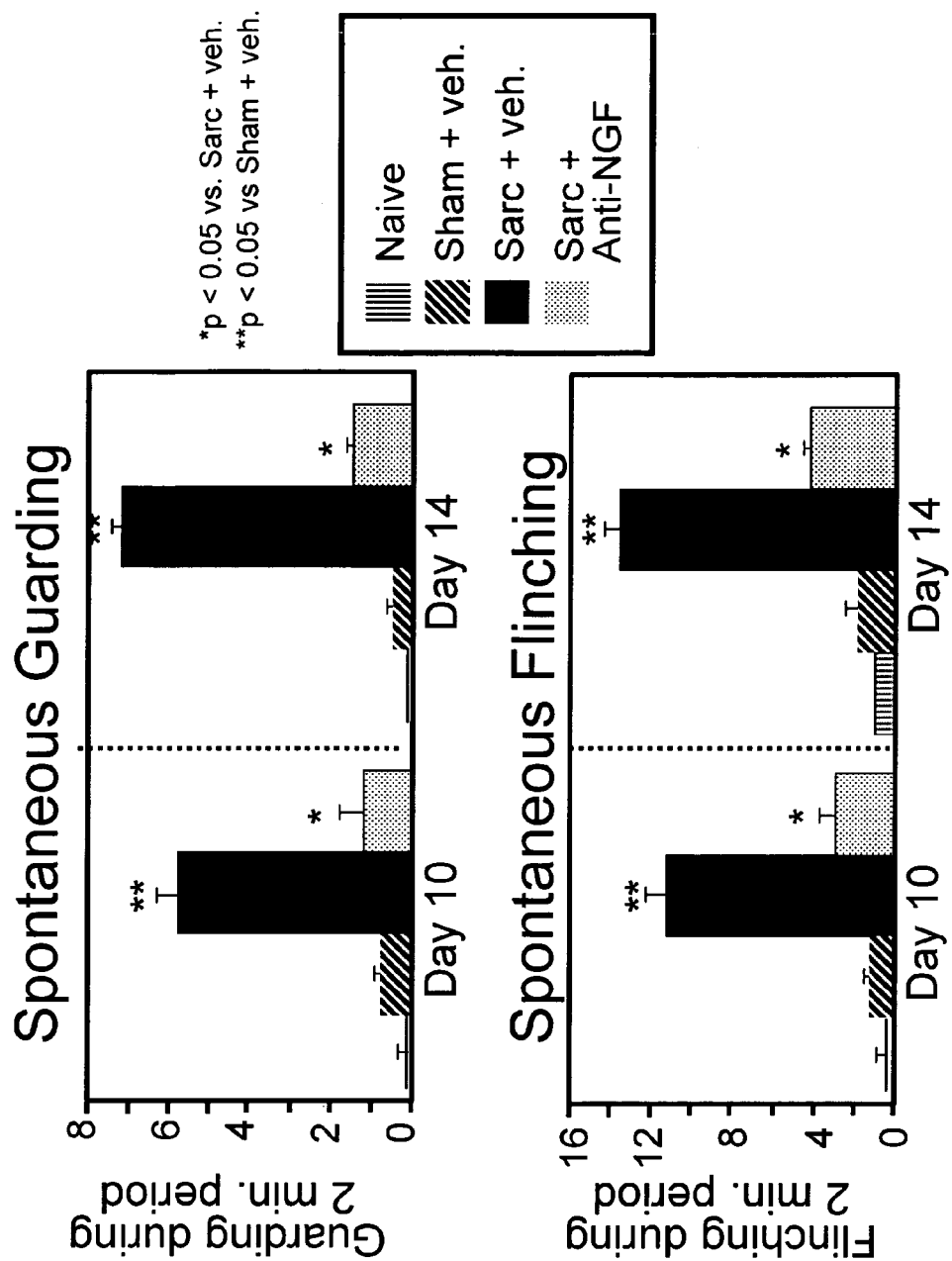
FIG. 1 is a graph depicting ongoing pain as assessed by spontaneous guarding and spontaneous flinching during a 2-min observation period on day 10 and day 14 post-sarcoma injection. "Naive" refers to animals without any injection. "Sham+veh." refers to animals injected with α-minimum essential media into the femur marrow cavity and later injected with saline. "Sarc+veh." refers to animals injected with sarcoma into the femur marrow cavity and later injected with saline. "Sarc+Anti-NGF" refers to animals injected with sarcoma into the femur marrow cavity and later injected with anti-NGF antibody 911.

The present invention is based on the discovery that in vivo administration of a therapeutically effective amount of an NGF antagonist such as anti-NGF monoclonal antibody may be used to treat bone cancer pain including cancer pain associated with bone metastasis. The invention is based on observations in a mouse bone cancer model that administration of anti-NGF antagonist antibody is strikingly effective in reducing both ongoing and movement-evoked bone cancer pain.

The invention features methods of preventing or treating bone cancer pain including cancer pain associated with bone metastasis in an individual (both human and non-human) by administering an effective amount of an NGF antagonist such as an anti-NGF antibody, for instance an anti-human NGF (anti-hNGF) monoclonal antibody. In some embodiments, the NGF antagonist is co-administered with an opioid analgesic. In some embodiments, the NGF antagonist is co-administered with an NSAID. In some embodiments, the NGF antagonist is not co-administered with an opioid analgesic. In some embodiments, the NGF antagonist is not co-administered with an NSAID.

In another aspect, the invention provides methods for ameliorating, delaying the development of and/or preventing the progression of bone cancer pain including cancer pain associated with bone metastasis comprising administering an effective amount of an NGF antagonist to an individual. In some embodiments, the NGF antagonist is co-administered with an opioid analgesic. In some embodiments, the NGF antagonist is co-administered with an NSAID. In some embodiments, the NGF antagonist is not co-administered with an opioid analgesic. In some embodiments, the NGF antagonist is not co-administered with an NSAID.

The invention also features compositions and kits for treating bone cancer pain including cancer pain associated with bone metastasis comprising an NGF antagonist such as an anti-NGF antibody, for instance an anti-NGF monoclonal antibody, for use in any of the methods provided herein. In some embodiments, the anti-NGF antibody is capable of effectively inhibiting NGF binding to its TrkA and/or p75 receptor(s) and/or of effectively inhibiting NGF from activating its TrkA and/or p75 receptor(s).

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook, et al., 1989) Cold Spring Harbor Press; *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993–8) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel, et al., eds., 1987); *PCR: The Polymerase Chain Reaction*, (Mullis, et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: a practical approach* (D. Catty., ed., IRL Press, 1988–1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995).

Definitions

An "antibody" (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')2, Fv), single chain (ScFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

A "monoclonal antibody" refers to a homogeneous antibody population wherein the monoclonal antibody is comprised of amino acids (naturally occurring and non-naturally occurring) that are involved in the selective binding of an antigen. A population of monoclonal antibodies is highly specific, being directed against a single antigenic site. The term "monoclonal antibody" encompasses not only intact monoclonal antibodies and full-length monoclonal antibodies, but also fragments thereof (such as Fab, Fab', F(ab')2, Fv), single chain (ScFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.).

As used herein, the term "nerve growth factor" and "NGF" refers to nerve growth factor and variants thereof that retain at least part of the activity of NGF. As used herein, NGF includes all mammalian species of native sequence NGF, including human, canine, feline, equine, or bovine.

"NGF receptor" refers to a polypeptide that is bound by or activated by NGF. NGF receptors include the TrkA receptor and the p75 receptor of any mammalian species, including, but are not limited to, human, canine, feline, equine, primate, or bovine.

An "NGF antagonist" refers to any molecule that blocks, suppresses or reduces (including significantly) NGF biological activity, including downstream pathways mediated by NGF signaling, such as receptor binding and/or elicitation of a cellular response to NGF. The term "antagonist" implies no specific mechanism of biological action whatsoever, and is deemed to expressly include and encompass all possible pharmacological, physiological, and biochemical interactions with NGF whether direct or indirect, or whether interacting with NGF, its receptor, or through another mechanism, and its consequences which can be achieved by a variety of different, and chemically divergent, compositions. Exemplary NGF antagonists include, but are not limited to, an anti-NGF antibody, an anti-sense molecule directed to an NGF (including an anti-sense molecule directed to a nucleic acid encoding NGF), an NGF inhibitory compound, an NGF structural analog, a dominant-negative mutation of a TrkA receptor that binds an NGF, a TrkA immunoadhesin, an anti-TrkA antibody, an anti-p75 antibody, and a kinase inhibitor. For purpose of the present invention, it will be explicitly understood that the term "antagonist" encompass all the previously identified terms, titles, and functional states and characteristics whereby the NGF itself, an NGF biological activity (including but not limited to its ability to mediate any aspect of cancer pain associated with bone metastasis), or the consequences of the biological activity, are substantially nullified, decreased, or neutralized in any meaningful degree. In some embodiments, an NGF antagonist (e.g., an antibody) binds (physically interact with) NGF, binds to an NGF receptor (such as trkA receptor and/or p75 receptor), reduces (impedes and/or blocks) downstream NGF receptor signaling, and/or inhibits (reduces) NGF synthesis, production or release. In other embodiments, an NGF antagonist binds NGF and prevents TrkA receptor dimerization and/or TrkA autophosphorylation. In other embodiments, an NGF antagonist inhibits or reduces NGF synthesis and/or production (release). Examples of types of NGF antagonists are provided herein.

As used herein, an "anti-NGF antibody" refers to an antibody which is able to bind to NGF and inhibit NGF biological activity and/or downstream pathway(s) mediated by NGF signaling.

A "TrkA immunoadhesin" refers to a soluble chimeric molecule comprising a fragment of a TrkA receptor, for example, the extracellular domain of a TrkA receptor and an immunoglobulin sequence, which retains the binding specificity of the TrkA receptor.

"Biological activity" of NGF generally refers to the ability to bind NGF receptors and/or activate NGF receptor signaling pathways. Without limitation, a biological activity includes any one or more of the following: the ability to bind an NGF receptor (such as p75 and/or TrkA); the ability to promote TrkA receptor dimerization and/or autophosphorylation; the ability to activate an NGF receptor signaling pathway; the ability to promote cell differentiation, proliferation, survival, growth, migration and other changes in cell physiology, including (in the case of neurons, including peripheral and central neuron) change in neuronal morphology, synaptogenesis, synaptic function, neurotransmitter and/or neuropeptide release and regeneration following damage; and the ability to mediate cancer pain associated with bone metastasis.

As used herein, "treatment" is an approach for obtaining beneficial or desired clinical results. For purposes of this invention, beneficial or desired clinical results include, but are not limited to, one or more of the following: improvement in any aspect of the pain including lessening severity, alleviation of one or more symptoms associated with bone cancer pain (e.g., cancer pain associated with bone metastasis) including any aspect of bone cancer pain (such as shortening duration of pain, and/or reduction of pain sensitivity or sensation).

An "effective amount" is an amount sufficient to effect beneficial or desired clinical results including alleviation or reduction in pain. For purposes of this invention, an effective amount of an NGF antagonist is an amount sufficient to treat, ameliorate, reduce the intensity of or prevent bone cancer pain including cancer pain associated with bone metastasis. In some embodiments, the "effective amount" may reduce the pain of ongoing pain and/or breakthrough pain (including ambulatory pain and touch-evoked pain), and it may be administered before, during, and/or after cancer has metastasized to bone. In some embodiment, the "effective amount" is an amount sufficient to delay development of bone cancer pain including cancer pain associated with bone metastasis.

"Reducing incidence" of pain means any of reducing severity (which can include reducing need for and/or amount of (e.g., exposure to) other drugs and/or therapies generally used for these conditions), duration, and/or frequency (including, for example, delaying or increasing time to bone cancer pain including cancer pain associated with bone metastasis in an individual). As is understood by those skilled in the art, individuals may vary in terms of their response to treatment, and, as such, for example, a "method of reducing incidence of bone cancer pain including cancer pain associated with bone metastasis in an individual" reflects administering the NGF antagonist described herein based on a reasonable expectation that such administration may likely cause such a reduction in incidence in that particular individual.

"Ameliorating" bone cancer pain (such as cancer pain associated with bone metastasis) or one or more symptoms of bone cancer pain means a lessening or improvement of one or more symptoms of a bone cancer pain as compared to not administering an NGF antagonist. "Ameliorating" also includes shortening or reduction in duration of a symptom.

"Palliating" bone cancer pain (such as cancer pain associated with bone metastasis) or one or more symptoms of a bone cancer pain means lessening the extent of one or more undesirable clinical manifestations of bone cancer pain in an individual or population of individuals treated with an NGF antagonist in accordance with the invention.

As used therein, "delaying" the development of bone cancer pain including cancer pain associated with bone metastasis means to defer, hinder, slow, retard, stabilize, and/or postpone progression of bone cancer pain including cancer pain associated with bone metastasis. This delay can be of varying lengths of time, depending on the history of the disease and/or individuals being treated. As is evident to one skilled in the art, a sufficient or significant delay can, in effect, encompass prevention, in that the individual does not develop bone cancer pain including cancer pain associated with bone metastasis. A method that "delays" development of the symptom is a method that reduces probability of developing the symptom in a given time frame and/or reduces extent of the symptoms in a given time frame, when compared to not using the method. Such comparisons are typically based on clinical studies, using a number of subjects sufficient to give a statistically significant result.

"Development" or "progression" of bone cancer pain including cancer pain associated with bone metastasis means initial manifestations and/or ensuing progression of the disorder. Development of bone cancer pain including cancer pain associated with bone metastasis can be detectable and assessed using standard clinical techniques as well known in the art. However, development also refers to progression that may be undetectable. For purpose of this invention, development or progression refers to the biological course of the symptoms. "Development" includes occurrence, recurrence, and onset. As used herein "onset" or "occurrence" of bone cancer pain (such as cancer pain associated with bone metastasis) includes initial onset and/or recurrence.

As used herein, "co-administration" includes simultaneous administration and/or administration at different times. Co-administration also encompasses administration as a co-formulation (i.e., the NGF antagonist and an agent are present in the same composition) or administration as separate compositions. As used herein, co-administration is meant to encompass any circumstance wherein an agent and NGF antagonist are administered to an individual, which can occur simultaneously and/or separately. As further discussed herein, it is understood that the NGF antagonist and an agent can be administered at different dosing frequencies or intervals. For example, an anti-NGF antibody can be administered weekly, while the agent can be administered more frequently. It is understood that the NGF antagonist and the agent can be administered using the same route of administration or different routes of administration.

The term "opioid analgesic" refers to all drugs, natural or synthetic, with morphine-like actions. The synthetic and semi-synthetic opioid analgesics are derivatives of five chemical classes of compound: phenanthrenes; phenylheptylamines; phenylpiperidines; morphinans; and benzomorphans, all of which are within the scope of the term. Exemplary opioid analgesics include codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine or pharmaceutically acceptable salts thereof.

The term "NSAID" refers to a non-steroidal anti-inflammatory compound. NSAIDs are categorized by virtue of their ability to inhibit cyclooxygenase. Cyclooxygenase 1 and cyclooxygenase 2 are two major isoforms of cyclooxygenase and most standard NSAIDs are mixed inhibitors of the two isoforms. Most standard NSAIDs fall within one of the following five structural categories: (1) propionic acid derivatives, such as ibuprofen, naproxen, naprosyn, diclofenac, and ketoprofen; (2) acetic acid derivatives, such as tolmetin and slindac; (3) fenamic acid derivatives, such as mefenamic acid and meclofenamic acid; (4) biphenylcarboxylic acid derivatives, such as diflunisal and flufenisal; and (5) oxicams, such as piroxim, sudoxicam, and isoxicam.

Another class of NSAID has been described which selectively inhibit cyclooxygenase 2. Cox-2 inhibitors have been described, e.g., in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311, all of which are hereby incorporated by reference. Certain exemplary COX-2 inhibitors include celecoxib (SC-58635), DUP-697, flosulide (CGP-28238), meloxicam, 6-methoxy-2 naphthylacetic acid (6-MNA), rofecoxib, MK-966, nabumetone (prodrug for 6-MNA), nimesulide, NS-398, SC-5766, SC-58215, T-614; or combinations thereof.

An "individual" is a mammal, more preferably a human. Mammals include, but are not limited to, farm animals, sport animals, pets, primates, horses, dogs, cats, mice and rats.

Methods of the Invention

With respect to all methods described herein, reference to an NGF antagonist also includes compositions comprising one or more of these agents. These compositions may further comprise suitable excipients, such as pharmaceutically acceptable excipients (carriers) including buffers, which are well known in the art. The present invention can be used alone or in combination with other conventional methods of treatment.

Methods for Preventing or Treating Bone Cancer Pain Including Cancer Pain associated with Bone Metastasis The present invention is useful for treating, delaying development of and/or preventing bone cancer pain including cancer pain associated with bone metastasis in an individual, both human and non-human. The quality of life in individuals having bone cancer may be improved.

Cancer metastasis to bone may be associated with a net bone formation or a net bone destruction. In some embodiments, the method of the invention is used for treating bone cancer pain associated with a net bone formation (osteoblastic activity), such as for treating pain of prostate cancer metastasis to bone. In some embodiments, the method of the invention is used for treating bone cancer pain associated with a net bone destruction (osteolytic activity), such as for treating pain of sarcoma metastasis to bone.

Accordingly, in one aspect, the invention provides methods of treating bone cancer pain including cancer pain associated with bone metastasis in an individual comprising administering an effective amount of an NGF antagonist, such as an anti-NGF antibody. In some embodiments, the NGF antagonist is co-administered with an opioid analgesic. In some embodiments, the NGF antagonist is co-administered with an NSAID. In some embodiments, the NGF antagonist is co-administered with an opioid analgesic and an NSAID. In some embodiments, the amount of the opioid analgesic and/or the NSAID administered for pain alleviation are reduced, comparing to the amount administered in the absence of the NGF antagonist. Adverse effects due to the opioid analgesic and/or the NSAID may be reduced or eliminated when they are co-administered with the NGF antagonist. In some embodiments, the NGF antagonist is not co-administered with an opioid analgesic. In other embodiments, the NGF antagonist is not co-administered with an NSAID. In other embodiments, the NGF antagonist is not co-administered with an opioid analgesic and/or an NSAID.

In another aspect, the invention provides methods of preventing, ameliorating and/or preventing the development or progression of bone cancer pain including cancer pain associated with bone metastasis. In some embodiments, the NGF antagonist is co-administered with an opioid analgesic. In some embodiments, the NGF antagonist is co-administered with an NSAID. In some embodiments, the NGF antagonist is co-administered with an opioid analgesic and an NSAID. In some embodiments, the NGF antagonist is not co-administered with an opioid analgesic. In other embodiments, the NGF antagonist is not co-administered with an NSAID. In other embodiments, the NGF antagonist is not co-administered with an opioid analgesic and/or an NSAID.

It is appreciated that although reference is generally made herein to treating or preventing bone cancer pain such as cancer pain associated with bone metastasis, the NGF antagonist can be administered before an event or condition(s) with an increased risk of bone cancer pain.

An NGF antagonist may be administered in conjunction with other therapies for bone cancer, such as radiation, and chemotherapy. The NGF antagonist may also be administered in conjunction with other analgesics used for bone cancer pain. Examples of such analgesics are bisphosphonates (e.g., Alendronate), gabapentin, and radiation. The amount of these analgesics administered for bone cancer pain alleviation may be reduced, comparing to the amount administered in the absence of the NGF antagonist. Adverse effects due to these analgesics may be reduced or eliminated when they are co-administered with the NGF antagonist.

Diagnosis or assessment of pain is well-established in the art. Assessment may be performed based on objective measure, such as observation of behavior such as reaction to stimuli, facial expressions and the like. Assessment may also be based on subjective measures, such as patient characterization of pain using various pain scales. See, e.g., Katz et al, Surg Clin North Am. (1999) 79 (2):231–52; Caraceni et al. J Pain Symptom Manage (2002) 23(3):239–55.

NGF Antagonists

The methods of the invention use an NGF antagonist, which refers to any molecule that blocks, suppresses or reduces (including significantly) NGF biological activity, including downstream pathways mediated by NGF signaling, such as receptor binding and/or elicitation of a cellular response to NGF. The term "antagonist" implies no specific mechanism of biological action whatsoever, and is deemed to expressly include and encompass all possible pharmacological, physiological, and biochemical interactions with NGF and its consequences which can be achieved by a variety of different, and chemically divergent, compositions. Exemplary NGF antagonists include, but are not limited to, an anti-NGF antibody, an anti-sense molecule directed to NGF (including an anti-sense molecule directed to a nucleic acid encoding NGF), an anti-sense molecule directed to an NGF receptor (such as TrkA receptor and/or p75 receptor) (including an anti-sense molecule directed to a nucleic acid encoding TrkA and/or p75), an NGF inhibitory compound, an NGF structural analog, a dominant-negative mutation of a TrkA receptor that binds an NGF, a TrkA immunoadhesin, an anti-TrkA antibody, a dominant-negative mutation of a p75 receptor that binds an NGF, an anti-p75 antibody, and a kinase inhibitor. For purpose of the present invention, it will be explicitly understood that the term "antagonist" encompasses all the previously identified terms, titles, and functional states and characteristics whereby the NGF itself, an NGF biological activity (including but not limited to its ability to mediate any aspect of cancer pain associated with bone metastasis), or the consequences of the biological activity, are substantially nullified, decreased, or neutralized in any meaningful degree. In some embodiments, an NGF antagonist (e.g., an antibody) binds (physically interact with) NGF, binds to an NGF receptor (such as TrkA receptor and/or p75 receptor), and/or reduces (impedes and/or blocks) downstream NGF receptor signaling. Accordingly, in some embodiments, an NGF antagonist binds (physically interacts with) NGF. In some embodiments, the NGF antagonist is a polypeptide which binds to NGF. In some embodiments, the NGF antagonist is a peptide or a modified peptide (such as NGF binding peptide fused to a Fc domain) described in PCT WO 2004/026329. In other embodiment, an NGF antagonist binds to an NGF receptor (such as trkA receptor or p75). In other embodiments, an NGF antagonist reduces (impedes and/or blocks) downstream NGF receptor signaling (e.g., inhibitors of kinase signaling and inhibitors of downstream signaling cascade). In other embodiments, an NGF antagonist inhibits (reduces) NGF synthesis and/or release. In another embodiment, the NGF antagonist is an NGF antagonist that is not a TrkA immunoadhesin (i.e., is other than a TrkA immunoadhesin). In another embodiment, the NGF antagonist is other than an anti-NGF antibody. In other embodiment, the NGF antagonist is other than a TrkA immunoadhesin and other than an anti-NGF antibody. In some embodiment, the NGF antagonist binds NGF (such as hNGF) and does not significantly bind to related neurotrophins, such as NT-3, NT4/5, and/or BDNF. In some embodiments, the NGF antagonist is not associated with an adverse immune response. In other embodiments, the NGF antagonist is an anti-NGF antibody. In still other embodiments, the anti-NGF antibody is humanized (such as antibody E3 described herein). In some embodiments, the anti-NGF antibody is antibody E3 (as described herein). In other embodiments, the anti-NGF antibody comprises one or more CDR(s) of antibody E3 (such as one, two, three, four, five, or, in some embodiments, all six CDRs from E3). In other embodiments, the antibody is human. In some embodiments, the antibody is a human anti-NGF neutralizing antibody described in WO 2005/019266. In still other embodiments, the anti-NGF antibody comprises the amino acid sequence of the heavy chain variable region shown in Table 1 (SEQ ID NO:1) and the amino acid sequence of the light chain variable region shown in Table 2 (SEQ ID NO:2). In still other embodiments, the antibody comprises a modified constant region, such as a constant region that is immunologically inert, e.g., does not trigger complement mediated lysis, or does not stimulate antibody-dependent cell mediated cytotoxicity (ADCC). In other embodiments, the constant region is modified as described in Eur. J. Immunol. (1999) 29:2613–2624; PCT Application No. PCT/GB99/01441; and/or UK Patent Application No. 9809951.8.

Anti-NGF Antibodies

In some embodiments of the invention, the NGF antagonist comprises an anti-NGF antibody. An anti-NGF antibody should exhibit any one or more of the following characteristics: (a) bind to NGF and inhibit NGF biological activity and/or downstream pathways mediated by NGF signaling function; (b) prevent, ameliorate, or treat any aspect of bone cancer pain including cancer pain associated with bone metastasis; (c) block or decrease NGF receptor activation (including TrkA receptor dimerization and/or autophosphorylation); (d) increase clearance of NGF; (e) inhibit (reduce) NGF synthesis, production or release.

Anti-NGF antibodies are known in the art, see, e.g., PCT Publication Nos. WO 01/78698, WO 01/64247, U.S. Pat. Nos. 5,844,092, 5,877,016, and 6,153,189; Hongo et al., *Hybridoma*, 19:215–227 (2000); *Cell. Molec. Biol.* 13:559–568 (1993); GenBank Accession Nos. U39608, U39609, L17078, or L17077.

In some embodiments, the anti-NGF antibody is a humanized mouse anti-NGF monoclonal antibody termed antibody "E3" (PCT WO 04/058184), which comprises the human heavy chain IgG2a constant region containing the following mutations: A330P331 to S330S331 (amino acid numbering with reference to the wildtype IgG2a sequence; see Eur. J. Immunol. (1999) 29:2613–2624); the human light chain kappa constant region; and the heavy and light chain variable regions shown in Tables 1 and 2.

TABLE 1

Heavy chain variable region

QVQLQESGPGLVKPSETLSLTCTVSGFSLIGYDLNWI (SEQ ID NO:1)

RQPPGKGLEWIGIIWGDGTTDYNSAVKSRVTISKDTS

KNQFSLKLSSVTAADTAVYYCARGGYWYATSYYFDYW

GQGTLVTVS.

TABLE 2

Light chain variable region

DIQMTQSPSSLSASVGDRVTITCRASQSISNNLNWYQ (SEQ ID NO:2)

QKPGKAPKLLIYYTSRFHSGVPSRFSGSGSGTDFTFT

ISSLQPEDIATYYCQQEHTLPYTFGQGTKLEIKRT.

The following polynucleotides encoding the heavy chain variable region or the light chain variable region were deposited at the ATCC on Jan. 8, 2003:

These polynucleotides also encode constant domains.

There are at least two techniques for determining CDRs: (1) an approach based on cross-species sequence variability (i.e., Kabat et al. *Sequences of Proteins of Immunological Interest*, (5th ed., 1991, National Institutes of Health, Bethesda Md.)); and (2) an approach based on crystallographic studies of antigen-antibody complexes (Chothia et al. (1989) *Nature* 342:877; Al-lazikani et al (1997) *J. Molec. Biol.* 273:927–948)). As used herein, a CDR may refer to CDRs defined by either approach or by a combination of both approaches.

In another embodiment, the anti-NGF antibody comprises one or more CDR(s) of antibody E3 (such as one, two, three, four, five, or, in some embodiments, all six CDRs from E3). Determination of CDR regions is well within the skill of the art. CDR(s) may be Kabat, Chothia, or a combination of Kabat and Chothia.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion, humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). For purposes of this invention, the antibody reacts with NGF in a manner that inhibits NGF and/or downstream pathways mediated by the NGF signaling function. In one embodiment, the antibody is a human antibody which recognizes one or more epitopes on human NGF. In another embodiment, the antibody is a mouse or rat antibody which recognizes one or more epitopes on human NGF. In another embodiment, the antibody recognizes one or more epitopes on an NGF selected from the group consisting of: primate, canine, feline, equine, and bovine. In other embodiments, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613–2624; PCT Application No. PCT/GB99/01441; and/or UK Patent Application No. 9809951.8.

The binding affinity of an anti-NGF antibody to NGF (such as hNGF) can be about 0.10 to about 0.80 nM, about 0.15 to

| Material | | ATCC Accession No. | Date of Deposit |
|---|---|---|---|
| Vector Eb.911.3E | E3 light chain V region | PTA-4893 | Jan. 8, 2003 |
| Vector Eb.pur.911.3E | E3 light chain V region | PTA-4894 | Jan. 8, 2003 |
| Vector Db.911.3E | E3 heavy chain V region | PTA-4895 | Jan. 8, 2003 |

Vector Eb.911.3E is a polynucleotide encoding the light chain variable region shown in Table 2; vector Eb.pur.911.3E is a polynucleotide encoding the light chain variable region shown in Table 2 and vector Db.911.3E is a polynucleotide encoding the heavy chain variable region shown in Table 1.

about 0.75 nM and about 0.18 to about 0.72 nM. In one embodiment, the binding affinity is between about 2 pM and 22 pM. In some embodiment, the binding affinity is about 10 nM. In other embodiments, the binding affinity is less than about 10 nM. In other embodiments, the binding affinity is about 0.1 nM or about 0.07 nM. In other embodiments, the binding affinity is less than about 0.1 nM, or less than about 0.07 nM. In other embodiments, the binding affinity is any of about 100 nM, about 50 nM, about 10 nM, about 1 nM, about 500 pM, about 100 pM, or about 50 pM to any of about 2 pM, about 5 pM, about 10 pM, about 15 pM, about 20 pM, or about 40 pM. In some embodiments, the binding affinity is any of about 100 nM, about 50 nM, about 10 nM, about 1 nM, about 500 pM, about 100 pM, or about 50 pM, or less than about 50 pM. In some embodiments, the binding affinity is less than any of about 100 nM, about 50 nM, about 10 nM, about 1 nM, about 500 pM, about 100 pM, or about 50 pM. In still other embodiments, the binding affinity is about 2 pM, about 5 pM, about 10 pM, about 15 pM, about 20 pM, about 40 pM, or greater than about 40 pM.

One way of determining binding affinity of antibodies to NGF is by measuring binding affinity of monofunctional Fab fragments of the antibody. To obtain monofunctional Fab fragments, an antibody (for example, IgG) can be cleaved with papain or expressed recombinantly. The affinity of an anti-NGF Fab fragment of an antibody can be determined by surface plasmon resonance (BIAcore3000™ surface plasmon resonance (SPR) system, BIAcore, INC, Piscaway N.J.). CM5 chips can be activated with N-ethyl-N'-(3-dimethylaminopropyl)-carbodiinide hydrochloride (EDC) and N-hydroxysuccinimide (NHS) according to the supplier's instructions. Human NGF (or any other NGF) can be diluted into 10 mM sodium acetate pH 4.0 and injected over the activated chip at a concentration of 0.005 mg/mL. Using variable flow time across the individual chip channels, two ranges of antigen density can be achieved: 100–200 response units (RU) for detailed kinetic studies and 500–600 RU for screening assays. The chip can be blocked with ethanolamine. Regeneration studies have shown that a mixture of Pierce elution buffer (Product No. 21004, Pierce Biotechnology, Rockford Ill.) and 4 M NaCl (2:1) effectively removes the bound Fab while keeping the activity of hNGF on the chip for over 200 injections. HBS-EP buffer (0.01M HEPES, pH 7.4, 0.15 NaCl, 3 mM EDTA, 0.005% Surfactant P20) is used as running buffer for the BIAcore assays. Serial dilutions (0.1–10× estimated $K_D$) of purified Fab samples are injected for 1 min at 100 µL/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data to a 1:1 Langmuir binding model (Karlsson, R. Roos, H. Fagerstam, L. Petersson, B. (1994). Methods Enzymology 6. 99–110) using the BIAevaluation program. Equilibrium dissociation constant ($K_D$) values are calculated as $k_{off}/k_{on}$. This protocol is suitable for use in determining binding affinity of an antibody to any NGF, including human NGF, NGF of another vertebrate (in some embodiments, mammalian) (such as mouse NGF, rat NGF, primate NGF), as well as for use with other neurotrophins, such as the related neurotrophins NT3, NT4/5, and/or BDNF.

In some embodiments, the antibody binds human NGF, and does not significantly bind an NGF from another vertebrate species (in some embodiments, mammalian). In some embodiments, the antibody binds human NGF as well as one or more NGF from another vertebrate species (in some embodiments, mammalian). In still other embodiments, the antibody binds NGF and does not significantly cross-react with other neurotrophins (such as the related neurotrophins, NT3, NT4/5, and/or BDNF). In some embodiments, the antibody binds NGF as well as at least one other neurotrophin. In some embodiments, the antibody binds to a mammalian species of NGF, such as horse or dog, but does not significantly bind to NGF from anther mammalian species.

The epitope(s) can be continuous or discontinuous. In one embodiment, the antibody binds essentially the same hNGF epitopes as an antibody selected from the group consisting of MAb 911, MAb 912, and MAb 938 as described in Hongo et al., *Hybridoma*, 19:215–227 (2000). In another embodiment, the antibody binds essentially the same hNGF epitope as MAb 911. In still another embodiment, the antibody binds essentially the same epitope as MAb 909. Hongo et al., supra. For example, the epitope may comprise one or more of: residues K32, K34 and E35 within variable region 1 (amino acids 23–35) of hNGF; residues F79 and T81 within variable region 4 (amino acids 81–88) of hNGF; residues H84 and K88 within variable region 4; residue R103 between variable region 5 (amino acids 94–98) of hNGF and the C-terminus (amino acids 111–118) of hNGF; residue E11 within pre-variable region 1 (amino acids 10–23) of hNGF; Y52 between variable region 2 (amino acids 40–49) of hNGF and variable region 3 (amino acids 59–66) of hNGF; residues L112 and S113 within the C-terminus of hNGF; residues R59 and R69 within variable region 3 of hNGF; or residues V18, V20, and G23 within pre-variable region 1 of hNGF. In addition, an epitope can comprise one or more of the variable region 1, variable region 3, variable region 4, variable region 5, the N-terminus region, and /or the C-terminus of hNGF. In still another embodiment, the antibody significantly reduces the solvent accessibility of residue R103 of hNGF. It is understood that although the epitopes described above relate to human NGF, one of ordinary skill can align the structures of human NGF with the NGF of other species and identify likely counterparts to these epitopes.

In one aspect, antibodies (e.g., human, humanized, mouse, chimeric) that can inhibit NGF may be made by using immunogens that express full length or partial sequence of NGF. In another aspect, an immunogen comprising a cell that overexpresses NGF may be used. Another example of an immunogen that can be used is NGF protein that contains full-length NGF or a portion of the NGF protein.

The anti-NGF antibodies may be made by any method known in the art. The route and schedule of immunization of the host animal are generally in keeping with established and conventional techniques for antibody stimulation and production, as further described herein. General techniques for production of human and mouse antibodies are known in the art and are described herein.

It is contemplated that any mammalian subject including humans or antibody producing cells therefrom can be manipulated to serve as the basis for production of mammalian, including human, hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) *Nature* 256:495–497 or as modified by Buck, D. W., et al., In Vitro, 18:377–381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-NGF monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for NGF, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a human NGF, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaradehyde, succinic anhydride, SOCl2, or R1N=C=NR, where R and R1 are different alkyl groups, can yield a population of antibodies (e.g., monoclonal antibodies).

If desired, the anti-NGF antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity, or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to NGF and greater efficacy in inhibiting NGF. It will be apparent to one of skill in the art that one or more polynucleotide changes can be made to the anti-NGF antibody and still maintain its binding ability to NGF.

"Humanized" antibodies generally refer to a molecule having an antigen binding site that is substantially derived from an immunoglobulin from a non-human species and the remaining immunoglobulin structure of the molecule based upon the structure and/or sequence of a human immunoglobulin. The antigen binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (for example, a humanized mouse antibody which contains all six CDRs from the mouse antibodies). Other forms of humanized antibodies have one or more CDRs (one, two, three, four, five, six) which are altered with respect to the original antibody. In some instances, framework region (FR) residues or other residues of the human immunoglobulin replaced by corresponding non-human residues. Furthermore, humanized antibodies may comprise residues which are not found in the recipient antibody or in the donor antibody.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; 6,180,370; and 6,548,640.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains. See, for example, Winter et al. Nature 349:293–299 (1991), Lobuglio et al. Proc. Nat. Acad. Sci. USA 86:4220–4224 (1989), Shaw et al. J Immunol. 138: 4534–4538 (1987), and Brown et al. Cancer Res. 47:3577–3583 (1987). Other references describe rodent CDRs grafted into a human supporting framework region (FR) prior to fusion with an appropriate human antibody constant domain. See, for example, Riechmann et al. Nature 332:323–327 (1988), Verhoeyen et al. Science 239:1534–1536 (1988), and Jones et al. Nature 321:522–525 (1986). Another reference describes rodent CDRs supported by recombinantly veneered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT Application No. PCT/GB99/01441; UK Patent Application No. 9809951.8. Other methods of humanizing antibodies that may also be utilized are disclosed by Daugherty et al., Nucl. Acids Res. 19:2471–2476 (1991) and in U.S. Pat. Nos. 6,180,377; 6,054,297; 5,997,867; 5,866,692; 6,210,671; and 6,350,861; and in PCT Publication No. WO 01/27160. Humanization can also include affinity maturation. See, e.g., U.S. Ser. No. 10/745,775, and PCT/US03/41252.

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In an alternative, antibodies may be made recombinantly and expressed using any method known in the art. In another alternative, antibodies may be made recombinantly by phage display technology. See, for example, U.S. Pat. Nos. 5,565,332; 5,580,717; 5,733,743; and 6,265,150; and Winter et al.,

*Annu. Rev. Immunol.* 12:433–455 (1994). Alternatively, the phage display technology (McCafferty et al., *Nature* 348: 552–553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., *Current Opinion in Structural Biology* 3, 564–571 (1993). Several sources of V-gene segments can be used for phage display. Clackson et al., *Nature* 352:624–628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., *J. Mol. Biol.* 222:581–597 (1991), or Griffith et al., *EMBO J.* 12:725–734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." Marks, et al., *Bio/Technol.* 10:779–783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM–nM range. A strategy for making very large phage antibody repertoires (also known as "the mother-of-all libraries") has been described by Waterhouse et al., *Nucl. Acids Res.* 21:2265–2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213, published Apr. 1, 1993). Unlike traditional humanization of rodent antibodies by CDR grafting, this technique provides completely human antibodies, which have no framework or CDR residues of rodent origin.

It is apparent that although the above discussion pertains to humanized antibodies, the general principles discussed are applicable to customizing antibodies for use, for example, in dogs, cats, primate, equines and bovines. It is further apparent that one or more aspects of humanizing an antibody described herein may be combined, e.g., CDR grafting, framework mutation and CDR mutation.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. *Vaccine* 19:2756 (2001); Lonberg, N. and D. Huszar *Int. Rev. Immunol* 13:65 (1995); and Pollock, et al., *J Immunol Methods* 231:147(1999). Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for NGF.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., *Proc. Nat. Acad. Sci.* 81:6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-NGF monoclonal antibody herein.

Anti-NGF antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, *Using Antibodies, a Laboratory Manual*, Cold Spring Harbor Laboratory Press, Cold Spring Harbor, N.Y., 1999. In an additional example, epitope mapping can be used to determine the sequence to which an anti-NGF antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4–6 amino acids long) can be isolated or synthesized (e.g., recombinantly) and used for binding assays with an anti-NGF antibody. In another example, the epitope to which the anti-NGF antibody binds can be determined in a systematic screening by using overlapping peptides derived from the NGF sequence and determining binding by the anti-NGF antibody. According to the gene fragment expression assays, the open reading frame encoding NGF is fragmented either randomly or by specific genetic constructions and the reactivity of the expressed fragments of NGF with the antibody to be tested is determined. The gene fragments may, for example, be produced by PCR and then transcribed and translated into protein in vitro, in the presence of radioactive amino acids. The binding of the antibody to the radioactively labeled NGF fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant NGF in which various fragments of the NGF polypeptide have been replaced (swapped) with sequences from a closely related, but antigenically distinct protein (such as another member of the neurotrophin protein family). By assessing binding of the antibody to the mutant NGF, the importance of the particular NGF fragment to antibody binding can be assessed.

Yet another method which can be used to characterize an anti-NGF antibody is to use competition assays with other antibodies known to bind to the same antigen, i.e., various fragments on NGF, to determine if the anti-NGF antibody binds to the same epitope as other antibodies. Competition assays are well known to those of skill in the art. Example of antibodies that can be used in the competition assays for the present invention include MAb 911, 912, 938, as described in Hongo, et al., *Hybridoma* 19:215–227 (2000).

Other NGF Antagonists

NGF antagonists other than anti-NGF antibodies may be used. In some embodiments of the invention, the NGF antagonist comprises at least one antisense molecule capable of blocking or decreasing the expression of a functional NGF. Nucleotide sequences of the NGF are known and are readily available from publicly available databases. See, e.g., Borsani et al., *Nuc. Acids Res.* 1990, 18, 4020; Accession Number NM 002506; Ullrich et al., *Nature* 303:821–825 (1983). It is routine to prepare antisense oligonucleotide molecules that will specifically bind NGF MRNA without cross-reacting with other polynucleotides. Exemplary sites of targeting include, but are not limited to, the initiation codon, the 5' regulatory regions, the coding sequence and the 3' untranslated region. In some embodiments, the oligonucleotides are about 10 to 100 nucleotides in length, about 15 to 50 nucleotides in length, about 18 to 25 nucleotides in length, or more. The oligonucleotides can comprise backbone modifications such as, for example, phosphorothioate linkages, and 2'-O sugar modifications well know in the art. Exemplary antisense molecules include the NGF antisense molecules described in U.S. Publication No. 20010046959; see also http://www.rna-tec.com/repair.htm.

In other embodiments, the NGF antagonist comprises at least one antisense molecule capable of blocking or decreasing the expression of a functional NGF receptor (such as TrkA and/or p75). Woolf et al., J. Neurosci. (2001) 21(3):1047–55; Taglialetela et al, J Neurochem (1996) 66(5): 1826–35. Nucleotide sequences of TrkA and p75 are known and are readily available from publicly available databases.

Alternatively, NGF expression and/or release and/or NGF receptor expression can be decreased using gene knockdown, morpholino oligonucleotides, RNAi, or ribozymes, methods that are well-known in the art. See
http://www.macalester.edu/~montgomery/RNAi.html;
http://pub32.ezboard.com/
fmorpholinosfrm19.showMessage?topicID=6.topic;
http://www.highveld.com/ribozyme.html.

In other embodiments, the NGF antagonist comprises at least one NGF inhibitory compound. As used herein, "NGF inhibitory compound" refers to a compound other than an anti-NGF antibody that directly or indirectly reduces, inhibits, neutralizes, or abolishes NGF biological activity. An NGF inhibitory compound should exhibit any one or more of the following characteristics: (a) bind to NGF and inhibit NGF biological activity and/or downstream pathways mediated by NGF signaling function; (b) prevent, ameliorate, or treat any aspect of bone cancer pain including cancer pain associated with bone metastasis; (c) block or decrease NGF receptor activation (including TrkA receptor dimerization and/or autophosphorylation); (d) increase clearance of NGF; (e) inhibit (reduce) NGF synthesis, production or release. Exemplary NGF inhibitory compounds include the small molecule NGF inhibitors described in U.S. Publication No. 20010046959; the compounds that inhibit NGF's binding to p75, as described in PCT Publication No. WO 00/69829, and PD90780 [7-(benzolylamino)-4,9-dihydro-4-methyl-9-oxopyrazolo[5,1-b]quinazoline-2-carboxylic acid] as described by Colquhoun et al., *J. Pharmacol. Exp. Ther.* 310(2):505–11 (2004); the compounds that inhibit NGF's binding to TrkA and/or p75, as described in PCT Publication No. WO 98/17278. Additional examples of NGF inhibitory compounds include the compounds described in PCT Publication Nos. WO 02/17914 and WO 02/20479, and in U.S. Pat. Nos. 5,342,942; 6,127,401; and 6,359,130. Further exemplary NGF inhibitory compounds are compounds that are competitive inhibitors of NGF. See U.S. Pat. No. 6,291,247. Furthermore, one skilled in the art can prepare other small molecules NGF inhibitory compounds.

In some embodiments, an NGF inhibitory compound binds NGF. Exemplary sites of targeting (binding) include, but are not limited to, the portion of the NGF that binds to the TrkA receptor and/or p75 receptor, and those portions of the NGF that are adjacent to the receptor-binding region and which are responsible, in part, for the correct three-dimensional shape of the receptor-binding portion. In another embodiment, an NGF inhibitory compound binds an NGF receptor (such as TrkA and/or p75) and inhibits an NGF biological activity. Exemplary sites of targeting include those portions of TrkA and/or p75 that bind to NGF.

In embodiments comprising small molecules, a small molecule can have a molecular weight of about any of 100 to 20,000 daltons, 500 to 15,000 daltons, or 1000 to 10,000 daltons. Libraries of small molecules are commercially available. The small molecules can be administered using any means known in the art, including inhalation, intraperitoneally, intravenously, intramuscularly, subcutaneously, intrathecally, intraventricularly, orally, enterally, parenterally, intranasally, or dermally. In general, when the NGF-antagonist according to the invention is a small molecule, it will be administered at the rate of 0.1 to 300 mg/kg of the weight of the patient divided into one to three or more doses. For an adult patient of normal weight, doses ranging from 1 mg to 5 g per dose can be administered.

In other embodiments, the NGF antagonist comprises at least one NGF structural analog. "NGF structural analogs" in the present invention refer to compounds that have a similar 3-dimensional structure as part of that of NGF and which bind to an NGF receptor under physiological conditions in vitro or in vivo, wherein the binding at least partially inhibits an NGF biological activity. In one embodiment, the NGF structural analog binds to a TrkA and/or a p75 receptor. Exemplary NGF structural analogs include, but are not limited to, the bicyclic peptides described in PCT Publication No. WO 97/15593; the bicyclic peptides described in U.S. Pat. No. 6,291,247; the cyclic compounds described in U.S. Pat. No. 6,017,878; and NGF-derived peptides described in PCT Publication No. WO 89/09225. Suitable NGF structural analogs can also be designed and synthesized through molecular modeling of NGF-receptor binding, for example by the method described in PCT Publication No. WO 98/06048. The NGF structural analogs can be monomers or dimers/oligomers in any desired combination of the same or different structures to obtain improved affinities and biological effects.

In other embodiments, the invention provides an NGF antagonist comprising at least one dominant-negative mutant of the TrkA receptor and/or p75 receptor. One skilled in the art can prepare dominant-negative mutants of, e.g., the TrkA receptor such that the receptor will bind the NGF and, thus, act as a "sink" to capture NGFs. The dominant-negative mutants, however, will not have the normal bioactivity of the TrkA receptor upon binding to NGF. Exemplary dominant-negative mutants include, but are not limited to, the mutants described in the following references: Li et al., *Proc. Natl. Acad. Sci. USA* 1998, 95, 10884; Eide et al., *J. Neurosci.* 1996, 16, 3123; Liu et al., *J. Neurosci* 1997, 17, 8749; Klein et al., *Cell* 1990, 61, 647; Valenzuela et al., *Neuron* 1993, 10, 963; Tsoulfas et al., *Neuron* 1993, 10, 975; and Lamballe et al., *EMBO J.* 1993, 12, 3083, each of which is incorporated herein by reference in its entirety. The dominant negative mutants can be administered in protein form or in the form of an expression vector such that the dominant negative mutant, e.g., mutant TrkA receptor, is expressed in vivo. The protein or expression vector can be administered using any means known in the art, such as intraperitoneally, intravenously, intramuscularly, subcutaneously, intrathecally, intraventricularly, orally, enterally, parenterally, intranasally, dermally, or by inhalation. For example, administration of expression vectors includes local or systemic administration, including injection, oral administration, particle gun or catheterized administration, and topical administration. One skilled in the art is familiar with administration of expression vectors to obtain expression of an exogenous protein in vivo. See, e.g., U.S. Pat. Nos. 6,436,908; 6,413,942; and 6,376,471.

Targeted delivery of therapeutic compositions containing an antisense polynucleotide, expression vector, or subgenomic polynucleotides can also be used. Receptor-mediated DNA delivery techniques are described in, for example, Findeis et al., *Trends Biotechnol*. (1993) 11:202; Chiou et al., *Gene Therapeutics: Methods And Applications Of Direct Gene Transfer* (J. A. Wolff, ed.) (1994); Wu et al., *J. Biol. Chem*. (1988) 263:621; Wu et al., *J. Biol. Chem*. (1994) 269: 542; Zenke et al., *Proc. Natl. Acad. Sci. USA* (1990) 87:3655; Wu et al., *J. Biol. Chem*. (1991) 266:338. Therapeutic compositions containing a polynucleotide are administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol. The therapeutic polynucleotides and polypeptides of the present invention can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, *Hum. Gene Ther*. (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther*. (1992) 3:147); ligand-linked DNA (see, e.g., Wu, *J. Biol. Chem*. (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, *Mol. Cell Biol*. (1994) 14:2411, and in Woffendin, *Proc. Natl. Acad. Sci.* (1994) 91:1581.

It is also apparent that an expression vector can be used to direct expression of any of the protein-based NGF antagonists described herein (e.g., anti-NGF antibody, TrkA immunoadhesin, etc.). For example, other TrkA receptor fragments that are capable of blocking (from partial to complete blocking) NGF and/or an NGF biological activity are known in the art.

In another embodiment, the NGF antagonist comprises at least one TrkA immunoadhesin. TrkA immunoadhesins as used herein refer to soluble chimeric molecules comprising the extracellular domain of a TrkA receptor and an immunoglobulin sequence, which retains the binding specificity of the TrkA receptor (substantially retains the binding specificity of the trkA receptor) and is capable of binding to NGF.

TrkA immunoadhesins are known in the art, and have been found to block the binding of NGF to the TrkA receptor. See, e.g., U.S. Pat. No. 6,153,189. Brennan et al. report administration of TrkA immunoadhesin in a rat model of post-surgical pain. See Society for Neuroscience Abstracts 24 (1–2) 880 (1998). In one embodiment, the TrkA immunoadhesin comprises a fusion of a TrkA receptor amino acid sequence (or a portion thereof) from TrkA extracellular domain capable of binding NGF (in some embodiments, an amino acid sequence that substantially retains the binding specificity of the trkA receptor) and an immunoglobulin sequence. In some embodiments, the TrkA receptor is a human TrkA receptor sequence, and the fusion is with an immunoglobulin constant domain sequence. In other embodiments, the immunoglobulin constant domain sequence is an immunoglobulin heavy chain constant domain sequence. In other embodiments, the association of two TrkA receptor-immunoglobulin heavy chain fusions (e.g., via covalent linkage by disulfide bond(s)) results in a homodimeric immunoglobulin-like structure. An immunoglobulin light chain can further be associated with one or both of the TrkA receptor-immunoglobulin chimeras in the disulfide-bonded dimer to yield a homotrimeric or homotetrameric structure. Examples of suitable TrkA immunoadhesins include those described in U.S. Pat. No. 6,153,189.

In another embodiment, the NGF antagonist comprises at least one anti-TrkA antibody capable of blocking, suppressing, altering, and/or reducing NGF physical interaction with the TrkA receptor and/or downstream signaling, whereby an NGF biological activity is reduced and/or blocked. Anti-TrkA antibodies are known in the art. Exemplary anti-TrkA antibodies include those described in PCT Publication Nos. WO 97/21732, WO 00/73344, WO 02/15924, and U.S. Publication No. 20010046959.

In another embodiment, the NGF antagonist comprises at least one anti-p75 antibody capable of blocking, suppressing and/or reducing NGF physical interaction with the p75 receptor and/or downstream signaling, whereby an NGF biological activity is reduced and/or blocked.

In another embodiment, the NGF antagonist comprises at least one kinase inhibitor capable of inhibiting downstream kinase signaling associated with TrkA and/or p75 receptor activity. An exemplary kinase inhibitor is K252a or K252b, which is known in the art and described in Knusel et al., J. Neurochem. 59:715–722 (1992); Knusel et al., J. Neurochemistry 57:955–962 (1991); Koizumi et al., J. Neuroscience 8:715–721 (1988); Hirata et al., Chemical Abstracts 111:728, XP00204135, see abstract and 12th Collective Chemical Substance Index, p. 34237, c. 3 (5–7), 55–60, 66–69), p. 34238, c.1 (41–44), c.2 (25–27, 32–33), p. 3423, c.3 (48–50, 52–53); and U.S. Pat. No. 6,306,849.

It is expected that a number of other categories of NGF antagonists will be identified if sought for by the clinician.

Identification of NGF Antagonists

Anti-NGF antibodies and other NGF antagonists can be identified or characterized using methods known in the art, whereby reduction, amelioration, or neutralization of an NGF biological activity is detected and/or measured. Methods described in PCT WO 04/065560 can be used. Another method, for example, a kinase receptor activation (KIRA) assay described in U.S. Pat. Nos. 5,766,863 and 5,891,650, can be used to identify NGF antagonists. This ELISA-type assay is suitable for qualitative or quantitative measurement of kinase activation by measuring the autophosphorylation of the kinase domain of a receptor protein tyrosine kinase (hereinafter "rPTK"), e.g. TrkA receptor, as well as for identification and characterization of potential antagonists of a selected rPTK, e.g., TrkA. The first stage of the assay involves phosphorylation of the kinase domain of a kinase receptor, for example, a TrkA receptor, wherein the receptor is present in the cell membrane of a eukaryotic cell. The receptor may be an endogenous receptor or nucleic acid encoding the receptor, or a receptor construct, may be transformed into the cell. Typically, a first solid phase (e.g., a well of a first assay plate) is coated with a substantially homogeneous population of such cells (usually a mammalian cell line) so that the cells adhere to the solid phase. Often, the cells are adherent and thereby adhere naturally to the first solid phase. If a "receptor construct" is used, it usually comprises a fusion of a kinase receptor and a flag polypeptide. The flag polypeptide is recognized by the capture agent, often a capture antibody, in the ELISA part of the assay. An analyte, such as a candidate anti-NGF antibody or other NGF antagonists, is then added together with NGF to the wells having the adherent cells, such that the tyrosine kinase receptor (e.g. TrkA receptor) is exposed to (or contacted with) NGF and the analyte. This assay enables identification of antibodies (or other NGF antagonists) that inhibit activation of TrkA by its ligand NGF. Following exposure to NGF and the analyte, the adhering cells are solubilized using a lysis buffer (which has a solubilizing detergent therein) and gentle agitation, thereby releasing cell lysate which can be subjected to the ELISA part of the assay directly, without the need for concentration or clarification of the cell lysate.

The cell lysate thus prepared is then ready to be subjected to the ELISA stage of the assay. As a first step in the ELISA stage, a second solid phase (usually a well of an ELISA microtiter plate) is coated with a capture agent (often a capture antibody) which binds specifically to the tyrosine kinase receptor, or, in the case of a receptor construct, to the flag polypeptide. Coating of the second solid phase is carried out so that the capture agent adheres to the second solid phase. The capture agent is generally a monoclonal antibody, but, as is described in the examples herein, polyclonal antibodies may also be used. The cell lysate obtained is then exposed to, or contacted with, the adhering capture agent so that the receptor or receptor construct adheres to (or is captured in) the second solid phase. A washing step is then carried out, so as to remove unbound cell lysate, leaving the captured receptor or receptor construct. The adhering or captured receptor or receptor construct is then exposed to, or contacted with, an anti-phosphotyrosine antibody which identifies phosphorylated tyrosine residues in the tyrosine kinase receptor. In one embodiment, the anti-phosphotyrosine antibody is conjugated (directly or indirectly) to an enzyme which catalyses a color change of a non-radioactive color reagent. Accordingly, phosphorylation of the receptor can be measured by a subsequent color change of the reagent. The enzyme can be bound to the anti-phosphotyrosine antibody directly, or a conjugating molecule (e.g., biotin) can be conjugated to the anti-phosphotyrosine antibody and the enzyme can be subsequently bound to the anti-phosphotyrosine antibody via the conjugating molecule. Finally, binding of the anti-phosphotyrosine antibody to the captured receptor or receptor construct is measured, e.g., by a color change in the color reagent.

The NGF antagonists can also be identified by incubating a candidate agent with NGF and monitoring any one or more of the following characteristics: (a) binding to NGF and inhibiting NGF biological activity and/or downstream pathways mediated by NGF signaling function; (b) preventing, ameliorating, or treating any aspect of bone cancer pain including cancer pain associated with bone metastasis; (c) blocking or decreasing NGF receptor activation (including TrkA receptor dimerization and/or autophosphorylation); (d) increasing clearance of NGF; (e) inhibiting (reducing) NGF synthesis, production or release. In some embodiments, an NGF antagonist is identified by incubating a candidate agent with NGF and monitoring binding and attendant reduction or neutralization of a biological activity of NGF. The binding assay may be performed with purified NGF polypeptide(s), or with cells naturally expressing, or transfected to express, NGF polypeptide(s). In one embodiment, the binding assay is a competitive binding assay, where the ability of a candidate antibody to compete with a known NGF antagonist for NGF binding is evaluated. The assay may be performed in various formats, including the ELISA format. In other embodiments, an NGF antagonist is identified by incubating a candidate agent with NGF and monitoring attendant inhibition of TrkA receptor dimerization and/or autophosphorylation.

Following initial identification, the activity of a candidate anti-NGF antagonist can be further confirmed and refined by bioassays, known to test the targeted biological activities. Alternatively, bioassays can be used to screen candidates directly. For example, NGF promotes a number of morphologically recognizable changes in responsive cells. These include, but are not limited to, promoting the differentiation of PC12 cells and enhancing the growth of neurites from these cells (Greene and Tischler, *Proc. Nat. Acad Sci. USA* 73:2424–2428 (1976); Urfer et al., *Biochem.* 36:4775–4781 (1997); Tsoulfas et al., *Neuron* 10:975–990 (1993)), promoting neurite outgrowth from explants of responsive sensory and sympathetic ganglia (Levi-Montalcini, R. and Angeletti, P. Nerve growth factor. *Physiol. Rev.* 48, 534–569, 1968) and promoting the survival of NGF dependent neurons such as embryonic dorsal root ganglion, trigeminal ganglion, or sympathetic ganglion neurons (e.g., Chun & Patterson, *Dev. Biol.* 75:705–711, (1977); Buchman & Davies, *Development* 118: 989–1001, (1993). Thus, the assay for inhibition of NGF biological activity entail culturing NGF responsive cells with NGF plus an analyte, such as a candidate anti-NGF antibody or a candidate NGF antagonist. After an appropriate time the cell response will be assayed (cell differentiation, neurite outgrowth or cell survival).

The ability of a candidate NGF antagonist to block or neutralize a biological activity of NGF can also be assessed by monitoring the ability of the candidate agent to inhibit NGF mediated survival in the embryonic rat dorsal root ganglia survival bioassay as described in Hongo et al., *Hybridoma* 19:215–227 (2000).

Compositions for Use in the Methods of the Invention

The compositions used in the methods of the invention comprise an effective amount of an NGF antagonist (such as anti-NGF antibody), and, in some embodiments, further comprise a pharmaceutically acceptable excipient. In some embodiments, the composition is for use in any of the methods described herein. Examples of such compositions, as well as how to formulate, are also described in an earlier section and below. In one embodiment, the composition comprises an NGF antagonist. In another embodiment, the composition comprises one or more NGF antagonists. In another embodiment, the composition comprises one or more NGF antagonists selected from any one or more of the following: an antagonist (e.g., an antibody) that binds (physically interacts with) NGF, an antagonist that binds to an NGF receptor (such as a TrkA and/or p75 receptor), and an antagonist that reduces (impedes and/or blocks) downstream NGF receptor signaling. In still other embodiments, the composition comprises any NGF antagonist that is not a TrkA immunoadhesin (i.e., is other than a TrkA immunoadhesin). In other embodiments, the composition comprises any NGF antagonist that is other than an anti-NGF antibody. In still other embodiments, the composition comprises any NGF antagonist that is other than a TrkA immunoadhesin and other than an anti-NGF antibody. In other embodiments, an NGF antagonist inhibits (reduces) NGF synthesis, production or release. In some embodiments, the NGF antagonist binds NGF and does not significantly cross-react with related neurotrophins (such as NT3, NT4/5, and/or BDNF). In some embodiments, the NGF antagonist is not associated with an adverse immune response. In some embodiments, the NGF antagonist is selected from the group consisting of an anti-NGF antibody, an anti-sense molecule directed to an NGF (including an anti-sense molecule directed to a nucleic acid encoding NGF), an anti-sense molecule directed to an NGF receptor (such as TrkA and/or p75), an NGF inhibitory compound, an NGF structural analog, a dominant-negative mutation of a TrkA receptor that binds an NGF, a TrkA immunoadhesin, an anti-TrkA antibody, an anti-p75 antibody and a kinase inhibitor. In another embodiment, the NGF antagonist is an anti-NGF antibody. In other embodiments, the anti-NGF antibody recognizes human NGF. In some embodiments, the anti-NGF antibody is human. In still other embodiments, the anti-NGF antibody is humanized (such as antibody E3 described herein). In still other embodiment, the anti-NGF antibody comprises a constant region that does not trigger an unwanted or undesirable immune response, such as antibody-mediated lysis or ADCC. In other embodiments, the anti-NGF antibody comprises one or more CDR(s) of antibody E3 (such as one, two, three, four, five, or, in some embodiments, all six CDRs from E3).

It is understood that the compositions can comprise more than one NGF antagonist. For example, a composition can comprise more than one member of a class of NGF antagonist (e.g., a mixture of anti-NGF antibodies that recognize different epitopes of NGF), as well as members of different classes of NGF antagonists (e.g., an anti-NGF antibody and an NGF inhibitory compound). Other exemplary compositions comprise more than one anti-NGF antibodies that recognize the same epitope(s), different species of anti-NGF antibodies that bind to different epitopes of NGF, or different NGF inhibitory compounds.

The composition used in the present invention can further comprise pharmaceutically acceptable carriers, excipients, or stabilizers (*Remington: The Science and Practice of Pharmacy* 20th Ed. (2000) Lippincott Williams and Wilkins, Ed. K. E. Hoover.), in the form of lyophilized formulations or aqueous solutions. Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The NGF antagonist and compositions thereof can also be used in conjunction with other agents that serve to enhance and/or complement the effectiveness of the agents. In some embodiments, the other agent is an opioid analgesic. In some embodiments, the other agent is an NSAID. In some embodiments, these agents are not opioid analgesics. In some embodiments, these agents are not NSAID.

Kits

The invention also provides kits for use in the instant methods. Kits of the invention include one or more containers comprising an NGF antagonist (such as an antibody, such as humanized antibody E3 described herein), and in some embodiments, further comprise instructions for use in accordance with any of the methods of the invention described herein. In some embodiments, the NGF antagonist is any NGF antagonist described herein. In still other embodiments, the kit comprises an NGF antagonist that is not a TrkA immunoadhesin (i.e., is other than a TrkA immunoadhesin). In other embodiments, the kit comprises an NGF antagonist that is other than an anti-NGF antibody. In still other embodiments, the kit comprises any NGF antagonist that is other than a TrkA immunoadhesin and other than an anti-NGF antibody. In some embodiment, the kit comprises an anti-NGF antibody (such as antibody E3 described herein). In other embodiments, the kit comprises an anti-NGF antibody comprising one or more CDR(s) of antibody E3 (such as one, two, three, four, five, or, in some embodiments, all six CDRs from E3). In some embodiments, the kit includes an opioid analgesic. In some embodiments, the kit includes an NSAID. In some embodiments, the kit does not include an opioid analgesic. In some embodiments, the kit does not include an NSAID. In some embodiments, the included instructions comprise a description of administration of the NGF antagonist to treat, ameliorate or prevent bone cancer pain including cancer pain associated with bone metastasis according to any of the methods described herein. The kit may further comprise a description of selecting an individual suitable for treatment based on identifying whether that individual has bone cancer pain including cancer pain associated with bone metastasis or whether the individual is at risk of bone cancer pain including cancer pain associated with bone metastasis. In still other embodiments, the instruction comprises a description of administering an NGF antagonist to treat, prevent and/or ameliorate bone cancer pain including cancer pain associated with bone metastasis. In still other embodiments, the instructions comprise a description of administering an NGF antagonist to an individual at risk of bone cancer pain including cancer pain associated with bone metastasis. In some embodiments, the NGF antagonist is co-administered with an opioid analgesic. In some embodiments, the NGF antagonist is co-administered with an NSAID. In some embodiments, the NGF antagonist is co-administered with an opioid analgesic and an NSAID. In some embodiments, the NGF antagonist is not co-administered with an opioid analgesic. In some embodiments, the NGF antagonist is not co-administered with an NSAID.

The instructions relating to the use of an NGF antagonist generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, ameliorating and/or preventing bone cancer pain including cancer pain associated with bone metastasis. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an NGF antagonist, such as an anti-NGF antibody. The container may further comprise a second pharmaceutically active agent.

Kits may optionally provide additional components such as buffers and interpretive information. Normally, the kit comprises a container and a label or package insert(s) on or associated with the container.

In some embodiments, the invention provides articles of manufacture comprising contents of the kits described above. In some embodiments, the kits comprise an NGF antagonist (such as anti-NGF antibody) with information indicating use to treat bone cancer pain including cancer pain associate with bone metastasis.

Administration of an NGF Antagonist and Assessment of Treatment

The NGF antagonist can be administered to an individual via any suitable route. For example, the NGF antagonist can be administered orally, intravenously, sublingually, subcutaneously, intraarterially, intrasynovially, intravescicular (such as via the bladder), intramuscularly, intracardiacly, intrathoracicly, intraperitoneally, intraventricularly, sublingually, by inhalation, by suppository, and transdermally. They can be administered orally, for example, in the form of tablets, troches, capsules, elixirs, suspensions, syrups, wafers, lollypops, chewing gum or the like prepared by art recognized procedures. It should be apparent to a person skilled in the art that the examples described herein are not intended to be limiting but to be illustrative of the techniques available.

Accordingly, in some embodiments, the NGF antagonist, such as an anti-NGF antibody, is administered to a individual in accordance with known methods, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, NGF antagonist can be aerosolized using a fluorocarbon formulation and a metered dose inhaler, or inhaled as a lyophilized and milled powder.

In one embodiment, an NGF antagonist is administered via site-specific or targeted local delivery techniques. Examples of site-specific or targeted local delivery techniques include various implantable depot sources of the NGF antagonist or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of an NGF antagonist (such as anti-NGF antibody) may be used for administration. In some embodiments, an NGF antagonist may be administered neat. In some embodiments, the NGF antagonist comprises an anti-NGF antibody, and may be in various formulations, including formulations comprising a pharmaceutically acceptable excipient. Pharmaceutically acceptable excipients are known in the art, and are relatively inert substances that facilitate administration of a pharmacologically effective substance. For example, an excipient can give form or consistency, or act as a diluent. Suitable excipients include, but are not limited to, stabilizing agents, wetting and emulsifying agents, salts for varying osmolarity, encapsulating agents, buffers, and skin penetration enhancers. Excipients as well as formulations for parenteral and nonparenteral drug delivery are set forth in *Remington, The Science and Practice of Pharmacy* 20th Ed. Mack Publishing (2000).

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

An anti-NGF antibody can be administered using any suitable method, including by injection (e.g., intraperitoneally, intravenously, subcutaneously, intramuscularly, etc.). Anti-NGF antibodies can also be administered via inhalation, as described herein. Generally, for administration of anti-NGF antibodies, an initial candidate dosage can be about 2 mg/kg. For the purpose of the present invention, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to reduce cancer pain associated with bone metastasis. An exemplary dosing regimen comprises administering an initial dose of about 2 mg/kg, followed by a weekly maintenance dose of about 1 mg/kg of the anti-NGF antibody, or followed by a maintenance dose of about 1 mg/kg every other week. However, other dosage regimens may be useful, depending on the pattern of pharmacokinetic decay that the practitioner wishes to achieve. For example, dosing from one-four time a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the NGF antagonist(s) used) can vary over time.

In general, when it is not an antibody, an NGF antagonist may (in some embodiments) be administered at the rate of about 0.1 to 300 mg/kg of the weight of the patient divided into one to three doses, or as disclosed herein. In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present invention, the appropriate dosage of an NGF antagonist will depend on the NGF antagonist(s) (or compositions thereof) employed, the type and severity of the pain to be treated, whether the agent is administered for preventive or therapeutic purposes, previous therapy, the patient's clinical history and response to the agent, and the discretion of the attending physician. Typically the clinician will administer an NGF antagonist, such as an anti-NGF antibody, until a dosage is reached that achieves the desired result.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of pain. Alternatively, sustained continuous release formulations of anti-NGF antibodies may be appropriate. Various formulations and devices for achieving sustained release are known in the art.

In one embodiment, dosages for an NGF antagonist may be determined empirically in individuals who have been given one or more administration(s) of NGF antagonist (such as an antibody). Individuals are given incremental dosages of an NGF antagonist, e.g., anti-NGF antibody. To assess efficacy of an NGF antagonist, an indicator of pain can be followed.

Administration of an NGF antagonist in accordance with the method in the present invention can be continuous or intermittent, depending, for example, upon the recipient's physiological condition, whether the purpose of the administration is therapeutic or prophylactic, and other factors known to skilled practitioners. The administration of an NGF antagonist (for example if the NGF antagonist is an anti-NGF antibody) may be essentially continuous over a preselected period of time or may be in a series of spaced dose, e.g., either before, during, or after developing pain; before; during; before and after; during and after; before and during; or before, during, and after developing pain. Administration can be before, during and/or after cancer has metastasized to bone, and any other event likely to give rise to cancer pain associated with bone metastasis.

In some embodiments, more than one NGF antagonist, such as an antibody, may be present. The antagonist can be the same or different from each other. At least one, at least two, at least three, at least four, at least five different NGF antagonists can be present. Generally, those NGF antagonists have complementary activities that do not adversely affect each other. NGF antagonists can also be used in conjunction with other agents that serve to enhance and/or complement the effectiveness of the agents. In some embodiments, the NGF antagonist is not co-administered with an opioid analgesic. In some embodiments, the NGF antagonist is not co-administered with an NSAID.

Therapeutic formulations of the NGF antagonist (such as an antibody) used in accordance with the present invention are prepared for storage by mixing an antibody having the desired degree of purity with optional pharmaceutically acceptable carriers, excipients or stabilizers (*Remington, The Science and Practice of Pharmacy* 20th Ed. Mack Publishing (2000)), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the NGF antagonist (such as an antibody) are prepared by methods known in the art, such as described in Epstein, et al., *Proc. Natl. Acad. Sci. USA* 82:3688 (1985); Hwang, et al., *Proc. Natl Acad. Sci. USA* 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington, The Science and Practice of Pharmacy* 20th Ed. Mack Publishing (2000).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or 'poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The formulations to be used for in vivo administration must be sterile. This is readily accomplished by, for example, filtration through sterile filtration membranes. Therapeutic anti-NGF antibody compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .μm, particularly 0.1 and 0.5 .μm, and have a pH in the range of 5.5 to 8.0.

The emulsion compositions can be those prepared by mixing a nerve growth factor antagonist with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Treatment efficacy can be assessed by methods well-known in the art.

EXAMPLES

The following Examples are provided to illustrate but not limit the invention.

Example 1

Anti-NGF Monoclonal Antibody is Effective in Treating Cancer Pain Associated with Bone Metastasis We used a murine bone cancer pain model to assess the efficacy of treatment with anti-NGF antibody 911 (a mouse monoclonal antibody; see Hongo, et al., *Hybridoma* 19:215–227 (2000)). This murine model of bone cancer pain is developed by intramedullary injection of osteolytic sarcoma cells into the mouse femur and the needle hole is then filled with dental amalgam to confine the tumor to bone. See Schwei et al., *J. Neuroscience* 19:10886–10897 (1999); and Luger et al., *Pain* 99:397–406 (2002). Experiments were performed on adult male C3H/HeJ mice (Jackson Laboratories, Bar Harbor, Me.). On day 0, an arthrotomy was performed following induction of general anesthesia with sodium pentobarbital (50 mg/kg, intraperitoneal (i.p.)). A needle was inserted into the medullary canal to create a pathway for the sarcoma cells. A depression was then made using a pneumatic dental high speed handpiece. In addition to naïve animals (n=5), sham animals (n=5) were generated with an injection of α-minimum essential media (20 μl, Sigma, St. Louis, Mo.) into the intramedullary space of the femur (designated sham) whereas sarcoma animals (n=5 for each condition tested) were injected with media containing $10^5$ 2472 osteolytic sarcoma cells (designated sarcoma or sarc) (20 μl, ATCC, Rockville, Md.). For all animals, the injection site was sealed with a dental amalgam plug to confine the cells or injected media within the intramedullary canal and followed by irrigation with sterile water (hypotonic solution). Finally, incision closure was achieved with wound clips. Clips were removed at day 5 so as not to interfere with behavioral testing. A second group of sarcoma-injected animals was treated with anti-NGF (10 mg/kg, i.p.) on days 6 and 13.

Behavioral analysis. Animals were tested for pain-related behaviors on day 10 and day 14 post-tumor implantation Animals were behaviorally tested using the following tests: ongoing pain (spontaneous guarding and flinching); ambulatory pain (limb use and rotarod), and movement-evoked pain (palpation-evoked guarding and palpation-evoked flinching). Animals were placed in a clear plastic observation box with a wire mesh floor and allowed to habituate for a period of 30 min. After acclimation, spontaneous guarding, spontaneous flinching, limb use during normal ambulation in an open field, and guarding during forced ambulation were assessed. Palpation-induced guarding and flinching were measured after the 2 min period of normally non-noxious palpation of the distal femur in sarcoma- and sham-injected animals.

The number of spontaneous flinches and time to spent guarding, representative of nociceptive behavior, were recorded simultaneously during a 2-min observation period. Guarding was defined as the time the hindpaw was held aloft while ambulatory and flinches were the number of times the animal held the limb aloft.

Normal limb use during spontaneous ambulation was scored on a scale of 5 to 0: (5) normal use, and (0) complete lack of limb use.

Forced ambulatory guarding was determined using a rotarod (Columbus Instruments, Columbus, Ohio). The rotarod machine has a revolving rod and is equipped with speed, acceleration, and sensitivity controls. The animals were placed on the rod with X4 speed, 8.0 acceleration, and 2.5 sensitivity. Forced ambulatory guarding was rated on a scale of 5–0: (5) normal use, and (0) complete lack of use.

After a normally non-noxious palpation of the distal femur in animals every second for 2 min, the animals were placed in the observation box and their palpation-induced guarding and palpation-induced flinching were measured for an additional 2 min.

Treatment with anti-NGF antibody. On day 6 and day 13, sarcoma-injected animals were intraperitoneally (i.p.) injected with anti-NGF antibody 911 at 10 mg/kg (sarc+anti-NGF, n=5), or sarcoma- and sham-injected animals were injected (i.p.) with saline (sham+veh or sarc+veh, n=5 for each condition). All animals were behaviorally analyzed on days 10 and 14.

Evaluation of ongoing pain behaviors. As shown in FIG. 1, sarcoma-injected animals (administered with saline) developed ongoing pain behaviors as assessed by spontaneous guarding and spontaneous flinching (both p<0.05, ANOVA) as compared to sham-injected animals (administered with saline). FIG. 1 also shows that i.p. administration of anti-NGF antibody 911 significantly reduced spontaneous guarding and spontaneous flinching in sarcoma-injected mice on day 10 and day 14 post-sarcoma implantation as compared to administration of saline to sarcoma-injected mice (p<0.05, ANOVA, for both spontaneous guarding and spontaneous flinching). These results indicate anti-NGF antibody 911 reduces ongoing pain in sarcoma-injected mice.

Figure 2:
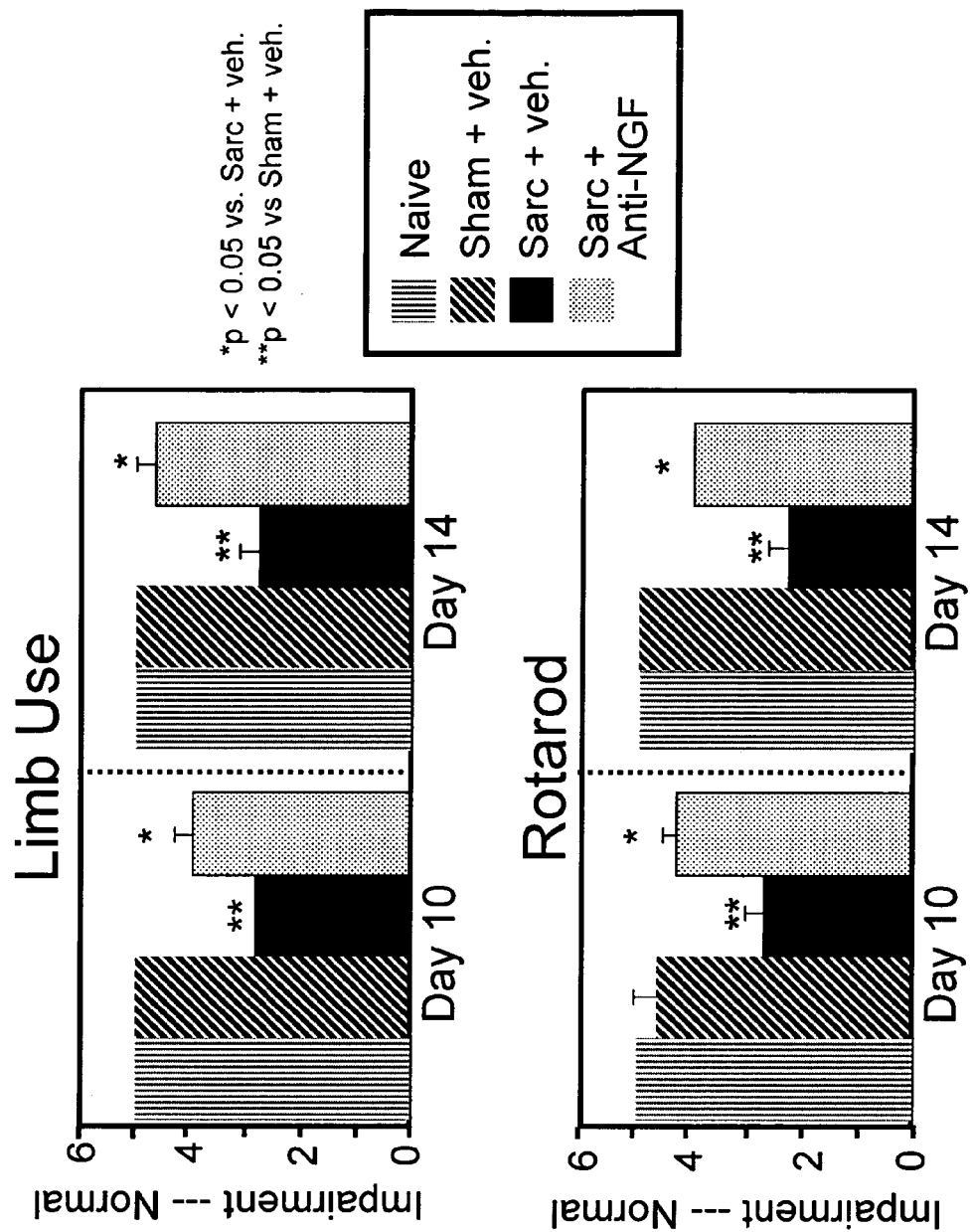
FIG. 2 is a graph depicting ambulatory pain as assessed by limb use and forced ambulatory guarding (rotarod) on day 10 and day 14 post-sarcoma injection. "Naive" refers to animals without any injection. "Sham+veh." refers to animals injected with α-minimum essential media into the femur marrow cavity and later injected with saline. "Sarc+veh." refers to animals injected with sarcoma into the femur marrow cavity and later injected with saline. "Sarc+Anti-NGF" refers to animals injected with sarcoma into the femur marrow cavity and later injected with anti-NGF antibody 911.

Evaluation of ambulatory pain behaviors. As shown in FIG. 2, sarcoma-injected animals (administered with saline) developed ambulatory pain behaviors as assessed by limb use and forced ambulation guarding (rotarod) (both p<0.05, ANOVA) as compared to sham-injected animals (administered with saline). FIG. 2 also shows that i.p. administration of anti-NGF antibody 911 significantly increased (closer to normal) limb use score and forced ambulatory guarding score in sarcoma-injected mice on day 10 and day 14 post-sarcoma implantation as compared to administration of saline to sarcoma-injected mice (p<0.05, ANOVA, for both limb use and force ambulatory guarding). These results indicate anti-NGF antibody 911 reduces ambulatory pain in sarcoma-injected mice.

Figure 3:
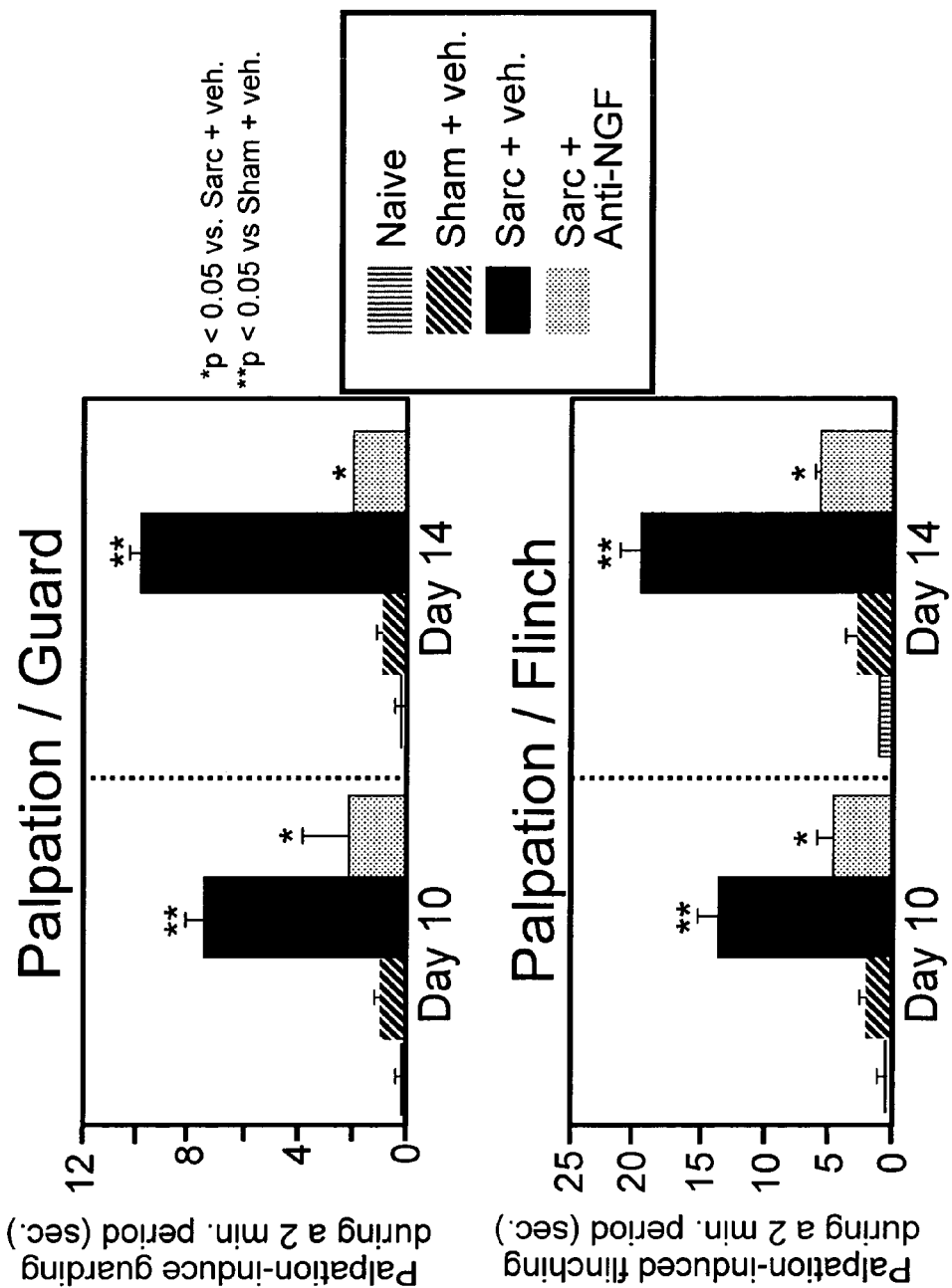
FIG. 3 is a graph depicting touch-evoked pain as assessed by palpation-induced guarding and palpation-induced flinching during a 2-min observation period on day 10 and day 14 post-sarcoma injection. "Naive" refers to animals without any injection. "Sham+veh." refers to animals injected with α-minimum essential media into the femur marrow cavity and later injected with saline. "Sarc+veh." refers to animals injected with sarcoma into the femur marrow cavity and later injected with saline. "Sarc+Anti-NGF" refers to animals injected with sarcoma into the femur marrow cavity and later injected with anti-NGF antibody 911.

Evaluation of touch-evoked pain behaviors. As shown in FIG. 3, sarcoma-injected animals (administered with saline) developed touch-evoked pain behaviors as assessed by palpation-induced guarding and palpation-induced flinching (both p<0.05, ANOVA) as compared to sham-injected animals (administered with saline). FIG. 3 also shows that i.p. administration of anti-NGF antibody 911 significantly reduced palpation-induced guarding and palpation-induced flinching in sarcoma-injected mice on day 10 and day 14 post-sarcoma implantation as compared to administration of saline to sarcoma-injected mice (p<0.05, ANOVA, for both palpation-induced guarding and palpation-induced flinching). These results indicate anti-NGF antibody 911 reduces touch-evoked pain in sarcoma-injected mice.

Example 2

Anti-NGF Monoclonal Antibody is Effective in Treating Bone Cancer Pain and Reduces Several Neurochemical Changes Associated with Peripheral and Central Sensitization in the Dorsal Root Ganglion and Spinal Cord Methods Animals. Experiments were performed on a total of 158 adult male C3H/HeJ mice (Jackson Laboratories, Bar Harbor, Me.), weighing 20–25 g. The mice were housed in accordance with the National Institutes of Health guidelines under specific pathogen free (SPF) conditions in autoclaved cages maintained at 22° C. with a 12-hour alternating light and dark cycle and were given autoclaved food and water ad libitum.

Culture and injection of tumor cells. Osteolytic murine sarcoma cells were obtained (NCTC 2472, ATCC, Rockville, Md.), stably transfected with green fluorescent protein (GFP) and maintained as previously described by Sabino et al., *Cancer Res.* 62: 7343–9 (2002).

Injection of tumor cells were performed as previously described. Honore et al., *Nat. Med.* 6: 521–8 (2000); Honore et al., *Neuroscience* 98:585–598 (2000); Luger et al., *Cancer Research* 61: 4038–4047 (2001). In brief, following induction of general anesthesia with sodium pentobarbital (50 mg/kg, i.p.), an arthrotomy was performed exposing the condyles of the distal femur. Hank's buffered sterile saline (HBSS, Sigma Chemical Co., St. Louis, Mo.; 20 μl; sham, n=40) or media containing $10^5$ osteolytic murine sarcoma cells (20 μl, NCTC 2472, ATCC, Rockville, Md; sarcoma, n=90) was injected into the intramedullary space of the mouse femur and the injection site sealed with dental amalgam (Dentsply, Milford, Del.), followed by irrigation with sterile filtered water. A day 14 endpoint was used, as this is the time point when the tumor is still confined to the bone and there is maximal presentation of cancer-related pain behaviors and maximal changes in expression of neurochemical markers of peripheral and central sensitization. Sham animals were used for control analysis of neurochemical changes and bone histology, as naïve animals were not significantly different behaviorally, neurochemically or histologically.

Treatment with anti-NGF antibody. To assess the effect of the anti-NGF antibody treatment on pain-related behaviors, neurochemical changes, tumor growth and bone destruction, the anti-NGF antibody (mAb 911, described in Hongo, et al., *Hybridoma* 19:215–227 (2000)) was administered (10 mg/kg/every 5 days, i.p.) beginning 6 days post-injection when observable bone destruction began and was terminated at 14 days post-injection, when significant bone destruction and pain behaviors were observed. The doses used in the current study caused no adverse effects, such as hypoalgesia, in naive mice. To monitor the general health of the mice, weights were recorded at the beginning and end of the experiments.

Mice were randomly placed into treatment groups receiving either sterile saline (sham+vehicle: n=28; sarcoma+vehicle: n=35; 1.4 μl/g/every 5 days, i.p.) or an anti-NGF antibody (sham+anti-NGF; n=4; sarcoma+anti-NGF: n=23, 10 mg/kg/every 5 days, i.p.) weekly. For behavioral comparison of anti-NGF antibody to morphine sulfate, mice were given a dose of morphine 15 minutes prior to behavioral testing (naïve: n=6; sham+vehicle: n=8; sarcoma+vehicle: n=8; sarcoma+anti-NGF: n=8; sarcoma+morphine 10 mg/kg, i.p.: n=8; sarcoma+morphine 30 mg/kg, i.p.: n=8). For thermal and mechanical sensitivity testing and the assessment of hindpaw skin innervation, mice were divided into two treatment groups receiving either sterile saline (naïve+vehicle: n=11) or an anti-NGF antibody (naïve+anti-NGF: n=11, 10 mg/kg/every 5 days, i.p.) weekly for 2 weeks.

Characterization of the anti-NGF antibody. The NGF antagonist antibody (mAb 911) is effective in blocking the binding of NGF to the Trk A and p75 NGF receptors and inhibiting Trk A autophosphorylation and blocking of NGF-dependent survival of dorsal root ganglion sensory neurons. Hongo, et al., *Hybridoma* 19:215–227 (2000).

Euthanasia and processing of tissue. Mice were sacrificed at day 14 post tumor injection and the tissues were processed for immunohistochemical analysis of spinal cord, dorsal root ganglia (DRG) as previously described and hindpaw skin. Honore et al., *Nat. Med.* 6: 521–8 (2000); Luger et al., *Cancer Research* 61: 4038–4047 (2001). Briefly, mice received a normally non-noxious mechanical stimulation of the injected knee 1.5 hours prior to euthanasia for induction of c-Fos expression. Honore et al., *Neuroscience* 98:585–598 (2000); Hunt et al., *Nature* 328: 632–634 (1987). Following this manipulation, mice were euthanized with $CO_2$ and perfused intracardially with 12 ml 0.1 M phosphate buffered saline (PBS) followed by 25 ml 4% formaldehyde/12.5% picric acid solution.

Spinal cord segments (L2–L4), DRG (L1–L5) and plantar skin were removed, post-fixed in the perfusion fixative and cryoprotected in 30% sucrose for 24 hours. Serial frozen spinal cord and skin sections, 60 μm thick, were cut on a sliding microtome, collected in PBS, and processed as free floating sections. Serial DRG sections, 15 μm thick, were cut on a cryostat and thaw-mounted on gelatin-coated slides for processing.

Following sectioning, DRG, spinal cord and plantar skin sections were briefly rinsed in PBS and then incubated in blocking solution (3% normal donkey serum (NDS) 0.3% Triton X-100 in PBS) for 1 hr followed by incubation overnight in the primary antibody. Spinal cord sections were immunostained for c-Fos protein (1:2000, Oncogene Research, San Diego, Calif.) and dynorphin (polyclonal guinea pig anti-dynorphin, 1:1,000, Neuromics, Minneapolis, Minn.). DRG sections were immunostained for activating transcription factor 3 (ATF-3) (polyclonal rabbit anti-ATF-3, 1:500, Santa Cruz Biotechnologies, Santa Cruz, Calif.) and CD68 (ED-1; polyclonal rat anti-CD68, 1:5,000, Serotec, Raleigh, N.C.). Skin sections were immunostained for calcitonin gene related peptide (CGRP) (1:15,000; Sigma, St. Louis, Mo.), tyrosine hydroxylase (TOH) (polyclonal rabbit anti-TOH, 1:2,000, Chemicon, Temecula, Calif.) and neurofilament H (Clone RT97) (polyclonal rabbit anti-RT-97, 1:2,500, Chemicon, Temecula, Calif.).

After incubation in primary antibody, sections were rinsed in PBS and then incubated in the secondary antibody solution for 3 hr. Secondary antibodies, conjugated to Cy3 or biotin (Jackson ImmunoResearch, West Grove, Pa.), were used at 1:600 or 1:500 respectively. To detect secondary antibodies conjugated to biotin: following secondary incubation, sections were rinsed in PBS and incubated in Cy3 conjugated streptavidin (1:4000; Jackson ImmunoResearch) for 45 minutes. To confirm specificity of the primary antibodies, controls included omission of the primary antibody or preabsorption with the corresponding synthetic peptide. Following immunostaining procedures, spinal cord, and plantar skin sections were mounted onto gelatin-coated slides. Mounted sections of skin, spinal cord and DRG were then dehydrated in alcohol gradients (70, 90, 100%), cleared in xylene and coverslips were mounted with DPX (Fluka, Switzerland).

Following radiological examination, at day 14, right (internal control) and left (tumor-bearing) femora were fixed in picric acid and 4% formalin at 4° C. overnight and decalcified in 10% EDTA (Sigma., St. Louis, Mo.) for no more than 14 days. Bones were then embedded in paraffin. Femoral sections, 5 µm thick were cut in the lateral plane and stained with tartrate-resistant acid phosphatase (TRAP) and hematoxylin and eosin (H&E) to visualize histological features of the normal bone marrow, tumor, osteoclasts and macrophages. To visualize sarcoma cells using fluorescence microscopy, femoral sections 5 µm thick were stained with an antibody raised against green fluorescent protein (GFP) (rabbit anti-GFP, 1:6,000, Molecular Probes, Eugene, Oreg.). GFP staining was performed using TSA-Plus Cyanine 3 System (PerkinElmer Life Sciences, Inc., Boston, Mass.), as previously described by Sevcik et al., Pain 111: 169–80 (2004).

Immunohistochemical analysis of the sham and cancerous femora was performed on decalcified, paraffin embedded 14 µm serial sections. The Tyramine Signal Amplification (TSA) System (Perkin Elmer life Sciences, Boston, Mass.) was used to amplify Cy3 labeled antibodies. Endogenous peroxidases were quenched by incubating the sections in 2% hydrogen peroxide for 1 hour. Sections were then rinsed three times with PBS for 10 minutes and blocked in TSA blocking buffer for 1 hour. Primary antiserum was added upon removal of the blocking buffer and allowed to incubate at room temperature overnight. Primary afferent unmyelinated and thinly myelinated sensory nerve fibers were labeled using an antibody raised against polyclonal rabbit anti-calcitonin gene related peptide (CGRP) (1:15,000; Sigma). Sections were rinsed three times in TSA wash buffer for 10 minutes followed by 45 minute incubation in streptavidin HRP (1:4,000). Sections were then rinsed three times with TSA wash buffer for 10 minutes. CY3-conjugated tyramine (1:600) was applied to the femora for 7 minutes, washed twice with TSA wash buffer and once with PBS. Finally, the sections were air dried, dehydrated through an alcohol gradient (70, 90 and 100%), cleared in xylene and mounted with DPX (Fluka).

Radiographical and osteoclast and macrophage proliferation analysis of bone. Radiographs (Faxitron X-ray Corp., Wheeling, Ill.) of dissected femora were obtained at the day 14 time point to optimally assess bone destruction. Images were captured on Kodak Min-R 2000 mammography film (Eastman Kodak Co., Rochester, N.Y.; exposure settings: 7 sec, 21 kVp). The extent of tumor-induced femoral bone destruction was radiologically assessed in the lateral plane of whole bone images at 5× magnification using a 0 to 5 scale (0, normal bone with no signs of destruction and 5, full-thickness bicortical bone loss). Honore et al., Nat. Med. 6: 521–8 (2000); Honore et al., Neuroscience 98:585–598 (2000); Luger et al., Cancer Research 61: 4038–4047 (2001).

Osteoclast and tumor associated macrophage (TAMs) proliferation were determined by quantifying the number of TRAP+ osteoclasts or TAMs on TRAP stained femoral sections as previously described. Honore et al., Nat. Med. 6: 521–8 (2000); Honore et al., Neuroscience 98:585–598 (2000). Briefly, TAMs are differentiated histologically from osteoclasts on femoral sections stained with TRAP as TRAP+ cells that are freely and multidimensionally dispersed throughout the tumor mass. Macrophages within the bone become activated due to tumor released factors that stimulate the cells, and the cellular appearance of these activated TAMs is marked by their highly irregular surface, multiple lamellipodia and phagocytic vacuoles. Osteoclasts are histologically differentiated as cells appearing TRAP+ and which are closely associated with regions of bone resorption. These cells are multinucleate and are found along the cortical and trabecular bone. Results are expressed as the mean number of osteoclasts per mm or TAMs per $mm^2$, respectively.

Quantification of tumor growth. Femora containing GFP-expressing sarcoma cells were imaged using a yellow 515 nm long pass emission filter on a Nikon E600 fluorescence microscope equipped with a SPOT II digital camera utilizing SPOT image capture software (Diagnostic Instruments, Sterling Heights, Mich.). The total area of intramedullary space and the percent of intramedullary space occupied by tumor were calculated using Image Pro Plus v3.0 software (Media Cybernetics, Silver Spring, Md.). Sabino et al., Cancer Res. 62: 7343–9 (2002); Sevcik et al., Pain 111: 169–80 (2004). The tumor characteristics of sarcoma cells transfected with GFP, such as growth rates, rate of bone resorption and the ability to induce bone cancer-related pain behaviors, were temporally, behaviorally and physically identical to non-transfected sarcoma cells. Sabino et al., Cancer Res. 62: 7343–9 (2002)

Quantification of sensory fibers in bone. The number of sensory nerve fibers was determined as previously described. Mach et al., Neuroscience 113:155–66 (2002). Briefly, the number of CGRP positive fibers in three bone regions (proximal, distal and diaphyseal) and the three bone tissues (periosteum, mineralized bone and marrow) were quantified. Only nerve fibers greater than 30 µm in length were included in the analysis. Six sections per animal were analyzed, and the fibers counted were expressed as fibers per total bone area.

Quantification of spinal cord, dorsal root ganglion and hindpaw skin. Fluorescently labeled spinal cord, DRG and skin tissue sections were analyzed using either an MRC 1024 confocal microscope imaging system (Bio-Rad, Philadelphia, Pa.), or a SPOT II digital camera on an Olympus BX-60 fluorescence microscope with SPOT image capture software (Diagnostic Instruments, Inc.).

The number of DRG neurons expressing activating transcription factor 3 (ATF-3) were counted under 200× magnification with a 1 $cm^2$ eyepiece grid. The total number of neurons (small, medium and large) was determined by counting both labeled and non-labeled neuronal cells bodies (non-labeled cell bodies exhibit background labeling that could be examined through a rhodamine or FITC filter) and results expressed as percent of total number of neurons which express ATF-3-immunoreactivity (IR). To prevent duplicate counting of neuronal cell bodies, counts were conducted on every fourth serial section for each marker. To quantify the activated or infiltrating macrophages in DRG, SPOT camera grey scale images were obtained on a minimum of four ipsilateral and contralateral DRG sections per animal and analyzed using Image Pro Plus version 3.0 software (Media Cybernetics). For each image, regions of the DRG containing only sensory neuronal cell bodies (excluding peripheral nerve) were outlined. While viewing the monitor, upper and lower thresholds of gray level density were set such that only specific CD68-IR cellular profiles were discriminated from the background in the outlined DRG. The number of cellular profiles was counted per section automatically. The SPOT camera output had been calibrated in Image Pro Plus such that the actual area of each outlined region within acquired images could be determined. The section values for CD68-IR cellular profiles and outlined areas were summed for each animal and results were expressed as total number of CD68-IR cellular profiles per unit area ($mm^2$).

Quantification was carried out in spinal cord sections at lumbar levels L2–L4 as these spinal segments receive significant afferent input from the L1–L3 DRGs, which are the principal ganglia that provide afferent input to the mouse femur. Edoff et al., *Cell & Tissue Research* 299: 193–200 (2000); Molander C, *J. Comp. Neurol.* 260: 246–255 (1987); Puigdellivol-Sanchez A et al., the *Anatomical Record* 260: 180–188 (2000); Puigdellivol-Sanchez A et al., *Neurosci. Lett.* 251: 169–172 (1998). Quantification of spinal cord sections for dynorphin was obtained from 4 randomly selected L2–L4 coronal spinal cord sections per animal. The number of dynorphin-IR neurons in spinal cord laminae III–VI were counted at 100× magnification and expressed as mean number of neurons per 60 µm L2–L4 section per animal. The number of c-Fos-IR neurons was counted in laminae III–VI of the dorsal horn in 8 randomly selected L3/L4 coronal spinal cord sections per animal. To be considered c-Fos-IR, the immunofluorescence threshold of the nuclear profile was set at three times the mean background immunofluorescence level of the tissue section. Results are given as mean number of c-Fos-IR neurons per spinal cord section.

Quantification of epidermal innervation density was performed on 4 randomly selected plantar hindpaw skin sections per animal. The total number of CGRP, TOH and RT97-IR nerve fibers were counted at 200× magnification. Counting rules were established to count only single intra-epidermal fibers and not multiple branches of the same fiber. McCarthy et al., *Neurology* 45: 1848–55 (1995). The total length of epidermis in all sections quantified was measured using a 1 $cm^2$ eyepiece grid. Only nerve fibers that were at least 25 µm in length, and projected into the superficial epidermis were counted. Results are given as the mean number of intra-epidermal nerve fibers per mm length per animal.

Behavioral analysis. Mice were tested for bone cancer pain-related behaviors 10 and 14 days following sham or tumor injections when pain behaviors are significantly evident to assess the efficacy of anti-NGF treatment. The anti-NGF treatment was compared to morphine (Baxter, Deerfield, Ill.; 10 mg/kg, i.p.) treatment and was administered 15 minutes prior to behavioral testing to ensure that animals were tested within the therapeutic window of drug action. Hasselstrom et al., *Pharmacology & Toxicology* 79: 40–6 (1996).

Mice were also tested 8, 10, 12 and 14 days following tumor or sham injections to assess efficacy of anti-NGF treatment (10 mg/kg/every 5 days, i.p.) in attenuating pain-related behaviors throughout the progression of the disease. Animals were observed over a 2-minute period and ongoing and palpation-evoked bone cancer pain behaviors were analyzed, as previously described. Luger et al., *Pain* 99:397–406 (2002); Sabino et al., *Cancer Res.* 62: 7343–9 (2002); Sabino et al., *International Journal of Cancer* 104: 550–558 (2003). Briefly, the number of hindpaw flinches and time spent guarding were recorded as measures of ongoing pain, as these measures mirror patients in a clinical setting with bone cancer who protect or suspend their tumor-bearing limb. In our model, movement-evoked pain due to palpation of the injected limb was evaluated using previously validated tests. Luger et al., *Cancer Research* 61: 4038–4047 (2001); Sabino et al., *International J. of Cancer* 104: 550–558 (2003); Sevcik et al., *Pain* 111: 169–80 (2004). Palpation-evoked pain behaviors were examined where animals received a normally non-noxious palpation to the tumor- or sham-injected limb for two minutes prior to observation. Luger et al., *Cancer Research* 61: 4038–4047 (2001); Sevcik et al., *Pain* 111: 169–80 (2004). Mice were monitored over a 2-minute period and the number of flinches and time spent guarding were recorded. Palpation-evoked behavior tests were developed to reflect the clinical condition when patients with bone cancer experience pain following normally non-noxious movement of the tumor-bearing limb.

Following a 15 minute acclimation period, thermal and mechanical sensitivity were measured in naïve and naïve+anti-NGF animals to assess whether the normal pain threshold responses were altered with anti-NGF treatment. Thermal sensitivity was measured using a Thermal Paw Stimulator (University of California, San Diego, San Diego, Calif.). The intensity of radiant heat was adjusted so that the naïve animals responded to the heat by elevating the hindpaw approximately nine seconds after the heat was initiated. Choi et al., *Life Sci.* 73: 471–85 (2003). The mice were allowed 5 minutes to recover between each trial. A single trial consisted of 4 measurements per hindpaw, the longest latency was dropped and the remaining 3 measurements were averaged. Mechanical sensitivity was measured using a previously validated method. Chaplan et al., *J. Neuroscience Methods* 53: 55–63 (1994) Von Frey filaments (Stoelting Co., Wood Dale, Ill.) were applied to the hindpaw of the animals, and the withdrawal threshold was determined by increasing and decreasing the stimulus intensity between 0.2 and 15.1 gram equivalents of force. A positive response was noted if the paw was quickly withdrawn.

RTPCR Analysis of mRNA levels of NGF in the 2472 cell line. Total RNA from triplicate mouse tissue samples or 2472 sarcoma cells was prepared according to manufacturer's instructions using the RNeasy micro kit (Qiagen), and the RNA was quantified using Ribogreen reagent (Molecular Probes). Two-step RT-PCR was performed using the TaqMan Gold RT-PCR kit (Applied Biosystems). The RNA was reverse transcribed using random hexamers, and the cDNA was amplified using a primer/probe set specific for NGF (muNGF-187F: GGGCTGGATGGCATGCT (SEQ ID NO:3), muNGF-256R: GCGTCCTTGGCAAAACCTT (SEQ ID NO:4), muNGF-208T: CCAAGCTCACCTCAGT-GTCTGGGCC (SEQ ID NO:5)). The samples were analyzed in duplicate from the RT level and normalized to total RNA input.

Statistical analysis. The SPSS version 11 computer statistics package (SPSS, Chicago, Ill.) was used to perform statistical analyses. Mixed effects linear regression modeling was used to analyze the repeated measures data, which can accommodate subjects measured at differing time intervals, include both fixed and time-varying covariates, and can estimate individual rates of change. Each dependent outcome variable was compared across groups using a non-parametric analysis of variance (Kruskal-Wallis). Significant Kruskal-Wallis analyses were followed by non-parametric post-hoc comparisons between pairs of groups using the Mann-Whitney U test. Results were considered statistically significant at $P<0.05$. In all cases, the investigator was blind to the experimental status of each animal.

Results

Figure 4:
FIG. 4 shows photographs demonstrating that the anti-NGF antibody had no effect on disease progression in bone at day 14 (d14) post tumor injection. Sham animals (n=8), given vehicle (sham+vehicle), are shown in (a) and (d); sarcoma (GFP transfected) injected animals (n=13), given vehicle (sarcoma+vehicle) are shown in (b) and (e); and sarcoma (GFP transfected) injected animals (n=8), given the anti-NGF antibody (sarcoma+anti-NGF), are shown in (c) and (f).

Anti-NGF administration had no effect on disease progression or macrophage infiltration in the bone. The effects of anti-NGF treatment on bone destruction, osteoclast proliferation and tumor growth were examined at day 14 post tumor injection. Sham-injected mice did not demonstrate significant bone destruction (bone score 0.9±0.4; FIG. 4*a*), osteoclast proliferation (4.6±0.4 osteoclasts/mm) or tumor growth (FIG. 4*d*), as assessed by radiological, TRAP and H&E/GFP analysis, respectively as compared to sarcoma-injected mice. In sarcoma+vehicle mice, there was extensive bone destruction as observed and characterized by multifocal radiolucencies (bone score 3.5±0.2; FIG. 4b), marked increase in the number of osteoclasts (4.0±0.7 osteoclasts/mm) and the tumor had completely filled the intramedullary space (100±0.0% of intramedullary space; FIG. 4e). Treatment of tumor-bearing mice with anti-NGF from day 6 to day 14 post tumor injection resulted in no significant change in bone resorption (3.1±0.6; FIG. 4c), no reduction in sarcoma-induced osteoclast proliferation (3.5±0.1 osteoclasts/mm) or tumor growth (98.0±0.9% of intramedullary space; FIG. 4f) as compared to sarcoma+vehicle animals.

Fourteen days following tumor injection, sarcoma+vehicle mice displayed an up regulation of TAMs (39.8±12.6 TAMs/mm$^2$) as compared to sham+vehicle control mice (0.0±0.0 TAMs/mm$^2$). Anti-NGF treatment of sarcoma-injected mice (29.5±7.3 TAMs/mm$^2$) did not significantly alter this TAM infiltration, as seen in the sarcoma+vehicle mice.

Anti-NGF treatment had no observable effect on sensory or sympathetic innervation in bone or skin. Thinly myelinated or unmyelinated peptidergic sensory nerve fibers were labeled with an antibody raised against calcitonin gene related peptide (CGRP). CGRP-IR nerve fibers were found throughout the entire bone (periosteum, mineralized bone and bone marrow) of both naïve+vehicle (12.2±0.3 fibers/mm) and naïve+anti-NGF (13.0±0.8 fibers/mm) animals.

Figure 5:
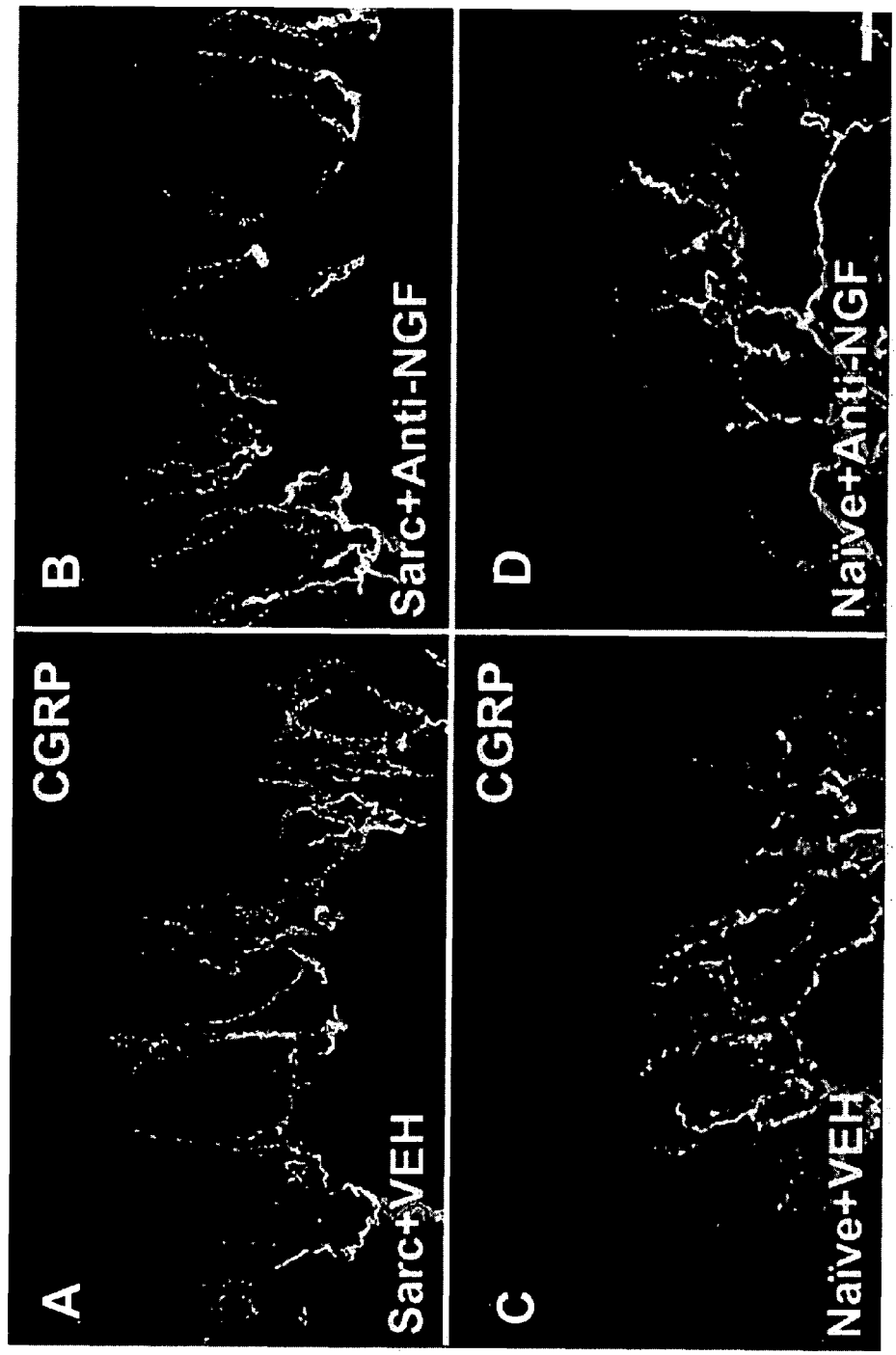
FIG. 5 shows photographs demonstrating that the anti-NGF antibody treatment had no observable effect on sensory innervation in skin. Hindpaw skin samples of both sarcoma-injected (a, b) and naïve (c, d) mice were immunostained for the neuropeptide calcitonin gene-related peptide (CGRP), which labels unmyelinated peptidergic sensory nerve fibers. Immunostaining of CGRP of hindpaw skin samples from sarcoma injected and vehicle treated (a, n=3) mice, sarcoma injected and anti-NGF antibody treated (b, n=8) mice, naïve and vehicle treated (c, n=8) mice, and naïve and anti-NGF antibody treated (d, n=8) mice are shown. Scale bar: 50 μm.

Thinly myelinated or unmyelinated peptidergic sensory nerve fibers (CGRP-IR), large myelinated sensory fibers (RT97-IR) and noradrenergic sympathetic nerve fibers (TOH-IR) were analyzed in the hindpaw plantar skin by antibodies raised against CGRP, RT-97 and TOH, respectively. There was no significant difference between the intensity or density of CGRP positive fibers in sarcoma+vehicle (12.0±0.8 fibers/mm) and sarcoma+anti-NGF (12.5±0.6 fibers/mm) hindpaw skin samples (FIGS. 5a and 5b). Similarly, there was no difference in intensity or density of CGRP positive fibers between naïve+vehicle (FIG. 5c, n=8) mice and naïve+anti-NGF (FIG. 5d, n=8) mice. There was no change in the number of nerve fibers expressing CGRP in sarcoma-injected and naïve mice (a,b vs. c,d). Differences in the density and intensity of RT97 positive and TOH positive fibers were also undetectable in sarcoma+vehicle (7.3±0.7 RT97+ fibers/mm; 3.1±0.7 TOH+ fibers/mm) and sarcoma+anti-NGF treated (7.3±0.7 RT97+ fibers/mm; 3.6±0.7 TOH+ fibers/mm) animals. Similarly, there was no significant difference between the intensity or density of CGRP positive fibers in naïve+vehicle (12.5±0.5 fibers/mm) and naïve+anti-NGF (11.9±0.7 fibers/mm) hindpaw skin samples (FIGS. 5c and 5d). Differences in the density and intensity of RT97 positive and TOH positive fibers were also undetectable in naïve+vehicle (10.4±0.4 RT97+ fibers/mm; 3.4±0.4 TOH+ fibers/mm) and naïve+anti-NGF treated (11.9±0.7 RT97± fibers/mm; 3.0±0.8 TOH+ fibers/mm) animals. There were no significant observable differences between the intensity or density of CGRP, RT97 or TOH positive fibers in the skin samples of sarcoma+vehicle and sarcoma+anti-NGF versus the naïve+vehicle and naïve+anti-NGF animals.

Anti-NGF antibody therapy significantly reduced bone cancer pain behaviors. Sarcoma+vehicle mice demonstrated a greater time spent guarding as compared to the sham+vehicle controls (FIG. 6a). Additionally, sarcoma+vehicle mice exhibited an increased number of flinches as compared to sham+vehicle controls (FIG. 6b). Administration of anti-NGF (from day 6 to day 14) in sarcoma-injected mice significantly attenuated spontaneous guarding as compared to sarcoma+vehicle mice (FIG. 6a). Anti-NGF treatment also significantly reduced spontaneous flinching in sarcoma-injected mice (FIG. 6b).

Movement-evoked pain was analyzed by measuring palpation-induced responses. Sarcoma+vehicle mice demonstrated a greater time spent guarding after palpation as compared to the sham+vehicle controls (FIG. 6c). Sarcoma+vehicle mice also exhibited an increased number of flinches after palpation as compared to sham+vehicle controls (FIG. 6d). Anti-NGF treatment in sarcoma-injected mice significantly reduced both palpation-evoked guarding (FIG. 6c) and palpation-evoked flinching (FIG. 6d). In preliminary studies, no significant behavioral differences or side effects were observed between sham-operated animals receiving either vehicle or anti-NGF.

Figure 6:
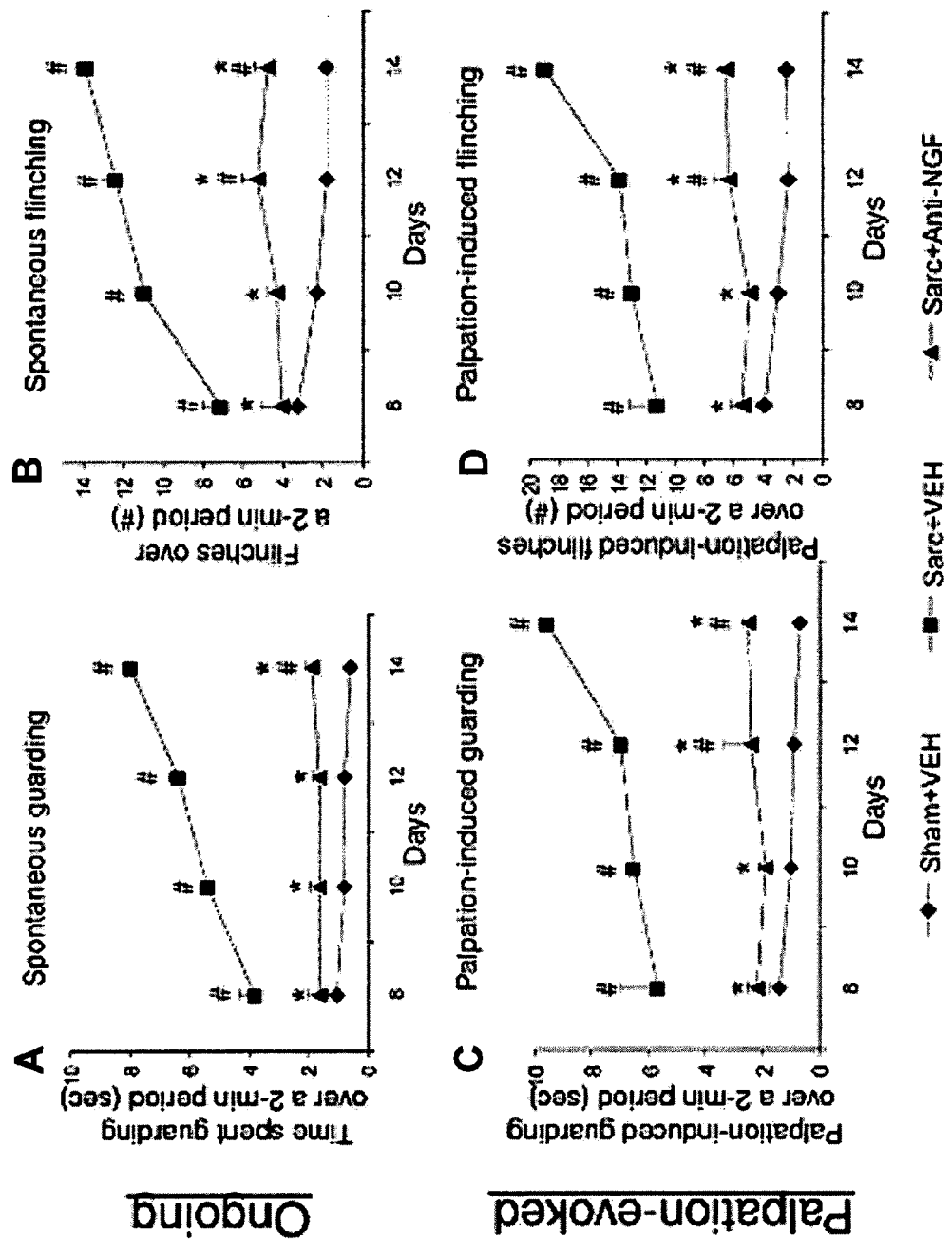
FIG. 6 shows graphs demonstrating that anti-NGF treatment attenuated bone cancer pain. The time spent guarding and number of spontaneous flinches of the sarcoma injected limb over a 2-minute observation period was used as a measure of ongoing pain 8, 10, 12 and 14 days after injection and confinement of sarcoma cells to the left femur (a, b). Parameters of movement-evoked pain included quantification of time spent guarding and the number of flinches over a 2-minute observation period following a normally non-noxious palpation of the sarcoma-injected femur (c, d). "#" indicates P<0.05 vs. sham+vehicle; and "*" indicates P<0.05 vs. sarcoma+vehicle.

FIG. 6 shows that anti-NGF treatment (n=8) from 6 to 14 days post tumor injection (triangle) significantly reduced ongoing and palpation-evoked pain behaviors on days 10, 12 and 14 as compared to sarcoma+vehicle (n=8) (square), and was significantly reduced to sham levels at day 10 for all parameters (diamond). At all time points, sham+vehicle (n=8) are significantly different from sarcoma+vehicle. Thus, anti-NGF treatment (10 mg/kg, i.p., every 5 days) attenuated both ongoing and movement-evoked bone cancer pain behaviors throughout the progression of the disease.

Figure 7:
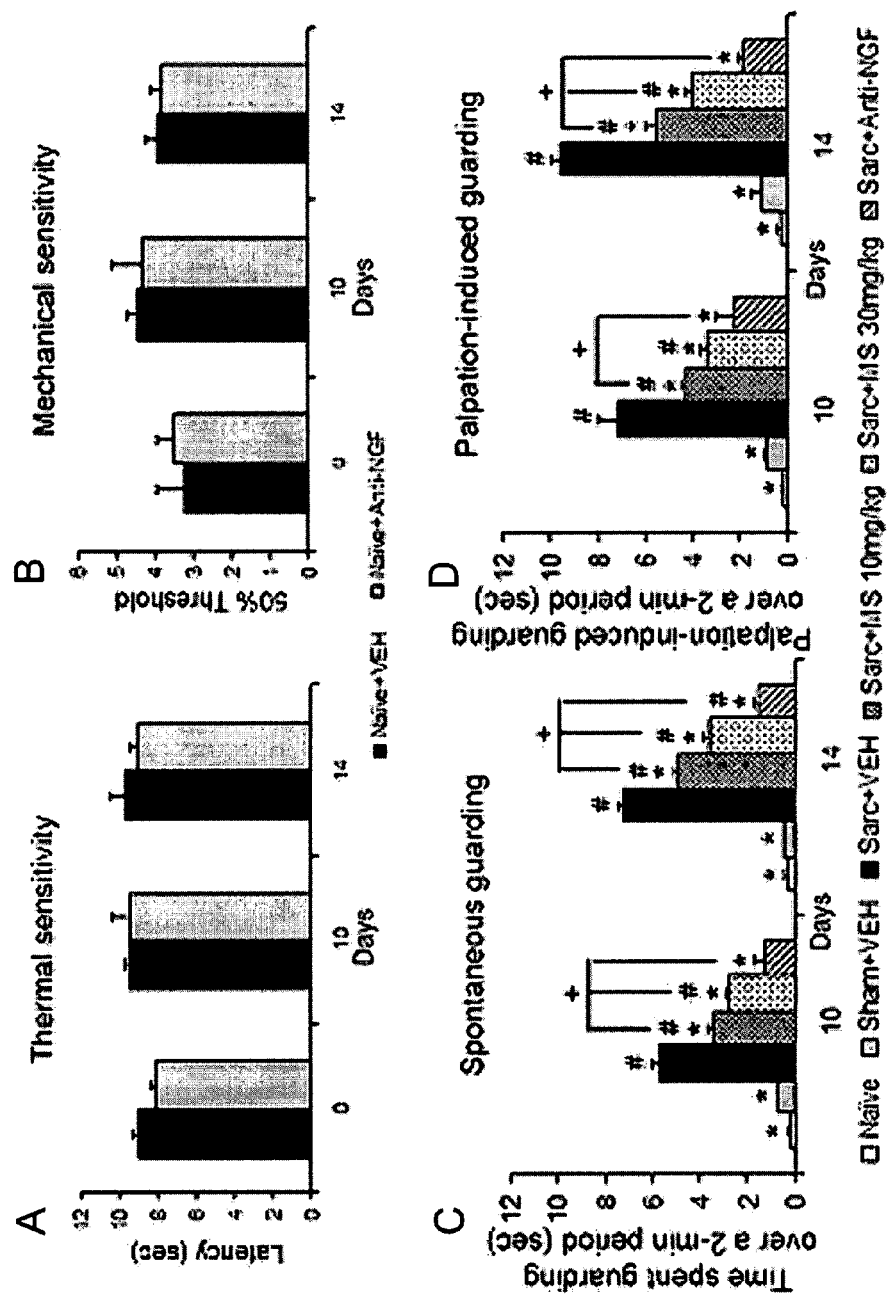
FIG. 7 shows graphs demonstrating that anti-NGF treatment had no effect on baseline thermal or mechanical thresholds and had greater efficacy than morphine (MS) in reducing bone cancer pain.

Anti-NGF treatment had no effect on baseline thermal or mechanical thresholds and was comparable to the efficacy of morphine in reducing bone cancer pain. There was no significant increase in latency of paw withdrawal to a thermal stimulus or increase in threshold of mechanical stimulation with anti-NGF administration as compared to normal pain thresholds. Anti-NGF treatment had no effect on either normal thermal response (FIG. 7a) as compared to naïve+vehicle or normal mechanical stimulation (FIG. 7b) as compared to naïve+vehicle.

Animals were tested to compare the efficacy of morphine sulfate (MS) to the anti-NGF antibody in reducing bone cancer-related behaviors. Behavioral assessment on days 10 and 14 revealed that sarcoma+vehicle animals showed statistically longer time guarding (FIG. 7c) and increased time guarding in response to palpation (FIG. 7d) of the injected limb as compared to sham+vehicle animals. Treatment with either anti-NGF (10 mg/kg/every 5 days, i.p.) or morphine sulfate (10 mg/kg, or 30 mg/kg i.p.) significantly reduced both ongoing and movement-evoked guarding behaviors at days 10 and 14 post tumor injection (FIG. 7c, 7d), as compared to sarcoma+vehicle mice. Anti-NGF treatment significantly attenuated the bone cancer-related pain behaviors more effectively as compared to morphine doses of either 10 mg/kg or 30 mg/kg ($p < 0.05$ vs. Sarcoma+anti-NGF).

Figure 8:
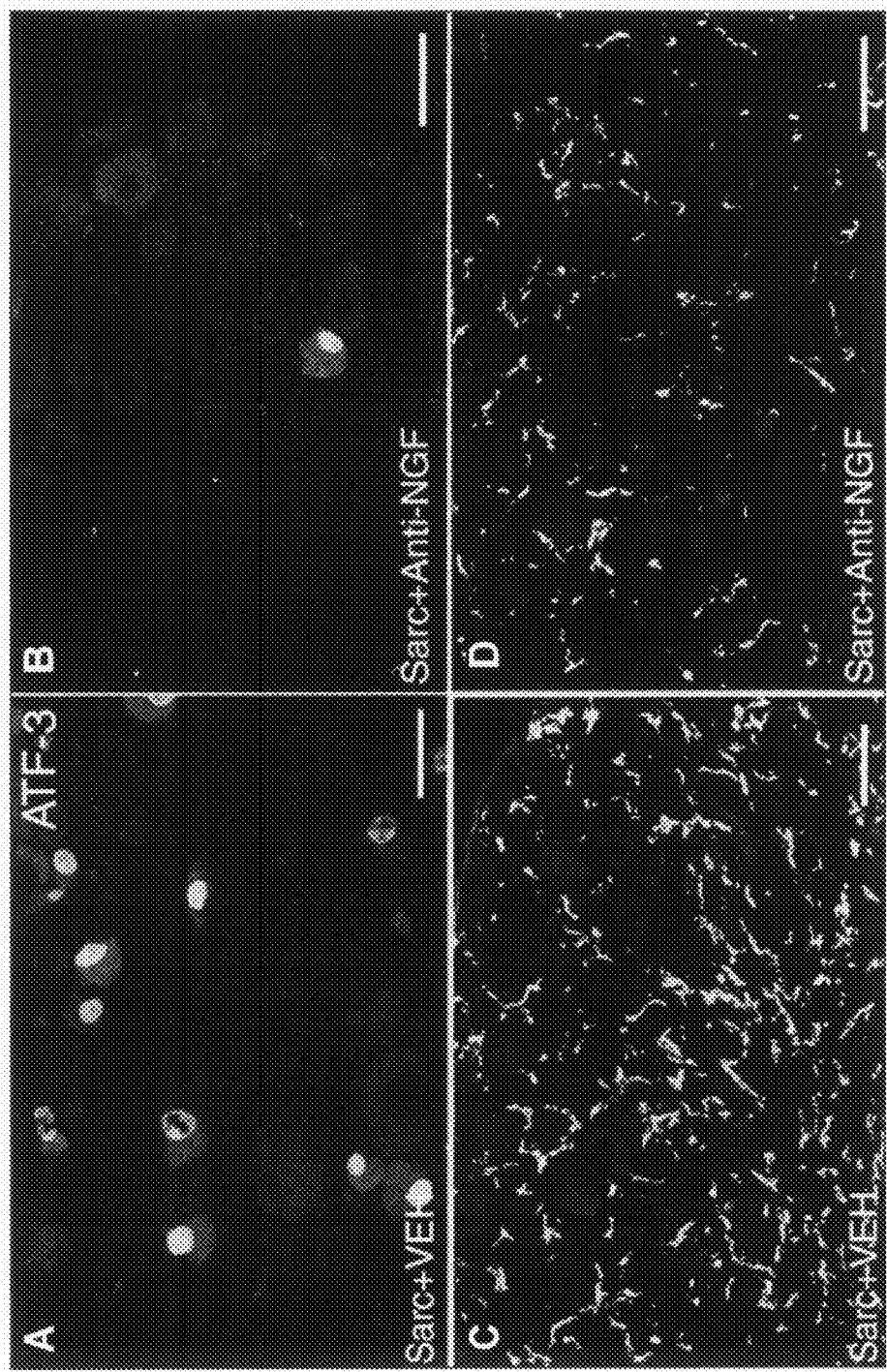
FIG. 8 shows photographs demonstrating that treatment with anti-NGF antagonist antibody reduced neurochemical changes and macrophage infiltration in dorsal root ganglia (DRG) of tumor-bearing animals.

Anti-NGF treatment modulated peripheral changes induced by bone cancer in the DRG. Activating transcription factor-3 (ATF-3), which is in the ATF/CREB family, has previously been shown to be up-regulated in a model of peripheral nerve injury. Tsujino et al., *Molecular & Cellular Neurosciences* 15:170–82 (2000). This up-regulation is seen in sensory and motor neuron cell bodies and is known to label injured neurons. There was significant increase in the percentage of ATF-3-IR neurons in L2 DRG ipsilateral to the sarcoma-injected femur (14.0±5.9% of total neurons in L2 expressed ATF-3; FIG. 8a) as compared to sham+vehicle (1.6±0.5% of total neurons in L2 expressed ATF-3). Treatment with anti-NGF significantly attenuated the expression of ATF-3 (2.6±1.0% of total neurons in L2 expressed ATF-3; FIG. 8b) 14 days post tumor injection.

Macrophage infiltration has been shown to be up regulated due to peripheral nerve damage. Abbadie et al., *Proc. Natl. Acad. Sci. USA.* 100: 7947–52 (2003); Myers et al., Exp. Neurol. 141: 94–101 (1996); Tofaris et al., *J. Neurosci.* 22: 6696–703 (2002). An antibody raised against CD68 (ED-1), a lysosomal protein expressed by activated tissue macrophages, was used to assess macrophage infiltration in sarcoma-injected mice. There was an up regulation in the number of CD68-IR neurons in the ipsilateral DRG of sarcoma+vehicle mice (119.6±12.1 cellular profiles/L2 ipsilateral DRG; FIG. 8c) compared to sham+vehicle (80.6±6.0 cellular profiles/L2 ipsilateral DRG). Anti-NGF treatment significantly reduced the up-regulation of CD68-IR neurons in the ipsilateral DRG (92.0±9.9 cellular profiles/L2 ipsilateral DRG; FIG. 8d) in sarcoma-injected mice, indicating a significant reduction in the number of activated and infiltrating microphage within the ipsilateral L2 DRG of tumor bearing animals.

Figure 9:
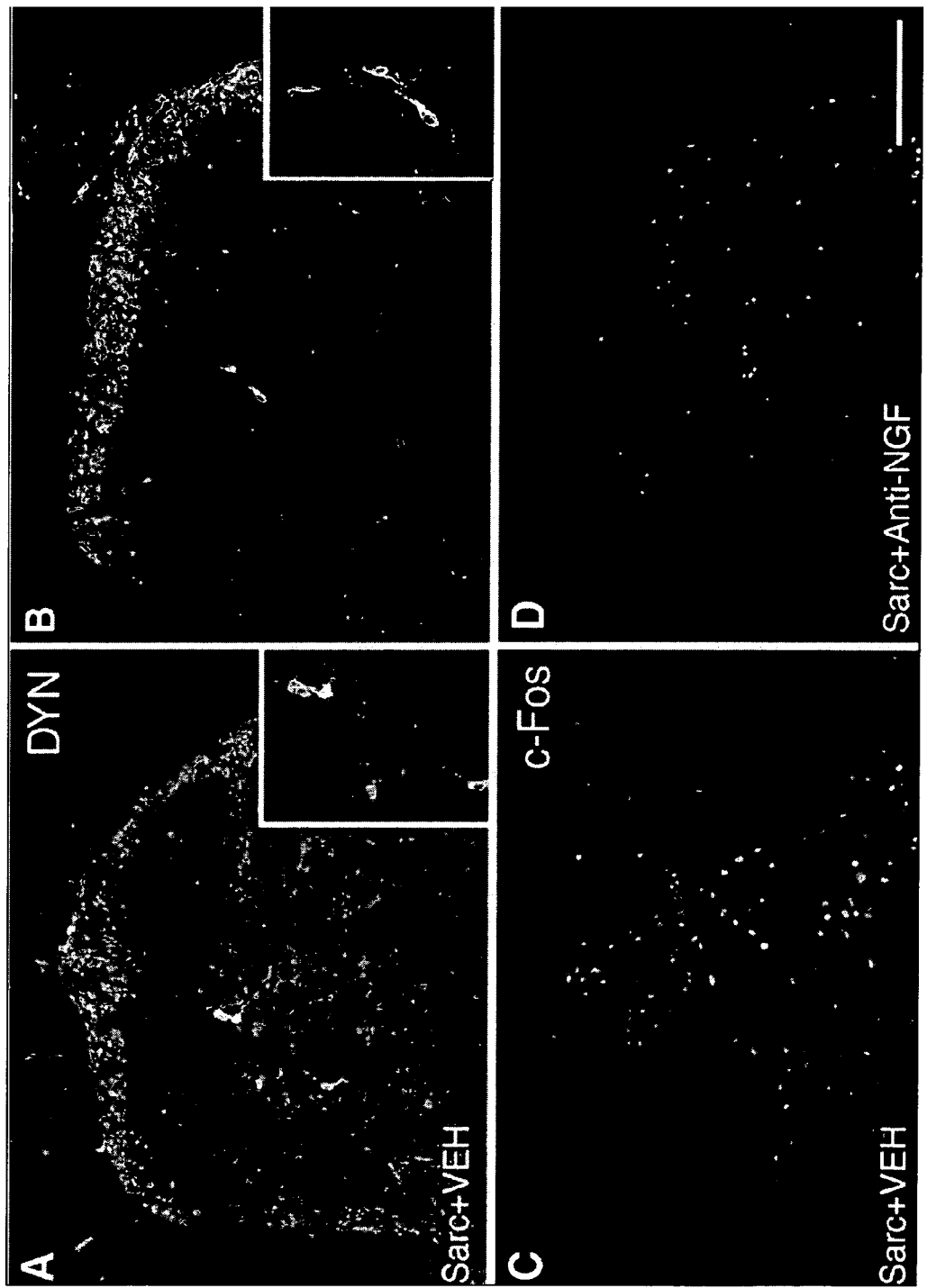
FIG. 9 shows micrographs demonstrating that neurochemical changes associated with central sensitization were attenuated by administration of anti-NGF.

Anti-NGF treatment modulated central changes induced by bone cancer in the spinal cord. Expression of dynorphin has been shown to be involved in the maintenance of chronic pain. Vanderah et al., Pain 92: 5–9 (2001). Dynorphin expression has also been shown to be up-regulated in the dorsal horn of the spinal cord in several persistent pain states. Iadarola, et al., Brain Res. 455: 205–212 (1988); Noguchi et al., Molecular Brain Research 10: 227–233 (1991); Schwei et al., J. Neurosci. 19: 10886–97 (1999). In sham+vehicle mice, a small amount of spinal neurons expressed dynorphin in deep spinal laminae (2.3±1.1 dyn-IR neurons/L3/L4 section). In contrast, sarcoma+vehicle mice expressed significantly more dynorphin-IR neurons (6.0±0.5 dyn-IR neurons/L3/L4 section; FIG. 9A). Anti-NGF treatment significantly reduced the up-regulation of dynorphin expression (2.0±0.6 dyn-IR neurons/L3/L4 section; FIG. 9B) in sarcoma-injected mice.

Immediate-early gene activation was prevented by anti-NGF treatment. The expression of c-Fos in the deep dorsal horn (laminae III–VI) has been utilized as a marker of central sensitization in sarcoma-induced bone cancer pain states. Honore et al., Nat. Med. 6: 521–8 (2000); Honore et al., Neuroscience 98:585–598 (2000); Luger et al., Cancer Research 61: 4038–4047 (2001); Schwei et al., J. Neurosci. 19: 10886–97 (1999). Normal, non-noxious palpation of sham-operated animals resulted in minimal expression of c-Fos in deep laminae. Sabino et al., Cancer Res. 62: 7343–9 (2002). In the bone cancer state, sarcoma+vehicle mice exhibited an increased number of c-Fos-IR neurons (27.7±4.9; cFos-IR neurons/L3/L4 section; FIG. 9C) and treatment with anti-NGF significantly reduced this expression (11.1±1.9; cFos-IR neurons/L3/L4 section; FIG. 9D).

RT PCR Results. In order to see whether the sarcoma tumor cells were a possible source of NGF, 2472 cells grown in culture were assessed for their level of NGF mRNA by RT-PCR. These levels were compared to several normal tissues of the mouse, as well as the level of NGF mRNA from the male mouse salivary gland, a source of aberrantly high exocrine NGF. As seen in Table 3 below, sarcoma 2472 cells in vitro contained readily detectable NGF mRNA. This level is in the range of NGF mRNA levels obtained from normal tissues expressing high levels of NGF mRNA, such as iris. Shelton et al., Proc. Natl. Acad. Sci. USA. 81:7951–5 (1984). However, this level is several orders of magnitude below the level of NGF mRNA present in male mouse salivary gland.

TABLE 3

RT PCR data showing level of NGF expression

| Tissue type | Arbitrary Units |
| --- | --- |
| Brain | 1.2 ± 0.8 |
| Atria | 1.9 ± 0.7 |
| 2472 cells | 8 ± 1.1 |

TABLE 3-continued

RT PCR data showing level of NGF expression

| Tissue type | Arbitrary Units |
| --- | --- |
| Iris | 8.8 ± 3.6 |
| Submaxillary Gland | 1359.1 ± 583.7 |

Example 3

Effect of Anti-NGF Monoclonal Antibody in Treating Bone Cancer Pain in a Murine Model Developed by Intramedullary Injection of Osteoblastic Prostate Tumor Cells into the Femur Methods Murine prostate model of bone cancer pain. A murine prostate model of bone cancer pain was used to assess the efficacy of treatment with anti-NGF antibody 911 (a mouse monoclonal antibody; see Hongo, et al., Hybridoma 19:215–227 (2000)). Osteoblastic canine carcinoma (ACE-1, gift from Dr. Thomas J. Rosol, Ohio State Univeristy) cells were maintained and injections of tumor cells were performed as previously described. Sabino et al., Cancer Res. 62: 7343–7349, 2002; Honore et al., Nature Medicine 6: 521–528, 2000; Honore et al., Prog. Brain Res. 129: 389–397, 2000; Luger et al., Cancer Research 61: 4038–4047, 2001. In brief, ACE-1 cells were grown in media at 37° C. and 5% $CO_2$. The cells are grown in T75 flasks (7.5 cm$^2$) and passaged at 80–90% confluency, twice per week. Only passages between 3 and 11 were used in this study. On day 0, following induction of general anesthesia with sodium pentobarbital (50 mg/kg, i.p.), an arthrotomy was performed exposing the condyles of the distal femur. Hank's buffered sterile saline (HBSS, Sigma Chemical Co., St. Louis, Mo.; 20 µl; sham, n=7) or media containing 10$^5$ osteoblastic canine ACE-1 cells (20 µl, ACE-1, n=60) was injected into the intramedullary space of the mouse femur and the injection site sealed with dental amalgam (Dentsply, Milford, Del.), followed by irrigation with sterile filtered water. Experiments were performed on a total of 89 8–10 week old adult male athymic nude mice (Harlan Laboratories, Madison, Wis.), weighing 20–32 g. The mice were housed in accordance with the National Institutes of Health guidelines under specific pathogen free (SPF) conditions in autoclaved cages maintained at 22° C. with a 12-hour alternating light and dark cycle and were given autoclaved food and water ad libitum.

A day 19 post-injection endpoint was used, as this is the time point when the tumor is still confined to the bone, there is maximal presentation of cancer-related pain behaviors and tumor-induced bone remodeling. Sham animals were used for control analysis of behavioral experiments and bone histology/immunohistochemistry, as naïve animals were not significantly different from sham behaviorally 9 days post-tumor injection.

Treatment with anti-NGF antibody or morphine. On days 7, 12, and 17 post tumor-injection, ACE-1-injected animals were intraperitoneally (i.p.) injected with anti-NGF antibody 911 at 10 mg/kg (ACE-1+anti-NGF, n=9); ACE-1-injected animals were injected (i.p.) with saline (ACE-1+veh, n=21; 1.4 µl/kg); and sham-injected animals were injected (i.p.) with saline (sham+veh, n=7). All animals were behaviorally analyzed between days 7 and 19.

For behavioral comparison of anti-NGF antibody to morphine sulfate, mice were given an acute dose of morphine 15 minutes prior to behavioral testing (naïve: n=6; sham: n=7; ACE-1+vehicle: n=7; ACE-1+anti-NGF: n=7; ACE-1+morphine 10 mg/kg, s.c.: n=8; ACE-1+morphine 30 mg/kg, s.c.: n=8). For thermal and mechanical sensitivity testing and the assessment of hindpaw skin innervation, naïve mice were divided into two treatment groups receiving either sterile saline (naïve+vehicle: n=8) or anti-NGF antibody (naïve+anti-NGF: n=8, 10 mg/kg, i.p.).

Behavioral analysis. Animals were tested for pain-related behaviors both prior to and on day 7, 9, 11, 13, 15, 17 and 19 post-tumor implantation or sham injection. Animals were behaviorally tested using the following tests: ongoing pain (spontaneous guarding and flinching) and movement-evoked pain (palpation-evoked guarding and palpation-evoked flinching). Animals were placed in a clear plastic observation box with a wire mesh floor and allowed to habituate for a period of 30 min. After acclimation, spontaneous guarding and spontaneous flinching, were assessed. Palpation-induced guarding and flinching were measured after the 2 min period of normally non-noxious palpation of the distal femur in ACE-1 and sham-injected animals. These tests were performed as described in Examples 1 and 2.

Euthanasia and processing of tissue. Mice were sacrificed 19 days post-tumor injection and the tissues were processed for immunohistochemical analysis of femora and hindpaw skin as previously described. Honore et al., Prog. Brain Res. 129:389–397, 2000; Honore et al., *Nat. Med.* 6: 521–8 (2000); Luger et al., *Cancer Research* 61: 4038–4047 (2001). Mice were euthanized with $CO_2$ and perfused intracardially with 12 ml 0.1 M phosphate buffered saline (PBS) followed by 25 ml 4% formaldehyde/12.5% picric acid solution.

Hindpaw plantar skin was removed, post-fixed in the perfusion fixative, and cryoprotected in 30% sucrose for 24 hours. Serial skin sections, 60 μm thick, were cut on a sliding microtome, collected in PBS, and processed as free floating sections. Following sectioning, plantar skin sections were briefly rinsed in PBS and then incubated in blocking solution (3% normal donkey serum (NDS) 0.3% Triton X-100 in PBS) for 1 hr followed by incubation overnight in the primary antibody. Skin sections were immunostained for calcitonin gene related peptide (CGRP) (1:15,000; Sigma, St. Louis, Mo.), tyrosine hydroxylase (TOH) (polyclonal rabbit anti-TOH, 1:2,000, Chemicon, Temecula, Calif.) and neurofilament H (Clone RT97) (polyclonal rabbit anti-RT-97, 1:2,500, Chemicon, Temecula, Calif.).

After incubation in primary antibody, sections were rinsed in PBS and then incubated in the secondary antibody solution for 3 hr. Secondary antibodies, conjugated to Cy3 or biotin (Jackson ImmunoResearch, West Grove, Pa.), were used at 1:600 or 1:500 respectively. To detect secondary antibodies conjugated to biotin: sections were rinsed in PBS and incubated in Cy3 conjugated streptavidin (1:4000; Jackson ImmunoResearch) for 45 minutes. To confirm specificity of the primary antibodies, controls included omission of the primary antibody or preabsorption with the corresponding synthetic peptide. Following immunostaining procedures, plantar skin sections were rinsed, mounted onto gelatin-coated slides. Mounted sections were then dehydrated in alcohol gradients (70, 90, 100%), cleared in xylene and coverslips were mounted with DPX (Fluka, Buchs, Switzerland).

Following radiological examination, at day 19 post-tumor injection, right (internal control) and left (tumor-bearing) femora were fixed in picric acid and 4% formalin at 4° C. overnight and decalcified in 10% EDTA (Sigma) for no more than 14 days. Bones were then embedded in paraffin. Femoral sections, 5 μm thick were cut in the lateral plane and stained with tartrate-resistant acid phosphatase (TRAP) and hematoxylin and eosin (H&E) to visualize histological features of the normal bone marrow, tumor, osteoclasts, osteoblasts, and macrophages (Ms).

Immunohistochemical analysis of the sham and cancerous femora was performed on decalcified, paraffin embedded 14 μm serial sections. Endogenous peroxidases were quenched by incubating the sections in 2% hydrogen peroxide for 1 hour. Sections were then rinsed three times with PBS for 10 minutes and blocked in TSA blocking buffer (TSA-Plus Cyanine 3 System, PerkinElmer Life Sciences, Inc., Boston, Mass.) for 1 hour. Primary antiserum was added upon removal of the blocking buffer and allowed to incubate at room temperature overnight. Primary afferent unmyelinated and thinly myelinated sensory nerve fibers were labeled using an antibody raised against polyclonal rabbit anti-calcitonin gene related peptide (CGRP) (1:15,000; Sigma). Sections were rinsed three times in TSA wash buffer for 10 minutes followed by 45 minute incubation in streptavidin HRP (1:4, 000). Sections were then rinsed three times with TSA wash buffer for 10 minutes. CY3-conjugated tyramine (1:600) from the TSA-Plus Cyanine 3 System was applied to the femora for 7 minutes, rinsed twice with TSA wash buffer and once with PBS. Finally, the sections were air dried, dehydrated through an alcohol gradient (70, 90 and 100%), cleared in xylene and mounted with DPX (Fluka).

Radiographical analysis of bone. Radiographs (Faxitron X-ray Corp., Wheeling, Ill.) of dissected femora were obtained at the day 19 time point to assess the extent of bone formation and destruction. Images were captured on Kodak Min-R 2000 mammography film (Eastman Kodak Co., Rochester, N.Y.; exposure settings: 7 sec, 21 kVp). Analysis of bone density was used to assess the extent of tumor-induced bone remodeling radiographically in the lateral plane of whole bone images at 5× magnification. Tumor and non-tumor bearing femora (n=8 for naïve+vehicle, sham+vehicle, ACE-1+vehicle, and ACE-1+anti-NGF) were analyzed using 'ImageJ (Research Services Branch, National Institute of Mental Health, Bethesda, Md.)' in a similar manner to a previously described protocol. Corey et al., *Prostate* 52: 20–33, 2002. Briefly, blank radiograph films and a standard step tablet (Eastman Kodak Co.) were used to develop a calibration curve. ImageJ was used to measure optical density and subsequently converted to transmission as follows: transmission=1/(antilog$_{10}$[Optical density]). Given data are determined from a negative image, thus transmission is a direct representation of bone density. An HP ScanJet 7400c scanner used to capture sub-saturation femoral radiographs and readings were recorded in duplicate from each femur. Results are presented as normalized transmission mean±SE.

Histological analysis of osteoblasts, osteoclasts, and macrophages, tumor growth and bone remodeling. Osteoblast proliferation was analyzed by quantifying the number of osteoblasts immediately in contact with regions of both tumor-induced new bone formation contained within the femur and cortical bone throughout the entire diaphyseal intramedullary space for naïve animals, sham-injected, and tumor-bearing mice. Diaphyseal intramedullary space was defined as extending from the proximal distal trabeculae to the distal proximal trabeculae and was selected for quantification as the predominant active bone remodeling occurs in this region. Osteoblasts were identified as those cells in direct contact with the newly advancing bone matrix and arranged in typical cubiodal or columnar epithelial layer and connected to one another via a thin process identifiable at high magnification (200× or greater). Results are presented as the number of osteoblasts/mm$^2$ of diaphyseal intramedullary space for naïve, sham-injected, and tumor-bearing mice. Osteoclast proliferation was determined by quantifying the number of TRAP+ osteoclasts at the bone/tumor interface and at the normal marrow/bone interface for naïve, sham-injected, and ACE-1-injected mice on TRAP stained femoral sections as previously described. Honore et al., Nat. Med. 6: 521–528 (2000). In brief, osteoclasts are histologically differentiated cells appearing as TRAP+ and which are closely associated with regions of bone resorption. These cells are multinucleate and are found in Howship's lacunae along the cortical and trabecular bone. Fawcett, D. W.; A Textbook of Histology. In: D. Dreibelbis (ed.), Bone, 11 edition, pp. 211–213. Philadelphia, Pa.: W.B. Saunders Company, 1986. Macrophage (Ms) proliferation was determined by quantifying the number of TRAP+ cells that were dispersed throughout the tumor and normal marrow not associated with the endosteal surface of the mineralized bone. Macrophages within the bone become activated due to tumor released factors that stimulate the cells, and the cellular appearance of these activated Ms is marked by their highly irregular surface, multiple lamellipodia and phagocytic vacuoles. Results are expressed as the mean number of osteoclasts per $mm^2$ or Ms per $mm^2$ of diaphyseal intramedullary space, respectively.

Femora containing ACE-1 cells were imaged using bright field microscopy on a Nikon E600 fluorescence microscope equipped with a SPOT II digital camera utilizing SPOT image capture software (Diagnostic Instruments, Sterling Heights, Mich.). The total area of intramedullary space and the percent of intramedullary space occupied by tumor, bone formation, and remaining hematopoeitic cells was calculated using Image Pro Plus v3.0 software (Media Cybernetics, Silver Spring, Md.). Sabino et al., Cancer Res. 62: 7343–7349, 2002; Sevcik et al., Pain 111: 169–180, 2004. Bone formation was analyzed using the same H&E stained femora sections used to quantify tumor growth. Femur sections were viewed under polarized light to identify regions of woven and lamellar bone formation. Regions of woven bone formation were imaged with the SPOTII digital camera and quantified using Image Pro Plus v3.0 software. Results are presented as area of tumor, tumor-induced bone formation, and remaining hematopoeitic cells as a percentage of total intramedullary area.

Quantification of sensory fibers in bone and skin. The number of sensory nerve fibers was determined as previously described. Mach et al., Neuroscience 113: 155–166, 2002. Briefly, the number of CGRP-IR fibers in three bone regions (proximal, distal and diaphyseal) and the three bone tissues (periosteum, mineralized bone and marrow) were identified using a MRC-1024 Confocal Imaging system (Bio-Rad, Richmond, Calif.) equipped with a 20× objective. Nerve fiber counts were performed by viewing six femur sections per mouse with an Olympus BH-2 fluorescence-equipped microscope. Only nerve fibers greater than 30 μm were included in the analysis. To measure the total surface area ($mm^2$) of each bone, we analyzed the same femur sections from which nerve fiber counts were obtained. The total bone area was measured on digital images of the femur sections acquired using a SPOTII digital camera and Image Pro Plus v.3.0 software. Results are presented as the number of fibers counted per total bone area.

Quantification of epidermal innervation density was performed on 4 randomly selected plantar hindpaw skin sections per mouse. The total number of CGRP, TOH and RT97-IR nerve fibers were counted at 200× magnification. Counting rules were established to count only single intra-epidermal fibers and not multiple branches of the same fiber. McCarthy et al., Neurology 45: 1848–1855, 1995. The total length of epidermis in all sections quantified was measured using a 1 $cm^2$ eyepiece grid. Only nerve fibers that were at least 30 μm in length, and projected into the epidermis were counted. Results are given as the mean number of intra-epidermal nerve fibers per mm length per mouse.

RC PCR analysis of mRNA levels of NGF in ACE-1 cells. Total RNA from dog brain or dog prostate tumor cells ACE-1 was prepared according to manufacturer's instructions using the RNeasy micro kit (Qiagen), and the RNA was quantified using Ribogreen reagent (Molecular Probes). Two-step RT-PCR was performed using the TaqMan Gold RT-PCR kit (Applied Biosystems). The RNA was reverse transcribed using random hexamers, and the cDNA was amplified using a primer/probe set specific for NGF (LB041: AACAGGACT-CACAGGAGCAA (SEQ ID NO:6), LB042: CGGCACTTG-GTCTCAAAGAA (SEQ ID NO:7), and LB045: AATGT-TCACCTCTCCCAGCACCATCA (SEQ ID NO:8)). The samples were analyzed in duplicate from the RT step and normalized to total RNA input.

Statistical analysis. The Statview computer statistics package (SAS Institute, Inc., Cary, N.C.) was used to perform statistical tests. One-way ANOVA was used to compare behavioral results, bone histological results, and immunohistochemical measures among the experimental groups. For multiple comparisons, Fishers's PLSD (protected least significant difference) post hoc test was used. Significance level was set at $P<0.05$. The individual investigator responsible for behavior, immunohistochemistical analysis and scoring bone remodeling was blind to the experimental situation of each animal.

Results

Anti-NGF therapy attenuated bone cancer pain to a greater extent than morphine sulfate but did not affect baseline thermal or mechanical thresholds. Ongoing pain was analyzed by measuring spontaneous guarding and flinching over a 2-minute time period. ACE-1+vehicle mice demonstrated a greater time spent guarding (7.7±0.8 sec, day 19) as compared to the sham+vehicle controls (0.6±0.3 sec, day 19, FIG. 10A). Additionally, ACE-1+vehicle mice exhibited an increased number of flinches (11.9±1.2, day 19) as compared to sham+vehicle controls (1.0±0.4, day 19, FIG. 10B). Administration of anti-NGF in ACE-1-injected mice significantly attenuated spontaneous guarding (1.2±0.4 sec, day 19) as compared to ACE-1+vehicle mice (FIG. 10A). Anti-NGF treatment also significantly reduced spontaneous flinching in ACE-1-injected mice (2.1±0.7, day 19) as compared to ACE-1+vehicle (FIG. 10B). In preliminary studies, no significant behavioral differences or side effects were observed between sham-operated controls receiving either vehicle or anti-NGF.

Anti-NGF therapy had no effect on either normal thermal response (10.2±0.4 sec, day 19) as compared to naïve+vehicle (11.2±0.4 sec, day 19, FIG. 10C) or normal mechanical response (5.4±0.3 g, day 19) as compared to naïve+vehicle (5.2±0.4 g, day 19, FIG. 10D).

Animals were tested to compare the efficacy of morphine sulfate (MS) to the anti-NGF antibody in reducing bone cancer-related behaviors. Behavioral assessment on days 11 and 19 post-tumor injection revealed that ACE-1+vehicle animals showed statistically longer time guarding of the injected limb (6.0±1.0 and 7.6±1.2 sec, day 11 and 19, respectively) compared to sham+vehicle mice (0.4±0.2 and 0.6±0.3 sec, day 11 and 19, respectively, FIG. 10E). ACE-1+vehicle also showed statistically larger number of flinches of the injected limb (8.6±1.2 and 11.7±1.7, day 11 and 19, respectively) compared to sham+vehicle mice (0.7±0.3 and 1.0±0.4, day 11 and 19, respectively, FIG. 10F). Ongoing guarding was significantly reduced by either chronic treatment of anti-NGF (2.1±1.1 and 1.4±0.4 sec, day 11 and 19, respectively), acute 10 mg/kg morphine sulfate (3.5±0.3 and 4.0±0.5 sec, day 11 and 19, respectively) or acute 30 mg/kg morphine sulfate (2.2±0.3 and 2.0±0.4 sec, on day 11 and 19, respectively), as compared to ACE-1+vehicle mice (FIG. 10E). Ongoing flinching was also significantly reduced by either chronic treatment of anti-NGF (3.4±1.7 and 2.6±0.6, day 11 and 19, respectively), acute 10 mg/kg morphine sulfate (5.6±0.5 and 6.8±0.7, day 11 and 19, respectively) or acute 30 mg/kg morphine sulfate (3.6±0.5 and 3.5±0.7, day 11 and 19, respectively), as compared to ACE-1+vehicle mice (FIG. 10F). Anti-NGF therapy significantly attenuated the bone cancer-related pain behaviors more effectively than acute 10 mg/kg morphine sulfate. No differences in terminal weights were observed between sham+vehicle (27±1 g), ACE-1+vehicle (27±1 g), and ACE-1+Anti-NGF (26±1 g) animals. In these studies, no significant behavioral differences or side effects, such as ataxia, illness, or lethargy, were observed between animals receiving either vehicle or anti-NGF.

Anti-NGF therapy attenuated touch-evoked bone cancer pain. Touch-evoked pain behavior was also assessed. Palpation-induced guarding and flinching were measured after the 2 min period of normally non-noxious palpation of the distal femur in ACE-1 and sham-injected animals. As shown in FIGS. 10G and 10H, ACE-1-injected animals (administered with saline) developed touch-evoked pain behaviors by day 7 as assessed by palpation-induced guarding (FIG. 10G) and palpation-induced flinching (FIG. 10H) (both p<0.01, ANOVA) as compared to sham-injected animals (administered with saline). FIGS. 10G and 10H also shows that i.p. administration of anti-NGF antibody 911 significantly reduced palpation-induced guarding (FIG. 10G) and palpation-induced flinching (FIG. 10H) in ACE-1-injected mice from day 11 to day 19 post-ACE-1 tumor implantation as compared to administration of saline to ACE-1-injected mice (p<0.01, ANOVA, for both palpation-induced guarding and palpation-induced flinching). These results indicate anti-NGF antibody 911 reduces touch-evoked pain in ACE-1-injected mice.

Figure 11:
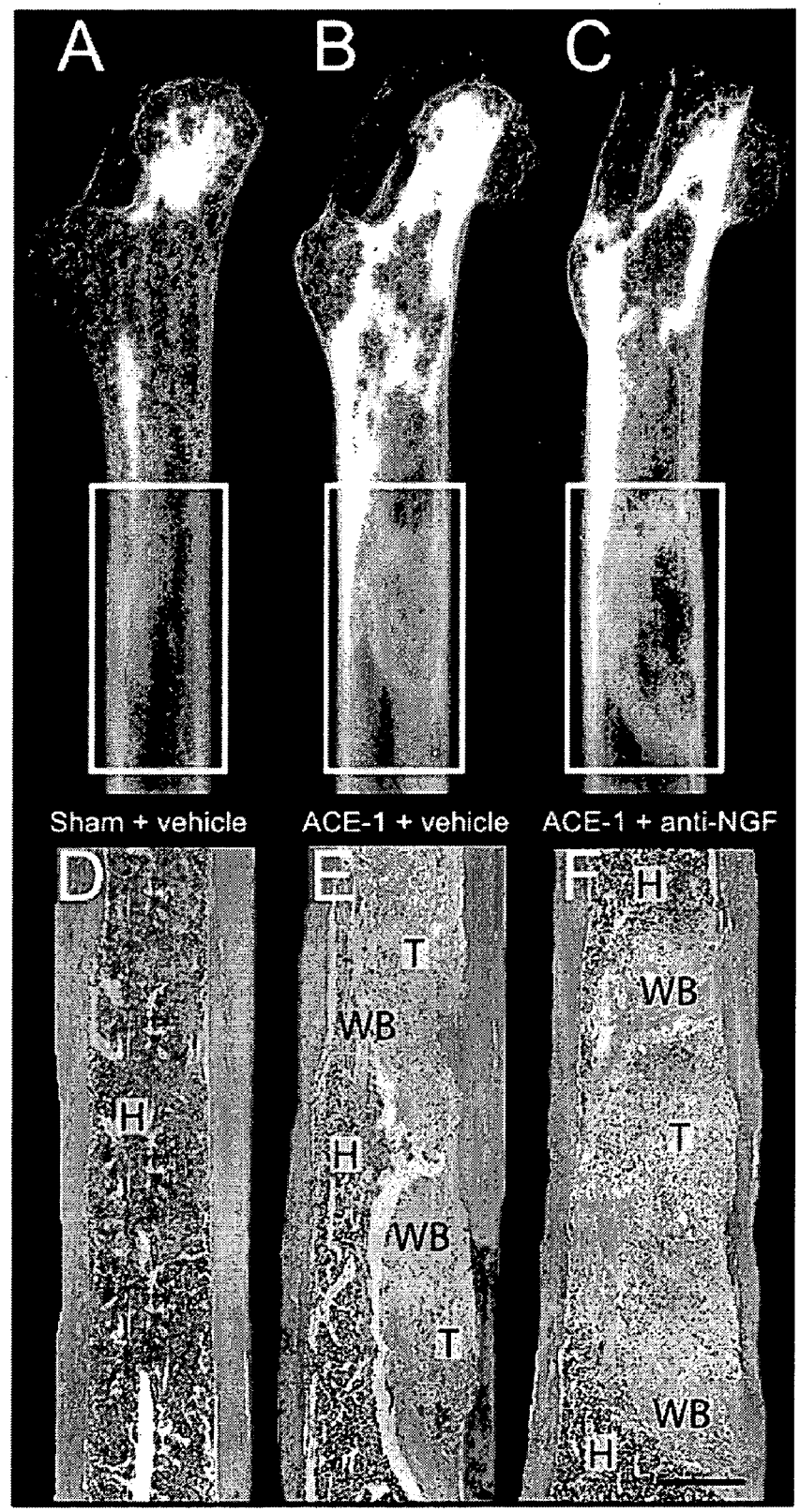
FIG. 11 are photographs demonstrating that anti-NGF antibody treatment had no effect on tumor burden or tumor-induced bone remodeling. Sham animals, given vehicle, (A) showed no radiographically or histologically (H&E) (D) apparent bone destruction at day 19, whereas ACE-1+vehicle animals (B, E) and ACE-1+anti-NGF animals (C, F) showed significant tumor growth and bone remodeling when examined radiologically and histologically. H=hematopoeitic cells; T=tumor; WB=ACE-1 induced bone formation; Scale bar=1.5 mm.
Figure 12:
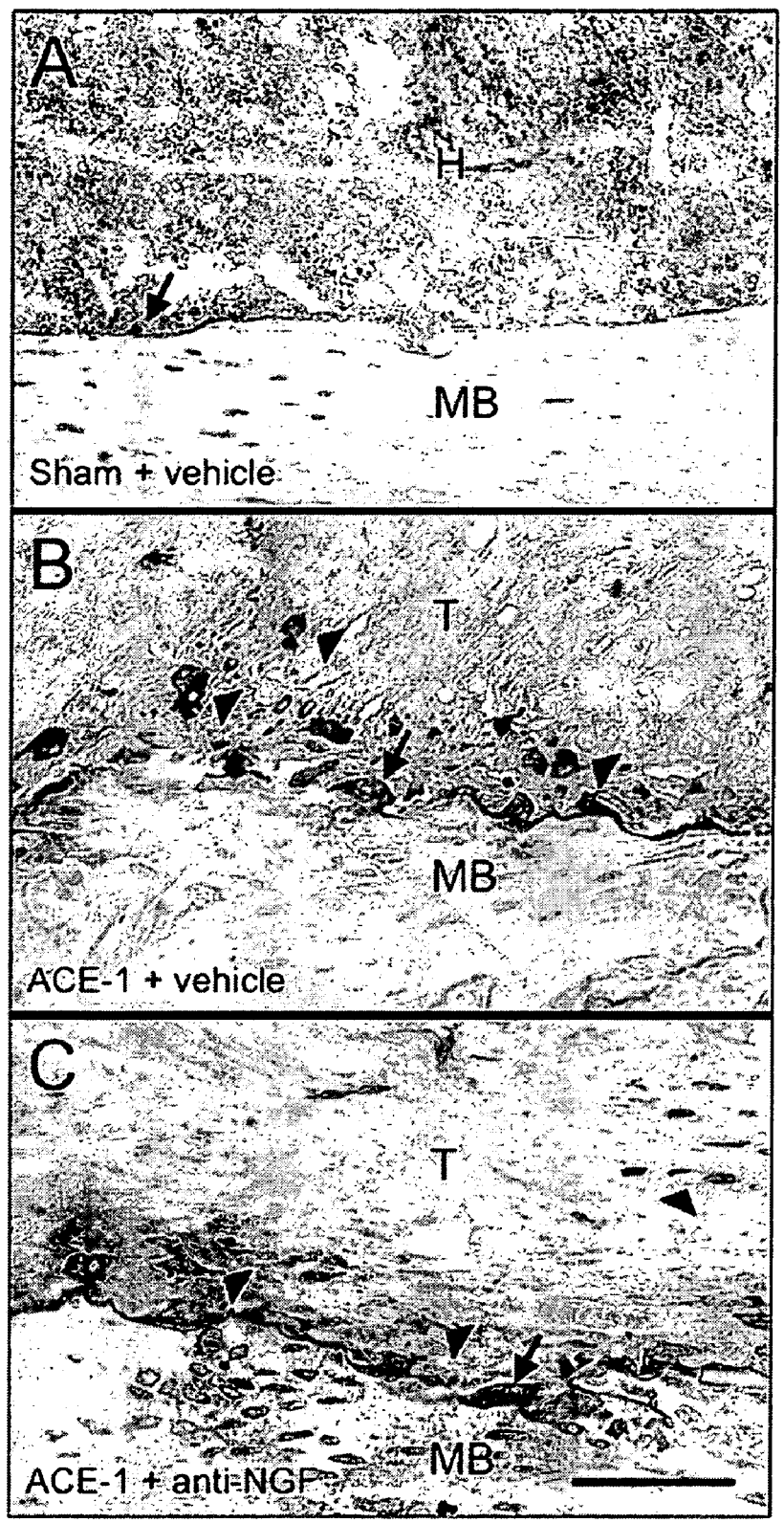
FIG. 12 are images demonstrating that anti-NGF therapy did not significantly reduce tumor-induced osteoclastogenesis. TRAP stained images of sham+vehicle (A), ACE-1+vehicle (B), and ACE-1+anti-NGF (C) illustrate that proliferation occurred in this model along regions of tumor-induced bone remodeling with an increase in the number of osteoclasts per $mm^2$ of diaphyseal intramedullary area in both the anti-NGF and vehicle-treated animals as compared to sham+vehicle and naïve+vehicle animals. There was no observable difference in histological appearance of the osteoclasts along the tumor/bone interface or macrophages throughout the tumor when anti-NGF-treated animals (C) were compared to vehicle treated animals (B). Sham+vehicle (A) animals presented osteoclast numbers and morphology, and macrophages which were not significantly different from naïve animals. Arrows=osteoclasts; Arrowheads=macrophages; MB=mineralized bone; H=hematopoeitic cells; T=tumor; Scale bar: 50 µm.

Anti-NGF therapy had no effect on markers of disease progression or tumor-induced bone formation. The effects of anti-NGF therapy on bone formation and destruction, tumor growth (FIG. 11), and osteoclast proliferation (FIG. 12) were examined 19 days post-tumor injection (Table 4 below). Sham-injected mice did not demonstrate significant bone remodeling (normalized transmission value of 115±2%) (FIG. 11A), osteoclast proliferation throughout the entire intramedullary space (16±10 osteoclasts/mm$^2$ diaphyseal intramedullary area) (FIG. 12A) or tumor cells (0±0%) (FIG. 11D), as assessed by radiological, TRAP and H&E analysis, respectively, as compared to ACE-1-injected mice. In ACE-1+vehicle mice, there was extensive, but nearly equivalent bone formation and destruction as observed and characterized by multifocal diaphyseal bridging and radiolucencies (normalized transmission value of 109±5%) (FIG. 11B), marked increase in the number of osteoclasts (FIG. 12B) and osteoblasts throughout the diaphyseal intramedullary area (47±3 osteoclasts/mm$^2$ and 127±7 osteoblasts/mm$^2$) and the tumor had filled most of the intramedullary space (60±7% of intramedullary space) (FIG. 11E). Treatment of tumor-bearing mice with anti-NGF antibody from day 7 post tumor injection resulted in no significant change in bone remodeling (normalized transmission value of 106±9%) (FIG. 11C), no reduction in ACE-1-induced osteoclast (FIG. 12C) or osteoblast proliferation throughout the diaphyseal intramedullary area (47±5 osteoclasts/mm$^2$ and 118±15 osteoblasts/mm$^2$) or tumor growth (57±6% of intramedullary space) as compared to ACE-1+vehicle animals (FIG. 11F).

TABLE 4

Histological & Radiological quantification of bone remodeling and tumor progression in Anti-NGF and Vehicle treated ACE-1 Animals

|  | Naive + vehicle | Sham + vehicle | ACE-1 + vehicle | ACE-1 + anti-NGF |
|---|---|---|---|---|
| 1. Bone Histomorphometry |  |  |  |  |
| Osteoclasts (OC #/mm$^2$ diaphyseal intramedullary space) | 7 ± 1 | 16 ± 10 | 47 ± 3[a,b] | 47 ± 5[a,b] |
| Osteoblasts (OB #/mm$^2$ diaphyseal intramedullary space) | 81 ± 4 | 72 ± 5 | 127 ± 7[a,b] | 118 ± 15[a,b] |
| Macrophages (Ms) (Ms/mm$^2$ diaphyseal intramedullary space) | 2 ± 1 | 2 ± 1 | 27 ± 2[a,b] | 24 ± 3[a,b] |
| Tumor-Induced New Bone Formation (% Diaphyseal Intramedullary space occupied) | 0 ± 0 | 0 ± 0 | 14 ± 2[a,b] | 13 ± 1[a,b] |
| Tumor Cells (% Intramedullary space occupied) | 0 ± 0 | 0 ± 0 | 60 ± 7[a,b] | 57 ± 6[a,b] |
| Hematopoetic Cells (% Intramedullary space occupied) | 100 ± 0 | 100 ± 0 | 26 ± 8[a,b] | 30 ± 6[a,b] |
| 2. Radiological Bone Remodeling Score |  |  |  |  |
| % Normalized Transmission $\left( \frac{1/(\text{antilog}[\text{Optical Density}])}{(\text{Naive Transmission})} \times 100\% \right)$ | 100 ± 2 | 115 ± 2 | 109 ± 5 | 106 ± 9 |

[a]P < 0.05 versus naive.
[b]P < 0.05 versus sham (one way ANOVA, Fisher's PLSD).

Nineteen days following tumor injection, ACE-1+vehicle mice displayed an increase in microphage (Ms) (27±2 Ms/mm$^2$ diaphyseal intramedullary area) as compared to sham+vehicle control mice (2±1 Ms/mm$^2$). Anti-NGF treatment of ACE-1-injected mice (24±3 Ms/mm$^2$) did not significantly alter Ms infiltration, as seen in the ACE-1+vehicle mice (Table 4).

Figure 13:
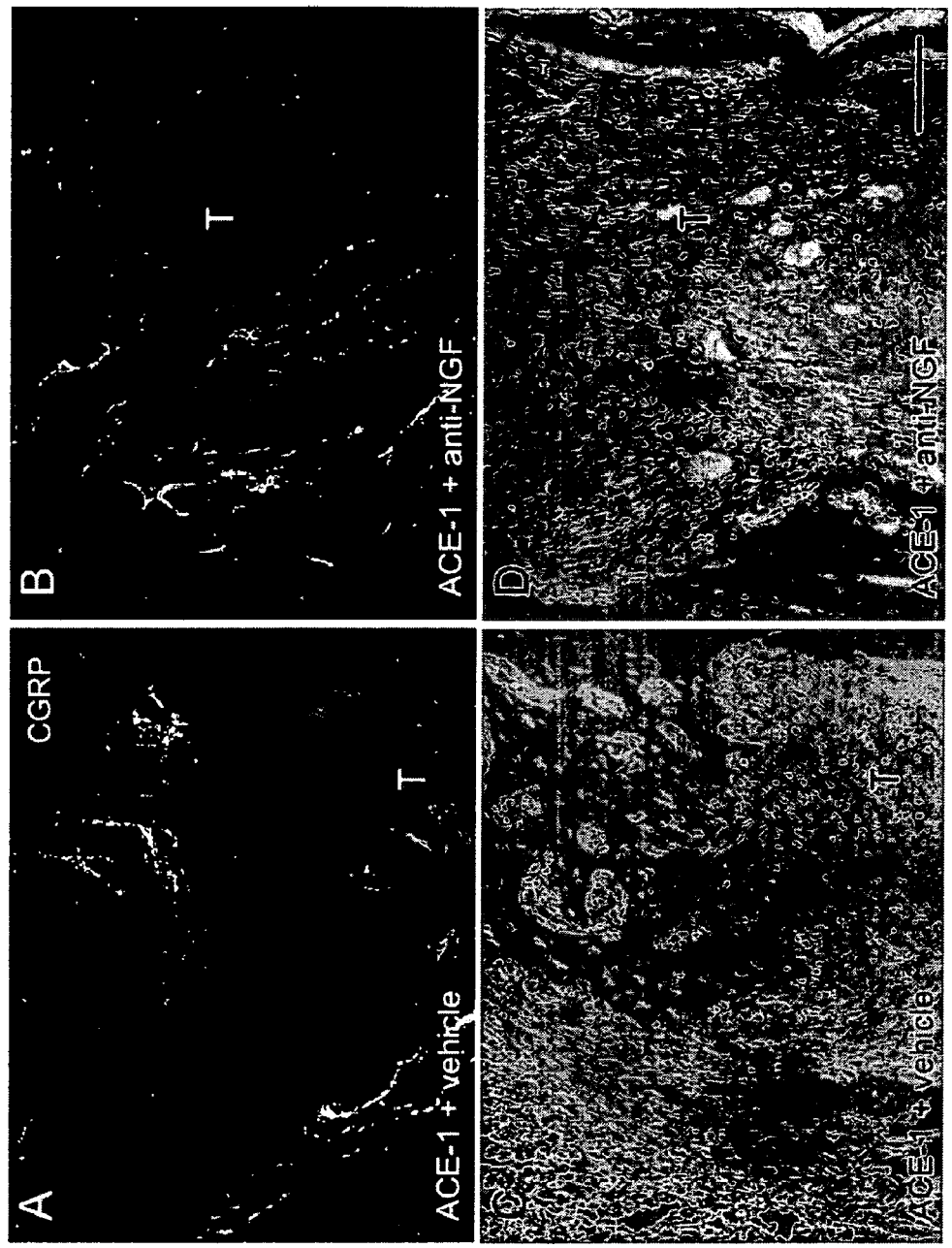
FIG. 13 are photographs demonstrating that anti-NGF therapy did not influence the density of calcitonin gene-related peptide immunoreactive (CGRP-IR) sensory fibers in the femur. There was no observable difference in the levels of immunofluorescence or density of CGRP-IR fibers between ACE-1+vehicle (A) animals and ACE-1+anti-NGF (B) animals. Also note that there was maintenance of CGRP-IR fibers with anti-NGF therapy. T=tumor; Scale bar: 50 µm.
Figure 14:
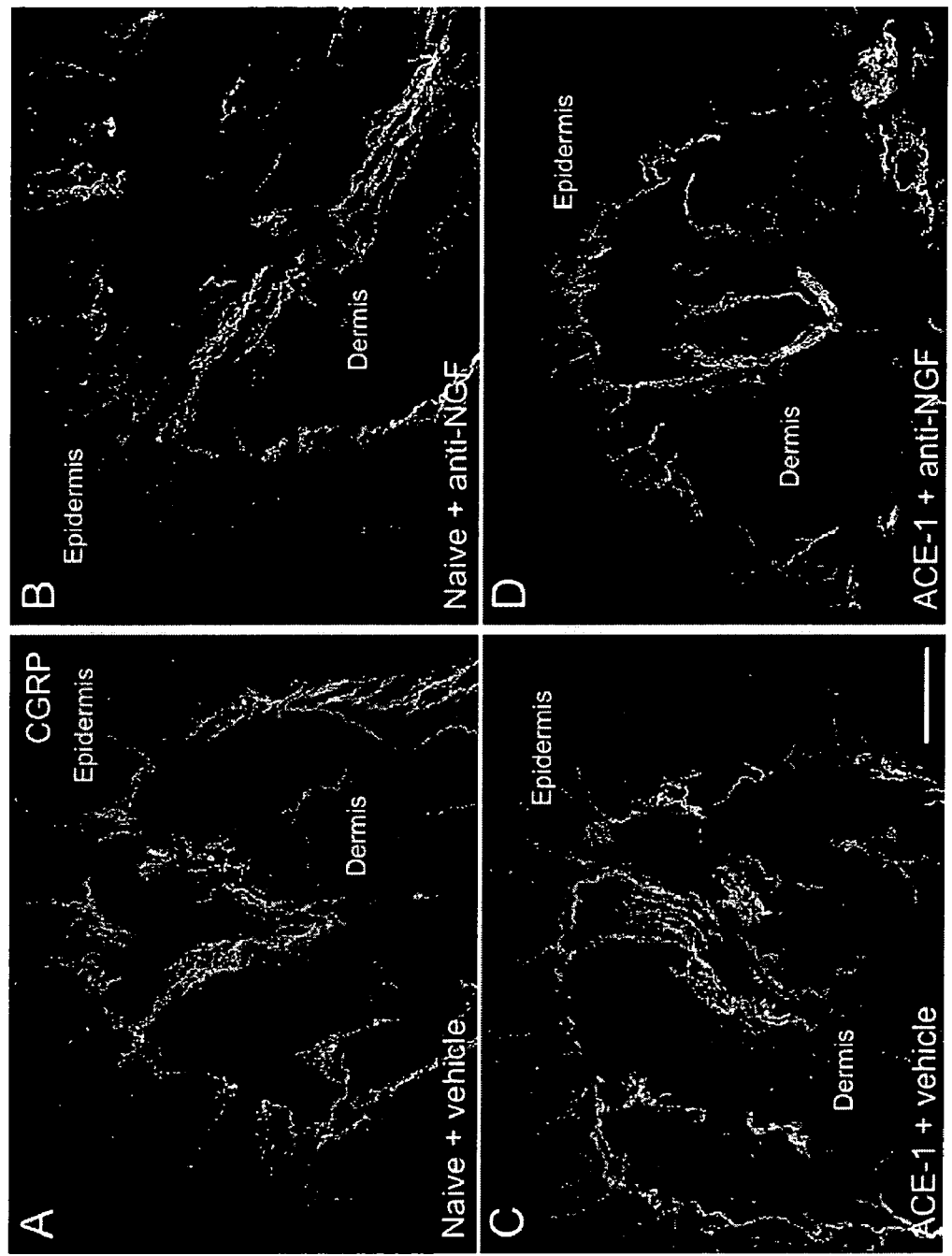
FIG. 14 are photographs demonstrating that anti-NGF therapy did not influence the density of calcitonin gene-related peptide immunoreactive (CGRP-IR) sensory fibers in the hindpaw skin. There was no observable difference in the levels of immunofluorescence or density of CGRP-IR fibers in skin between naïve+vehicle (A) mice and naïve+anti-NGF (B) mice exists. Similarly, there was no difference in the levels of immunofluorescence or density of CGRP-IR nerve fibers between ACE-1+vehicle (C) animals and ACE-1+anti-NGF (D) animals. Also note that there was no difference in CGRP-IR nerve fibers between the naïve and ACE-1 injected mice (A, B vs. C, D). Scale bar: 50 µm.

Anti-NGF therapy has no observable effect on sensory or sympathetic innervation in bone or skin. Thinly myelinated or unmyelinated peptidergic sensory nerve fibers (CGRP-IR), large myelinated sensory fibers (RT97-IR) and noradrenergic sympathetic nerve fibers (TOH-IR) were analyzed in the ACE-1 injected femora or the hindpaw plantar skin by immunohistochemistry using antibodies raised against CGRP, RT-97 and TOH, respectively. CGRP-IR nerve fibers were found throughout the entire bone (periosteum, mineralized bone. bone marrow and tumor) of the ACE-1+vehicle (23.5±1.9 fibers/mm$^2$) and ACE-1+anti-NGF (24.0±1.9 fibers/mm$^2$) animals as well as in the sham+vehicle (28.2±1.5 fibers/mm$^2$) and naïve+vehicle animals (24.6±2.4 fibers/mm$^2$) or naïve+anti-NGF animals (23.1±1.9 fibers/mm$^2$) (FIG. 14). There was no significant difference between the intensity or density of CGRP-IR fibers in ACE-1+vehicle (13.9±0.5 fibers/mm) and ACE-1+anti-NGF (15.2±0.7 fibers/mm) hindpaw skin samples (FIGS. 13A&B). Similarly, there was no significant difference between the intensity or density of CGRP-IR fibers in naïve+vehicle (14.4±0.4 fibers/mm) and naïve+anti-NGF (14.2±1.3 fibers/mm) hindpaw skin samples (FIGS. 14A&B). Differences in the density and intensity of RT97-IR and TOH-IR fibers were also undetectable in naïve+vehicle (4.2±2.2 RT97+fibers/mm; 16.0±2.7 TOH+ fibers/mm) and naïve+anti-NGF treated (8.0±0.6 RT97+ fibers/mm; 12.8±1.1 TOH+ fibers/mm) animals. There were no significant observable differences between the intensity or density of CGRP, RT97 or TOH-IR fibers in the skin samples of ACE-1+vehicle and ACE-1+anti-NGF versus the naïve+vehicle and naïve+anti-NGF animals.

Level of mRNA expression in ACE-1 cells. NGF expression in dog brain and ACE-1 cells were compared. Five independent ACE-1 samples were analyzed, and in each one NGF expression was below the level of detection of the PCR assay. NGF in dog brain crossed the threshold at cycle 35.2 of a 40 cycle experiment, whereas the ACE-1 samples failed to cross the threshold after 40 cycles. Thus, NGF mRNA expression in the ACE-1 samples was at least 27.8 fold less than expression in brain.

Example 4

Analgesic Effects of Anti-NGF Antibody E3 in Patients with Moderate to Severe Pain from Metastases to the Bone Due to Either Prostate or Breast Cancer In a randomized, placebo-controlled, double-blind study, analgesic effects (including time to onset, time to peak, duration as well as pain relief as measured by Visual Analogue Scale (VAS)) of intravenous doses (100 µg/kg, 300 µg/kg, or 1,000 µg/kg) of anti-NGF antibody E3 are compared with placebo in patients with moderate to severe pain from metastases to the bone due to either prostate or breast cancer. Adult males and females (ages between 35 to 75) who are experiencing moderate-to-severe pain from metastases to the bone due to either prostate or breast cancer, are enrolled in the study. During the screening period, patients are required to record their pain level four times per day and also record their use of other analgesic medication for 14 days prior to administration of anti-NGF antibody E3.

Two hundred and eighty patients are admitted to the study. Anti-NGF antibody E3 administration occurs on the mornings of Day 1 and Day 29, following the recording of two weeks of baseline pain level, other analgesic use, and adverse events. Two hundred and eighty patients are divided into four groups and each group has seventy patients. Patients in each group are treated with placebo, 100 µg/kg, 300 µg/kg, or 1,000 µg/kg of anti-NGF antibody E3.

Analgesic effects are assessed four times daily for fourteen days before dosing and for a period of six months after administration of antibody E3. Outcome is assessed as change from screening baseline (mean pain level for fourteen days prior to administration of placebo or antibody E3). Any decrease in pain scores and/or decrease in use of other analgesics in one or more groups of patients treated with anti-NGF antibody E3 compared to placebo demonstrate efficacy of the treatment with anti-NGF antibody E3.

Although the foregoing invention has been described in some detail by way of illustration and example for purposes of clarity of understanding, the descriptions and examples should not be construed as limiting the scope of the invention.

We claim:

1. A method for treating bone cancer pain in an individual comprising administering to the individual an effective amount of a nerve growth factor (NGF) antagonist.

2. The method of claim 1, wherein the bone cancer pain is from cancer originated in bone.

3. The method of claim 2, wherein the bone cancer pain is from osteosarcoma.

4. The method of claim 1, wherein the bone cancer pain is from cancer metastasized to bone.

5. The method of claim 4, wherein the bone cancer pain is from prostate cancer metastasized to bone.

6. The method of claim 4, wherein the bone cancer pain is from breast cancer metastasized to bone.

7. The method of claim 4, wherein the bone cancer pain is from lung cancer metastasized to bone.

8. The method of claim 4, wherein the bone cancer pain is from sarcoma metastasized to bone.

9. The method of claim 4, wherein the bone cancer pain is from renal cancer metastasized to bone.

10. The method of claim 1, wherein the NGF antagonist is an anti-NGF antagonist antibody.

11. The method of claim 10, wherein the anti-NGF antagonist antibody is a monoclonal antibody.

12. The method of claim 10, wherein the anti-NGF antagonist antibody is a humanized antibody.

13. The method of claim 10, wherein the anti-NGF antagonist antibody is a human antibody.

14. The method of claim 10, wherein the anti-NGF antagonist antibody binds human NGF.

15. The method of claim 14, wherein the anti-NGF antagonist antibody further binds rodent NGF.

16. The method of claim 14, wherein the anti-NGF antagonist antibody binds human NGF with a $K_D$ of about 0.1 nM or less than about 0.1 nM.

17. The method of claim 1, wherein the NGF-antagonist is not co-administered with an opioid analgesic.

* * * * *

UNITED STATES PATENT AND TRADEMARK OFFICE
CERTIFICATE OF CORRECTION

PATENT NO. : 7,425,329 B2
APPLICATION NO. : 11/102201
DATED : September 16, 2008
INVENTOR(S) : David L. Shelton et al.

It is certified that error appears in the above-identified patent and that said Letters Patent is hereby corrected as shown below:

In the Specification

Column 1, Line 16 Please change:
"This invention was made with U.S. Government support under National Institutes of Health grants 5R37-NS23970-16, 5R0I-DA11986-05 and 1R0I-NS048021-0IAI. The U.S. Government may have certain rights in this invention."

To:
"This invention was made with government support under DA011986, NS023970 and NS048021 awarded by the National Institutes of Health. The government has certain rights in the invention."

Signed and Sealed this
Seventeenth Day of May, 2022

Katherine Kelly Vidal
*Director of the United States Patent and Trademark Office*

SEQUENCE LISTING

```
<160> NUMBER OF SEQ ID NOS: 8

<210> SEQ ID NO 1
<211> LENGTH: 120
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ile Gly Tyr
            20                  25                  30

Asp Leu Asn Trp Ile Arg Gln Pro Pro Gly Lys Gly Leu Glu Trp Ile
        35                  40                  45

Gly Ile Ile Trp Gly Asp Gly Thr Thr Asp Tyr Asn Ser Ala Val Lys
```

```
                50                  55                  60
Ser Arg Val Thr Ile Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Gly Tyr Trp Tyr Ala Thr Ser Tyr Tyr Phe Asp Tyr Trp Gly
                100                 105                 110

Gln Gly Thr Leu Val Thr Val Ser
            115                 120

<210> SEQ ID NO 2
<211> LENGTH: 109
<212> TYPE: PRT
<213> ORGANISM: Artificial Sequence
<220> FEATURE:
<223> OTHER INFORMATION: Synthetic Construct

<400> SEQUENCE: 2

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn Asn
                20                  25                  30

Leu Asn Trp Tyr Gln Gln Lys Pro Gly Lys Ala Pro Lys Leu Leu Ile
             35                  40                  45

Tyr Tyr Thr Ser Arg Phe His Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Glu His Thr Leu Pro Tyr
                 85                  90                  95

Thr Phe Gly Gln Gly Thr Lys Leu Glu Ile Lys Arg Thr
                100                 105

<210> SEQ ID NO 3
<211> LENGTH: 17
<212> TYPE: DNA
<213> ORGANISM: Artificial Sequence
<220> FEATURE:
<223> OTHER INFORMATION: Synthetic Construct

<400> SEQUENCE: 3
gggctggatg gcatgct                                                     17

<210> SEQ ID NO 4
<211> LENGTH: 19
<212> TYPE: DNA
<213> ORGANISM: Artificial Sequence
<220> FEATURE:
<223> OTHER INFORMATION: Synthetic Construct

<400> SEQUENCE: 4
gcgtccttgg caaaacctt                                                   19

<210> SEQ ID NO 5
<211> LENGTH: 25
<212> TYPE: DNA
<213> ORGANISM: Artificial Sequence
<220> FEATURE:
<223> OTHER INFORMATION: Synthetic Construct

<400> SEQUENCE: 5
```

```
ccaagctcac ctcagtgtct gggcc                                          25

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
aacaggactc acaggagcaa                                                20

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
cggcacttgg tctcaaagaa                                                20

<210> SEQ ID NO 8
<211> LENGTH: 26
<212> TYPE: DNA
<213> ORGANISM: Artificial Sequence
<220> FEATURE:
<223> OTHER INFORMATION: Synthetic Construct

<400> SEQUENCE: 8
aatgttcacc tctcccagca ccatca                                         26
```